US012767663B2

(12) United States Patent
Stoessel

(10) Patent No.: US 12,767,663 B2
(45) Date of Patent: Oct. 20, 2026

(54) BENZIMIDAZOLE DERIVATIVES

(71) Applicant: Merck Patent GmbH, Darmstadt (DE)

(72) Inventor: Philipp Stoessel, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 1118 days.

(21) Appl. No.: 17/795,266

(22) PCT Filed: Jan. 27, 2021

(86) PCT No.: PCT/EP2021/051818

§ 371 (c)(1),
(2) Date: Jul. 26, 2022

(87) PCT Pub. No.: WO2021/151922

PCT Pub. Date: Aug. 5, 2021

(65) Prior Publication Data

US 2023/0139809 A1 May 4, 2023

(30) Foreign Application Priority Data

Jan. 29, 2020 (EP) .................................... 20154338

(51) Int. Cl.

| | |
|---|---|
| ***C07D 487/22*** | (2006.01) |
| ***C07D 487/10*** | (2006.01) |
| ***C07D 487/20*** | (2006.01) |
| ***C07D 495/10*** | (2006.01) |
| ***C07D 495/20*** | (2006.01) |
| ***C07D 498/10*** | (2006.01) |
| ***C07D 513/10*** | (2006.01) |
| ***H10K 85/60*** | (2023.01) |

(52) U.S. Cl.

CPC ......... *C07D 487/22* (2013.01); *C07D 487/10* (2013.01); *C07D 487/20* (2013.01); *C07D 495/10* (2013.01); *C07D 495/20* (2013.01); *C07D 498/10* (2013.01); *C07D 513/10* (2013.01); *H10K 85/656* (2023.02); *H10K 85/6572* (2023.02)

(58) Field of Classification Search

None

See application file for complete search history.

(56) References Cited

U.S. PATENT DOCUMENTS

| | | | | |
|---|---|---|---|---|
| 2011/0105778 | A1 | 5/2011 | Stoessel et al. | |
| 2011/0144366 | A1 | 6/2011 | Stoessel et al. | |
| 2011/0155954 | A1 | 6/2011 | Yersin et al. | |
| 2015/0322198 | A1* | 11/2015 | Hayer .................. | H10K 85/115 558/290 |

FOREIGN PATENT DOCUMENTS

| | | | |
|---|---|---|---|
| CN | 102076817 | A | 5/2011 |
| CN | 102076819 | A | 5/2011 |
| CN | 102077382 | A | 5/2011 |
| CN | 102279270 | A | 12/2011 |
| DE | 102008056688 | A1 | 5/2010 |
| KR | 2019-0001967 | A | 1/2019 |
| WO | 2010/054729 | A2 | 5/2010 |

OTHER PUBLICATIONS

Machine English translation of Jung et al. (KR 10-2019-0001967). Nov. 6, 2025.*

Ding et al., "Formation of N,S-Containing Polycycles via Base Promoted Dimerization of N-Phenacyl and N-Benzylbenzothiazolium Bromides", Organic & Supramolecular Chemistry, vol. 5, No. 1, 2020, pp. 1092-1096.

Spanget-Larsen et al., "Electronic States of Heterospirenes. Linear Dichroism in Stretched Polyethylene", J. Phys. Chem, vol. 94, No. 1, 1990, pp. 2334-2344.

Bourson J: "Etudes en serie benzimidazolique. III. Action des bases sur les sels de diphényl-1,3 benzimidazolium", Bulletin de la Societe Chimique de France, Society Francaise de Chimie , Paris, France, 10, 1971, pp. 3541-3547.

Celenligil-Cetin et al., "Metalloradical Complexes of Manganese and Chromium Featuring an Oxidatively Rearranged Ligand," Inorganic Chemistry, vol. 47, No. 23, Dec. 1, 2008, pp. 10998-11009.

International Search Report and Written Opinion received for PCT Patent Application No. PCT/EP2021/051818, mailed on May 4, 2021, 39 pages (20 pages of English Translation and 19 pages of Original Document).

* cited by examiner

*Primary Examiner* — Jay Yang

(74) *Attorney, Agent, or Firm* — Faegre Drinker Biddle & Reath LLP

(57) ABSTRACT

The invention relates to benzimidazole derivatives which are suitable for use in electronic devices, and to electronic devices, in particular organic electroluminescent devices, containing said compounds.

17 Claims, No Drawings

BENZIMIDAZOLE DERIVATIVES

CROSS-REFERENCE TO RELATED APPLICATIONS

This application is a national stage application (under 35 U.S.C. § 371) of PCT/EP2021/051818, filed Jan. 27, 2021, which claims benefit of European Application No. 20154338.6, filed Jan. 29, 2020, both of which are incorporated herein by reference in their entirety.

The present invention relates to benzimidazole derivatives for use in electronic devices, especially in organic electroluminescent devices, and to electronic devices, especially organic electroluminescent devices comprising these benzimidazole derivatives.

The structure of organic electroluminescent devices in which organic semiconductors are used as functional materials is described, for example, in U.S. Pat. Nos. 4,539,507, 5,151,629, EP 0676461, WO 98/27136, WO 2004/058911 A2, WO 2010/045729 A2 and KR 2019/0001967 A. Emitting materials used are frequently organometallic complexes which exhibit phosphorescence. For quantum-mechanical reasons, up to four times the energy efficiency and power efficiency is possible using organometallic compounds as phosphorescent emitters. In general terms, there is still a need for improvement in electroluminescent devices, especially also in electroluminescent devices which exhibit phosphorescence, for example with regard to efficiency, operating voltage and lifetime. Also known are organic electroluminescent devices comprising fluorescent emitters or emitters that exhibit TADF (thermally activated delayed fluorescence).

The properties of organic electroluminescent devices are not only determined by the emitters used. Also of particular significance here are especially the other materials used, such as host/matrix materials, hole blocker materials, electron transport materials, hole transport materials and electron or exciton blocker materials. Improvements to these materials can lead to distinct improvements to electroluminescent devices.

In general terms, in the case of these materials, for example for use as matrix materials, hole transport materials or electron transport materials, there is still a need for improvement, particularly in relation to the lifetime, but also in relation to the efficiency and operating voltage of the device. Moreover, the compounds should have high color purity.

It is therefore an object of the present invention to provide compounds which are suitable for use in an organic electronic device, especially in an organic electroluminescent device, and which lead to good device properties when used in this device, and to provide the corresponding electronic device.

More particularly, the problem addressed by the present invention is that of providing compounds which lead to a high lifetime, good efficiency and low operating voltage.

In addition, the compounds should have excellent processability, and the compounds should especially show good solubility.

In addition, the compounds, especially when they are used as matrix materials, as hole transport materials or as electron transport materials in organic electroluminescent devices, should lead to devices having excellent color purity.

Moreover, the compounds should be processible in a very simple manner, and especially exhibit good solubility and film formation. For example, the compounds should exhibit elevated oxidation stability and an improved glass transition temperature.

A further problem can be considered that of providing electronic devices having excellent performance very inexpensively and in constant quality.

Furthermore, it should be possible to use or adapt the electronic devices for many purposes. More particularly, the performance of the electronic devices should be maintained over a broad temperature range.

It has been found that, surprisingly, particular compounds described in detail below solve this problem and are of good suitability for use in electroluminescent devices and lead to improvements in the organic electroluminescent devices, especially in relation to lifetime, color purity, efficiency and operating voltage. The present invention therefore provides these compounds and electronic devices, especially organic electroluminescent devices, comprising such compounds.

The present invention provides a compound comprising at least one structure of the formula (I), preferably a compound of the formula (I), Formula (I)

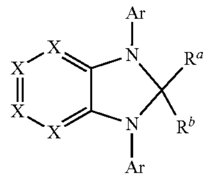

where the symbols and indices used are as follows:

$R^a$, $R^b$ is the same or different at each instance and is $N(Ar)_2$, $N(R)_2$, $B(Ar)_2$, $B(R)_2$, OAr, OR, SAr, SR, S(=O)Ar, S(=O)R, $S(=O)_2Ar$, $S(=O)_2R$, $P(=O)(Ar)_2$, $P(=O)(R)_2$, preferably $N(Ar)_2$, $N(R)_2$, $B(Ar)_2$, $B(R)_2$, OAr, OR, SAr, SR, S(=O)Ar, S(=O)R, $S(=O)_2Ar$, $S(=O)_2R$, or an aromatic or heteroaromatic ring system which has 5 to 60 aromatic ring atoms and may be substituted in each case by one or more R radicals, or an aryloxy or heteroaryloxy group which has 5 to 60 aromatic ring atoms and may be substituted by one or more R radicals; at the same time, two $R^a$, $R^b$ radicals together may also form a ring system or be bridged to one another by a bridge selected from B(R), $C(R)_2$, $Si(R)_2$, $Ge(R)_2$, C=O, C=NR, C=NAr', $C=C(R)_2$, O, S, S=O, $SO_2$, N(R), N(Ar'), P(R) and P(=O)R;

Ar is the same or different at each instance and is an aromatic or heteroaromatic ring system which has 5 to 60 aromatic ring atoms and may be substituted by one or more R radicals; the Ar group here may form a ring system with at least one further group;

X is N, CR or C if the Ar group forms a ring system via a bond, with the proviso that not more than two of the X groups in any cycle are N;

R is the same or different at each instance and is H, D, OH, F, Cl, Br, I, CN, $NO_2$, $N(Ar')_2$, $N(R^1)_2$, $C(=O)N(Ar')_2$, $C(=O)N(R^1)_2$, $C(Ar')_3$, $C(R^1)_3$, $Si(Ar')_3$, $Si(R^1)_3$, $B(Ar')_2$, $B(R^1)_2$, C(=O)Ar', $C(=O)R^1$, $P(=O)(Ar')_2$, $P(=O)(R^1)_2$, $P(Ar')_2$, $P(R^1)_2$, S(=O)Ar', $S(=O)R^1$, $S(=O)_2Ar'$, $S(=O)_2R^1$, $OSO_2Ar'$, $OSO_2R^1$, a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may in each case be substituted by one or more $R^1$ radicals, where one or more nonadjacent $CH_2$ groups may be replaced by $R^1C{=}CR^1$, C≡C, $Si(R^1)_2$, C=O, C=S, C=Se, $C{=}NR^1$, —C(=O)O—, $—C({=}O)NR^1—$, $NR^1$, $P({=}O)(R^1)$, —O—, —S—, SO or $SO_2$ or an aromatic or heteroaromatic ring system which has 5 to 60 aromatic ring atoms and may be substituted in each case by one or more $R^1$ radicals, or an aryloxy or heteroaryloxy group which has 5 to 60 aromatic ring atoms and may be substituted by one or more $R^1$ radicals; at the same time, two R radicals may also together or with a further group form a ring system;

Ar' is the same or different at each instance and is an aromatic or heteroaromatic ring system which has 5 to 60 aromatic ring atoms and may be substituted by one or more $R^1$ radicals; at the same time, it is possible for two Ar' radicals bonded to the same carbon atom, silicon atom, nitrogen atom, phosphorus atom or boron atom also to be joined together via a bridge by a single bond or a bridge selected from $B(R^1)$, $C(R^1)_2$, $Si(R^1)_2$, C=O, $C{=}NR^1$, $C{=}C(R^1)_2$, O, S, S=O, $SO_2$, $N(R^1)$, $P(R^1)$ and $P({=}O)R^1$;

$R^1$ is the same or different at each instance and is H, D, F, Cl, Br, I, CN, $NO_2$, $N(Ar'')_2$, $N(R^2)_2$, C(=O)Ar'', $C({=}O)R^2$, $P({=}O)(Ar'')_2$, $P(Ar'')_2$, $B(Ar'')_2$, $B(R^2)_2$, $C(Ar'')_3$, $C(R^2)_3$, $Si(Ar'')_3$, $Si(R^2)_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl group having 2 to 40 carbon atoms, each of which may be substituted by one or more $R^2$ radicals, where one or more nonadjacent $CH_2$ groups may be replaced by $—R^2C{=}CR^2—$, —C≡C—, $Si(R^2)_2$, C=O, C=S, C=Se, $C{=}NR^2$, —C(=O)O—, $—C({=}O)NR^2—$, $NR^2$, $P({=}O)(R^2)$, —O—, —S—, SO or $SO_2$ and where one or more hydrogen atoms may be replaced by D, F, Cl, Br, I, CN or $NO_2$, or an aromatic or heteroaromatic ring system which has 5 to 60 aromatic ring atoms, each of which may be substituted by one or more $R^2$ radicals, or an aryloxy or heteroaryloxy group which has 5 to 60 aromatic ring atoms and may be substituted by one or more $R^2$ radicals, or an aralkyl or heteroaralkyl group which has 5 to 60 aromatic ring atoms and may be substituted by one or more $R^2$ radicals, or a combination of these systems; at the same time, two or more, preferably adjacent $R^1$ radicals together may form a ring system; at the same time, one or more $R^1$ radicals may form a ring system with a further part of the compound;

Ar'' is the same or different at each instance and is an aromatic or heteroaromatic ring system which has 5 to 30 aromatic ring atoms and may be substituted by one or more $R^2$ radicals; at the same time, it is possible for two Ar'' radicals bonded to the same carbon atom, silicon atom, nitrogen atom, phosphorus atom or boron atom also to be joined together via a bridge by a single bond or a bridge selected from $B(R^2)$, $C(R^2)_2$, $Si(R^2)_2$, C=O, $C{=}NR^2$, $C{=}C(R^2)_2$, O, S, S=O, $SO_2$, $N(R^2)$, $P(R^2)$ and $P({=}O)R^2$;

$R^2$ is the same or different at each instance and is selected from the group consisting of H, D, F, CN, an aliphatic hydrocarbyl radical having 1 to 20 carbon atoms or an aromatic or heteroaromatic ring system which has 5 to 30 aromatic ring atoms and in which one or more hydrogen atoms may be replaced by D, F, Cl, Br, I or CN and which may be substituted by one or more alkyl groups each having 1 to 4 carbon atoms; at the same time, two or more, preferably adjacent substituents $R^2$ together may form a ring system.

In a preferred embodiment, it may be the case that compounds of formula A are excluded Formula (A)

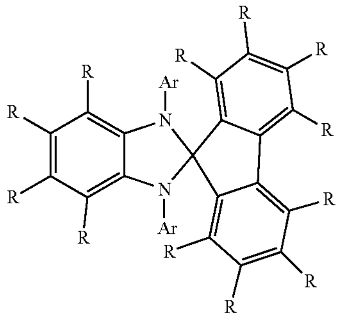

where the symbols Ar and R have the definition given above, especially for formula (I).

In a further-preferred embodiment, it may be the case that compounds of formula B are excluded Formula (B)

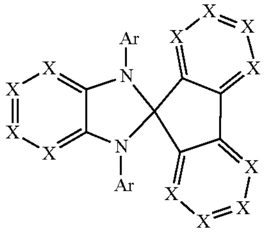

where the symbols Ar and X have the definition given above, especially for formula (I).

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused (annelated) aryl or heteroaryl group, for example naphthalene, anthracene, phenanthrene, quinoline, isoquinoline, etc. Aromatics joined to one another by a single bond, for example biphenyl, by contrast, are not referred to as an aryl or heteroaryl group but as an aromatic ring system.

An electron-deficient heteroaryl group in the context of the present invention is a heteroaryl group having at least one heteroaromatic six-membered ring having at least one nitrogen atom. Further aromatic or heteroaromatic five-membered or six-membered rings may be fused onto this six-membered ring. Examples of electron-deficient heteroaryl groups are pyridine, pyrimidine, pyrazine, pyridazine, triazine, quinoline, quinazoline or quinoxaline.

An aromatic ring system in the context of this invention contains 6 to 60 carbon atoms in the ring system. A heteroaromatic ring system in the context of this invention contains 2 to 60 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be joined by a non-aromatic unit, for example a carbon, nitrogen or oxygen atom. For example, systems such as fluorene, 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are joined, for example, by a short alkyl group. Preferably, the aromatic ring system is selected from fluorene, 9,9'-spirobifluorene, 9,9-diarylamine or groups in which two or more aryl and/or heteroaryl groups are joined to one another by single bonds.

In the context of the present invention, an aliphatic hydrocarbyl radical or an alkyl group or an alkenyl or alkynyl group which may contain 1 to 20 carbon atoms and in which individual hydrogen atoms or $CH_2$ groups may also be substituted by the abovementioned groups is preferably understood to mean the methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups according to the present invention may be straight-chain, branched or cyclic, where one or more non-adjacent $CH_2$ groups may be replaced by the abovementioned groups; in addition, it is also possible for one or more hydrogen atoms to be replaced by D, F, Cl, Br, I, CN or $NO_2$, preferably F, Cl or CN, further preferably F or CN, especially preferably CN.

An aromatic or heteroaromatic ring system which has 5-60 or 5-40 aromatic ring atoms and may also be substituted in each case by the abovementioned radicals and which may be joined to the aromatic or heteroaromatic system via any desired positions is understood to mean especially groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or groups derived from combinations of these systems.

The wording that two or more radicals together may form a ring, in the context of the present description, should be understood to mean, inter alia, that the two radicals are joined to one another by a chemical bond with formal elimination of two hydrogen atoms. This is illustrated by the following scheme:

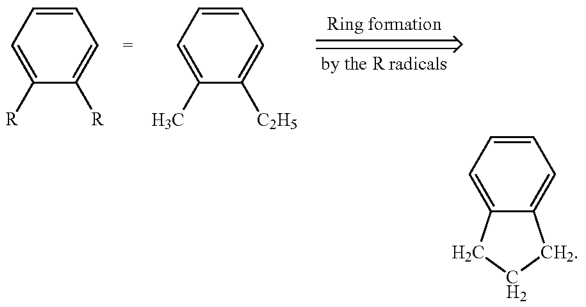

In addition, however, the abovementioned wording shall also be understood to mean that, if one of the two radicals is hydrogen, the second radical binds to the position to which the hydrogen atom was bonded, forming a ring. This will be illustrated by the following scheme:

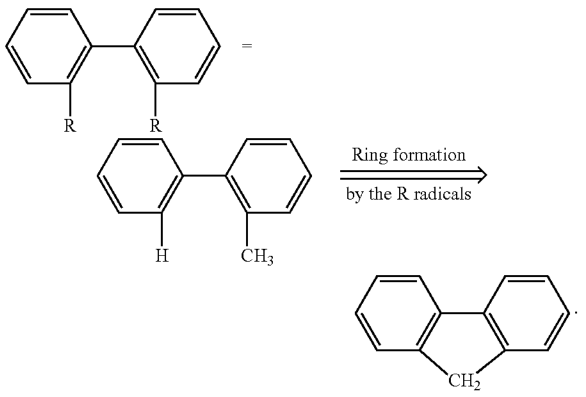

In a preferred configuration, the compounds of the invention may comprise a structure of the formulae (IIa), (IIb), (IIc) and (IId); more preferably, the compounds of the invention may be selected from the compounds of the formulae (IIa), (IIb), (IIc) and (IId):

Formula (IIa)

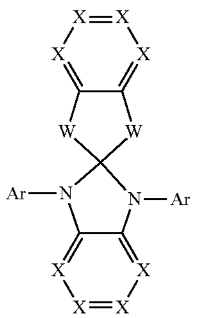

Formula (IIb)

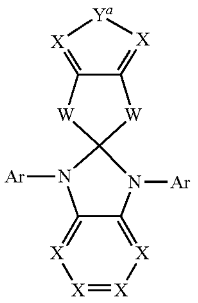

Formula (IIc)

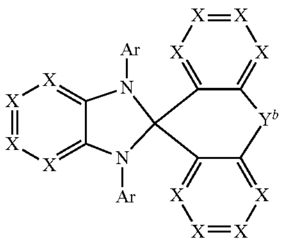

Formula (IId)

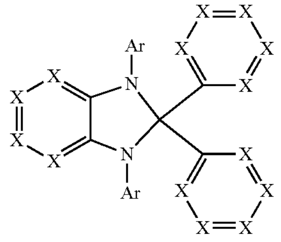

where X and Ar have the definitions given above, especially for formula (I), $Y^a$ is O, S, S=O, $SO_2$, N(R) or N(Ar'), $Y^b$ is B(R), $C(R)_2$, $Si(R)_2$, $Ge(R)_2$, C=O, C=NR, C=NAr', $C=C(R)_2$, O, S, S=O, $SO_2$, N(R), N(Ar'), P(R) or P(=O)R, preferably B(R), $C(R)_2$, $Si(R)_2$, $Ge(R)_2$, N(R), N(Ar'), O, S, S=O, $SO_2$, and W is the same or different at each instance and is N(Ar), NR, B(Ar), BR, O, S, P(=O)Ar, P(=O)R, S(=O), $S(=O)_2$. Preference is given here to structures/compounds of the formulae (IIa), (IIb) and (IIc), and particular preference to structures/compounds of the formulae (IIa) and (IIc).

It may preferably the case that, in the formulae (I), (IIa), (IIb), (IIc) and (IId), not more than four, preferably not more than two, X group(s) are N; more preferably, all X groups are CR or exactly two of the X groups are N and the rest of the X groups are CR. Especially preferred are compounds of the formulae (I), (IIa), (IIb), (IIc) and (IId), in which the X groups in the ortho position of the amino groups are N and the further X groups are CR.

In a further-preferred embodiment, it may be the case that the compounds of the invention comprise a structure of the formulae (IIIa), (IIIb), (IIIc), (IIId) and (IIIe), and are preferably selected from the compounds of the formulae (IIIa), (IIIb), (IIIc), (IIId) and (IIIe):

Formula (IIIa)

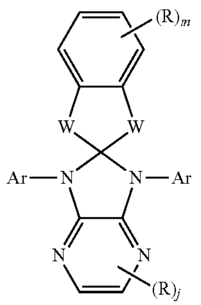

Formula (IIIb)

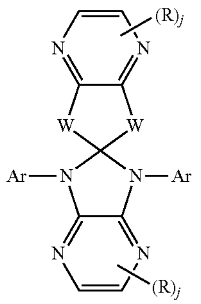

Formula (IIIc)

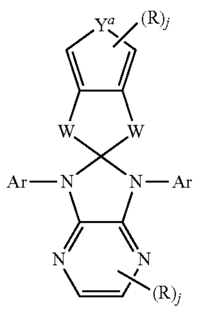

Formula (IIId)

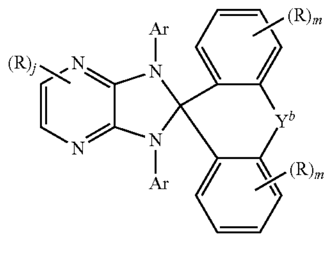

-continued

Formula (IIIe)

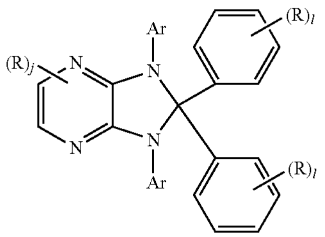

where R and Ar have the definitions given above, especially for formula (I), W, $Y^a$ and $Y^b$ have the definitions given above, especially for formulae (IIa) to (IId), the index l is 0, 1, 2, 3, 4 or 5, preferably 0, 1 or 2, the index m is 0, 1, 2, 3 or 4, preferably 0, 1 or 2, and the index j is 0, 1 or 2, preferably 0 or 1. Preference is given here to structures/compounds of the formulae (IIIa), (IIIb), (IIId) and (IIIe), and particular preference to structures/compounds of the formulae (IIIa), (IIId) and (IIIe).

In a further-preferred embodiment, it may be the case that the compounds of the invention comprise a structure of the formulae (IVa), (IVb), (IVc) and (IVd), and are preferably selected from the compounds of the formulae (IVa), (IVb), (IVc) and (IVd):

Formula (IVa)

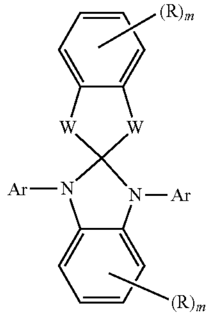

Formula (IVb)

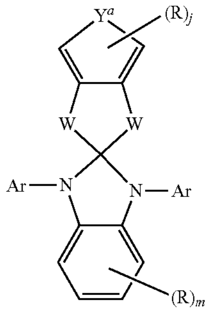

Formula (IVc)

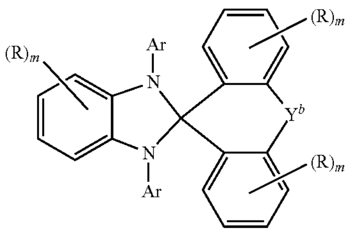

-continued

Formula (IVd)

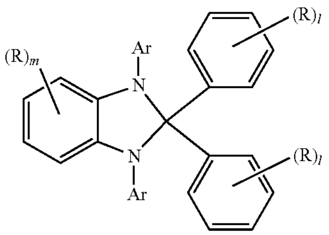

where R and Ar have the definitions given above, especially for formula (I), W, $Y^a$ and $Y^b$ have the definitions given above, especially for formulae (IIa) to (IId), the index l is 0, 1, 2, 3, 4 or 5, preferably 0, 1 or 2, the index m is 0, 1, 2, 3 or 4, preferably 0, 1 or 2, and the index j is 0, 1 or 2, preferably 0 or 1. Preference is given here to structures/compounds of the formulae (IVa), (IVc) and (IVd), and particular preference to structures/compounds of the formulae (IVa) and (IVc).

The sum total of the indices j, m and l in compounds of the formulae (IIIa) to (IIIe) and/or (IVa) to (IVd) is not more than 10, especially preferably not more than 8 and more preferably not more than 6.

It may preferably be the case, in formula (I), (IIa) to (IId), (IIIa) to (IIIe) and/or (IVa) to (IVd) inter alia, that the Ar group represents phenyl, biphenyl, terphenyl, quaterphenyl, fluorene, spirobifluorene, naphthalene, indole, benzofuran, benzothiophene, carbazole, dibenzofuran, dibenzothiophene, indenocarbazole, indolocarbazole, pyridine, pyrimidine, pyrazine, pyridazine, triazine, quinoline, isoquinoline, quinazoline, quinoxaline, phenanthrene or triphenylene, each of which may be substituted by one or more R radicals, preferably phenyl, biphenyl, fluorene, carbazole, dibenzofuran, dibenzothiophene.

More preferably, the compounds include at least one structure of the formulae (Va) to (Ve); preferably, the compounds are selected from the compounds of the formulae (Va) to (Ve):

Formula (Va)

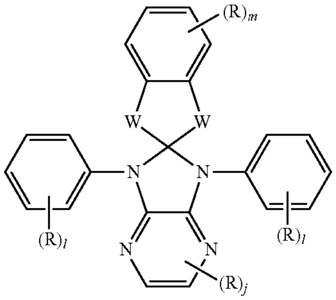

Formula (Vb)

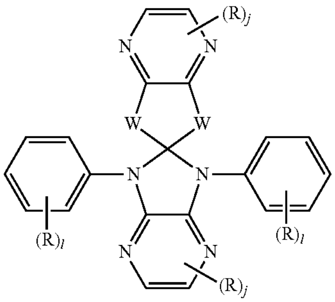

-continued

Formula (Vc)

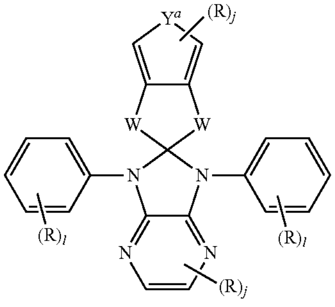

Formula (Vd)

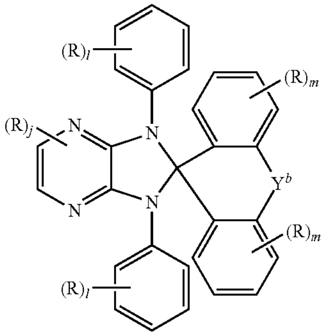

Formula (Ve)

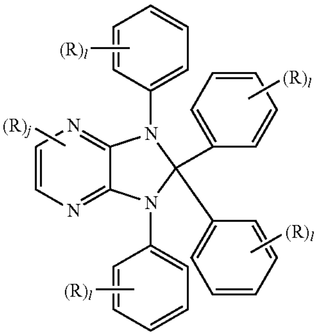

where R has the definitions given above, especially for formula (I), W, $Y^a$ and $Y^b$ have the definitions given above, especially for formulae (IIa) to (IIc), the index l is 0, 1, 2, 3, 4 or 5, preferably 0, 1 or 2, the index m is 0, 1, 2, 3 or 4, preferably 0, 1 or 2, and the index j is 0, 1 or 2, preferably 0 or 1. Preference is given here to structures/compounds of the formulae (Va), (Vb), (Vd) and (Ve), and particular preference to structures/compounds of the formulae (Va), (Vd) and (Ve).

More preferably, the compounds include at least one structure of the formulae (VIa) to (VId); more preferably, the compounds are selected from compounds of the formulae (VIa) to (VId), Formula (VIa)

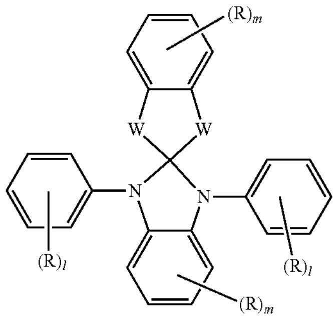

Formula (VIb)

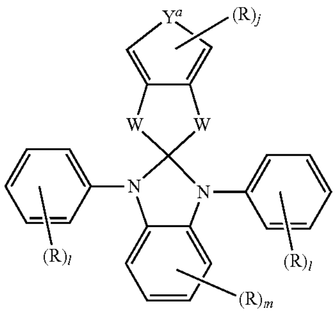

Formula (VIc)

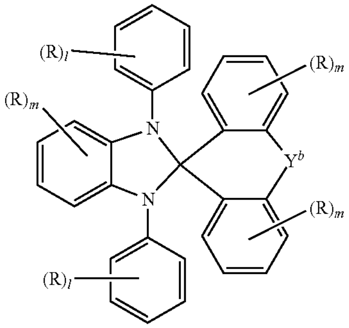

Formula (VId)

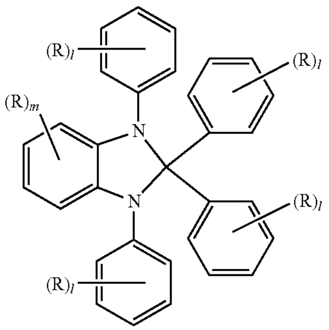

where R has the definitions given above, especially for formula (I), W, $Y^a$ and $Y^b$ have the definitions given above, especially for formulae (IIa) to (IIc), the index l is 0, 1, 2, 3, 4 or 5, preferably 0, 1 or 2, the index m is 0, 1, 2, 3 or 4, preferably 0, 1 or 2, and the index j is 0, 1 or 2, preferably 0 or 1. Preference is given here to structures/compounds of the formulae (VIa), (VIc) and (VId), and particular preference to structures/compounds of the formulae (VIa) and (VIc).

In the formulae (Va) to (Ve) and/or (VIa) to (VId), the sum total of the indices j, l and m is preferably not more than 10, preferably not more than 8 and more preferably not more than 6.

It may further be the case that, in the formulae shown above and hereinafter that include W, at least one of the W radicals represents N(R) or N(Ar), preferably N(Ar). In a further-preferred embodiment, the two W radicals represent N(R) or N(Ar), preferably N(Ar).

It may additionally be the case that, in the formulae shown above and hereinafter that include W, at least one of the W radicals represents B(R) or B(Ar), preferably B(Ar). In a further-preferred embodiment, the two W radicals represent B(R) or B(Ar), preferably B(Ar).

In a further embodiment, it may be the case that, in the formulae shown above and hereinafter that include W, at least one of the W radicals represents O, S, S(=O), $S(=O)_2$. In a further-preferred embodiment, both W radicals represent O, S, S(=O), $S(=O)_2$.

It may further be the case that both W radicals are the same. In this context, the expression "the same" means that the R or Ar radicals are indistinguishable.

In a further embodiment, it may be the case that the W radicals are different. Preferably, at least one of the W radicals represents N(R) or N(Ar), preferably N(Ar), and at least one of the W radicals is B(Ar), B(R), O or S.

In a further-preferred embodiment, it may be the case that the compounds of the invention comprise a structure of the formulae (Va-1) to (Vb-11), where the compounds of the invention may more preferably be selected from the compounds of the formulae (Vb-1) to (Vb-11), Formula (Va-1)

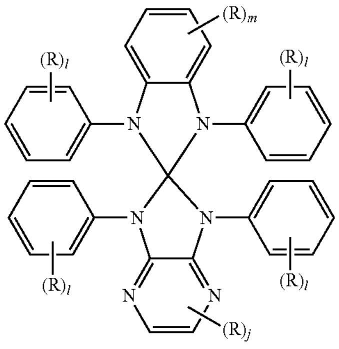

Formula (Vb-1)

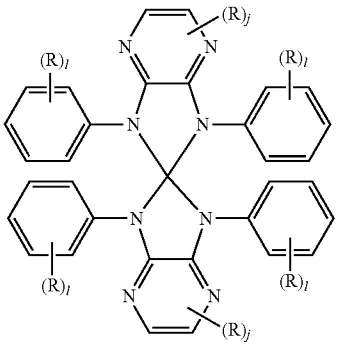

-continued

Formula (Va-2)

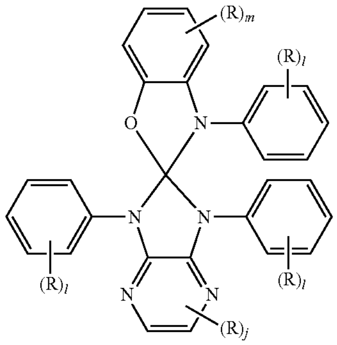

Formula (Vb-2)

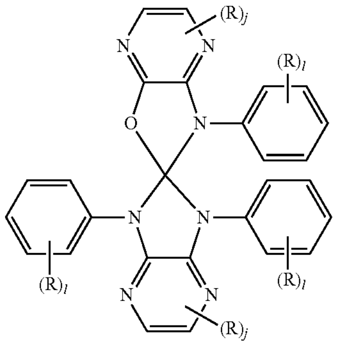

Formula (Va-3)

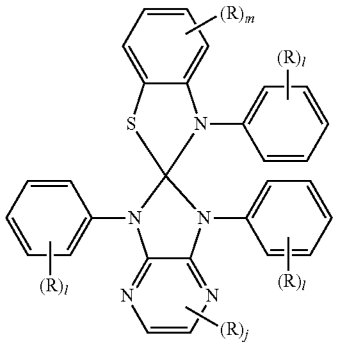

Formula (Vb-3)

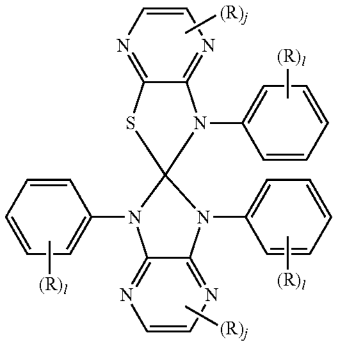

-continued
Formula (Va-4)
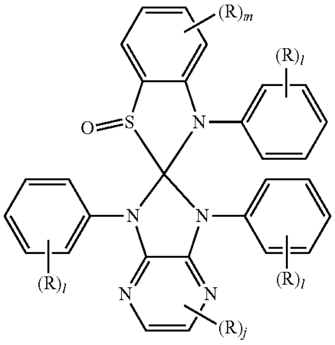
Formula (Vb-4)
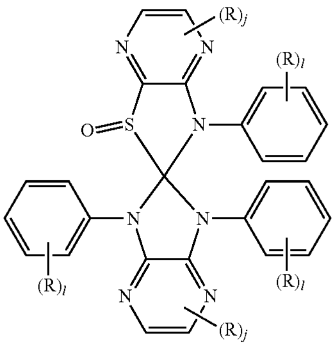
Formula (Va-5)
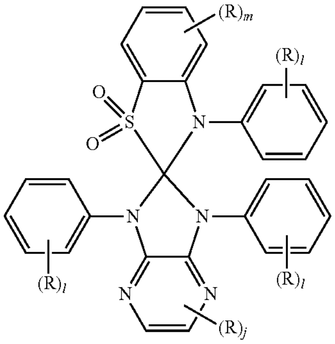
Formula (Vb-5)
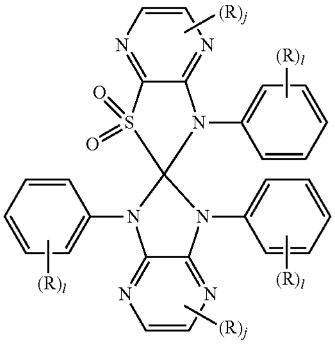
-continued
Formula (Va-6)
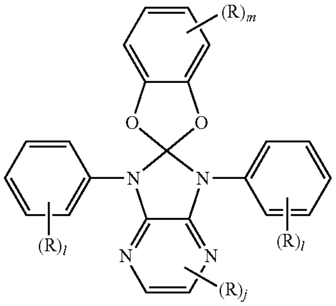
Formula (Vb-6)
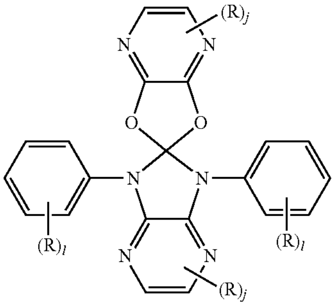
Formula (Va-7)
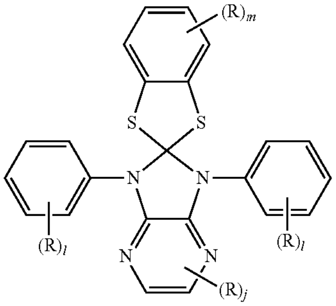
Formula (Vb-7)
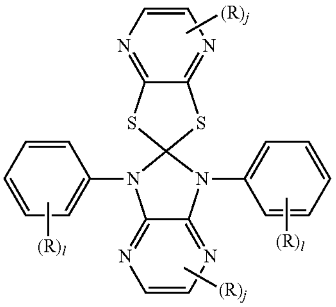
Formula (Va-8)
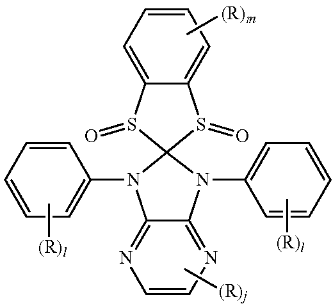

-continued

Formula (Vb-8)

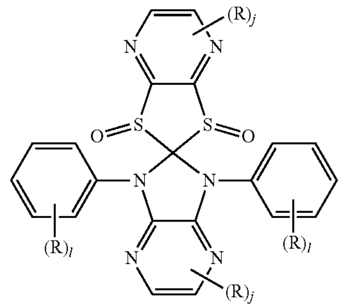

Formula (Va-9)

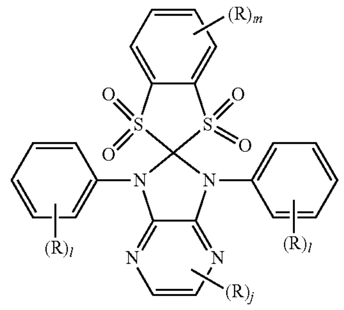

Formula (Vb-9)

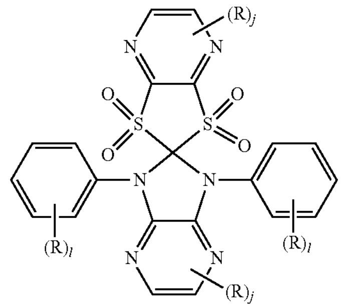

Formula (Va-10)

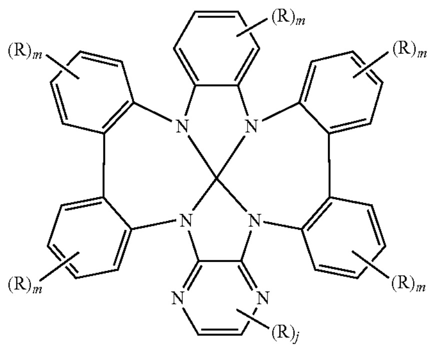

-continued

Formula (Vb-10)

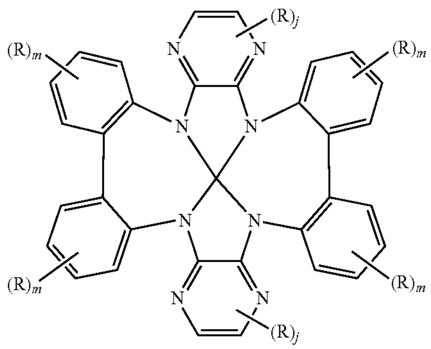

Formula (Va-11)

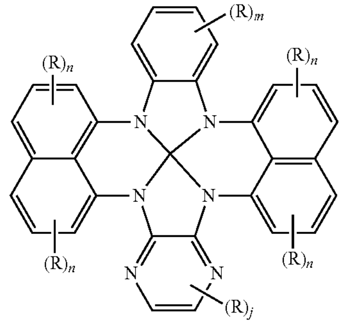

Formula (Vb-11)

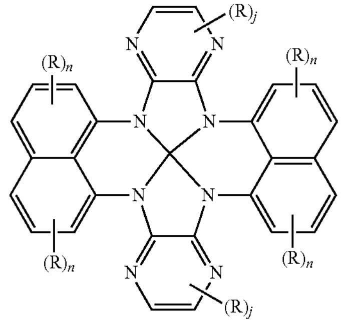

Formula (Va-12)

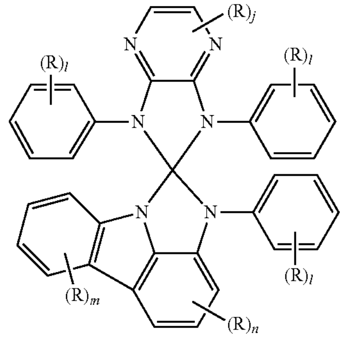

where R has the definitions given above, especially for formula (I), the index l is 0, 1, 2, 3, 4 or 5, preferably 0, 1 or 2, the index m is 0, 1, 2, 3 or 4, preferably 0, 1 or 2, the index n is 0, 1, 2 or 3, preferably 0, 1 or 2, and the index j is 0, 1 or 2, preferably 0 or 1.

In a further preferred configuration, it may be the case that the compounds of the invention comprise a structure of the formulae (Vc-1) to (Vc-11), where the compounds of the invention may more preferably be selected from the compounds of the formulae (Vc-1) to (Vc-11):

Formula (Vc-1)
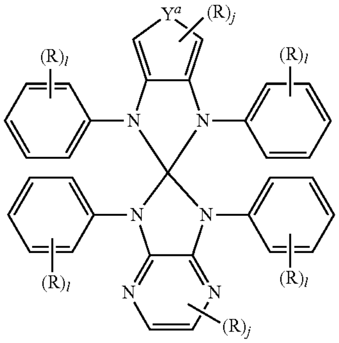
Formula (Vc-2)
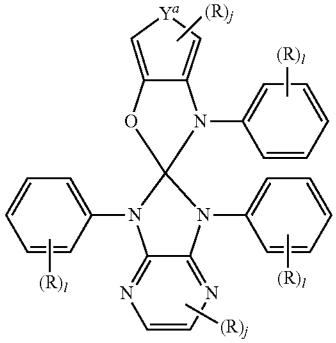
Formula (Vc-3)
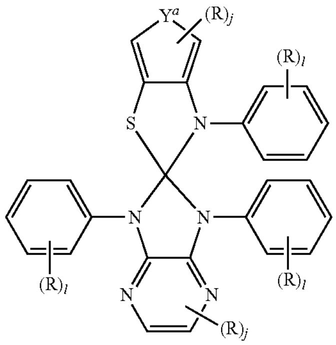
Formula (Vc-4)
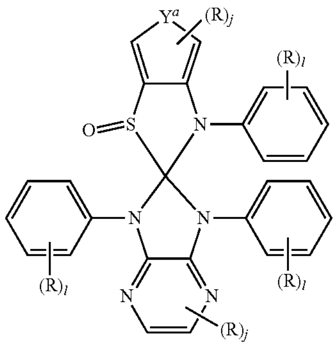
-continued
Formula (Vc-5)
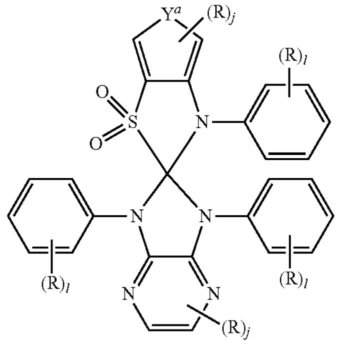
Formula (Vc-6)
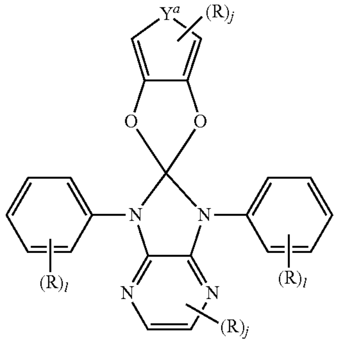
Formula (Vc-7)
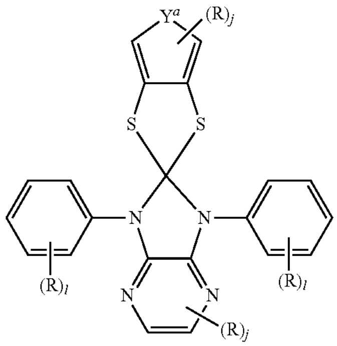
Formula (Vc-8)
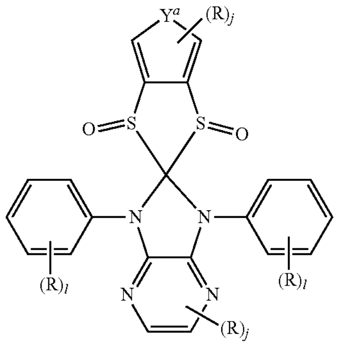

-continued

Formula (Vc-9)

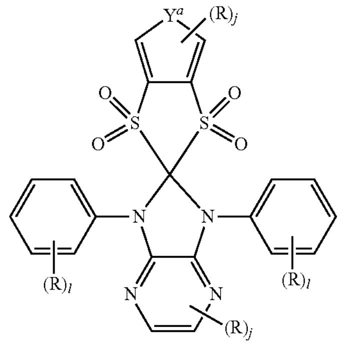

Formula (Vc-10)

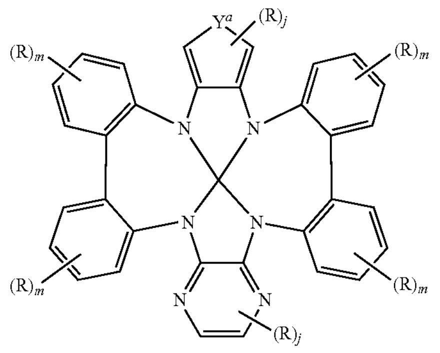

Formula (Vc-11)

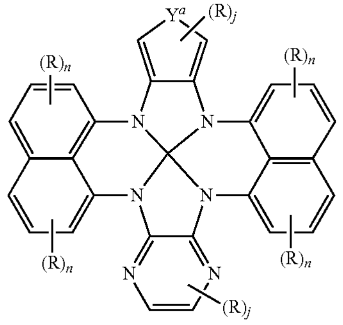

where R has the definitions given above, especially for formula (I), $Y^a$ has the definitions given above, especially for formula (IIc), the index l is 0, 1, 2, 3, 4 or 5, preferably 0, 1 or 2, the index m is 0, 1, 2, 3 or 4, preferably 0, 1 or 2, the index n is 0, 1, 2 or 3, preferably 0, 1 or 2, and the index j is 0, 1 or 2, preferably 0 or 1.

In a further-preferred embodiment, it may be the case that the compounds of the invention comprise a structure of the formulae (VIa-1) to (VIb-13), where the compounds of the invention may more preferably be selected from the compounds of the formulae (VIa-1) to (VIb-13):

Formula (VIa-1)

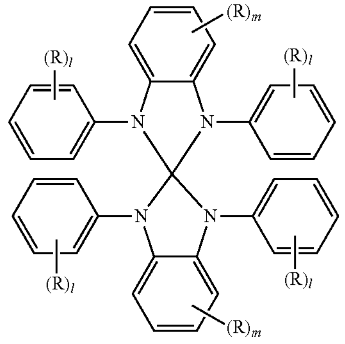

Formula (VIb-1)

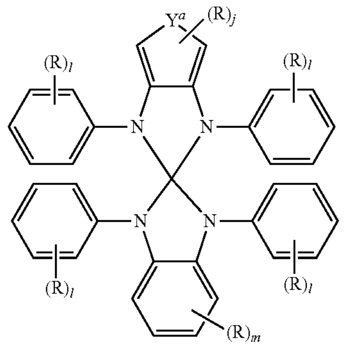

Formula (VIa-2)

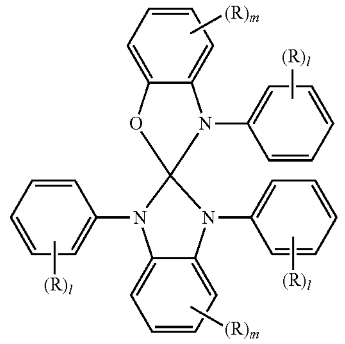

Formula (VIb-2)

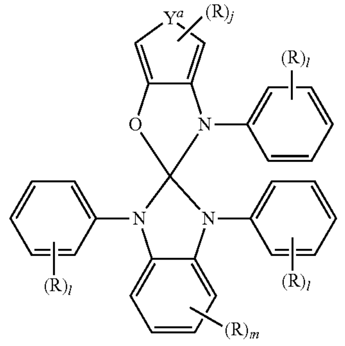

-continued
Formula (VIa-3)
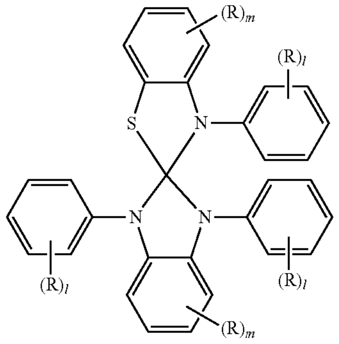
Formula (VIb-3)
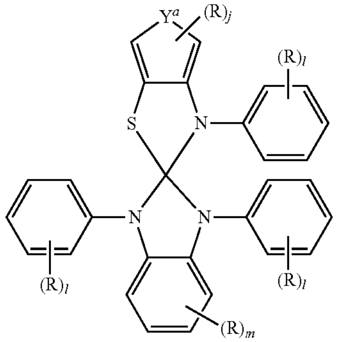
Formula (VIa-4)
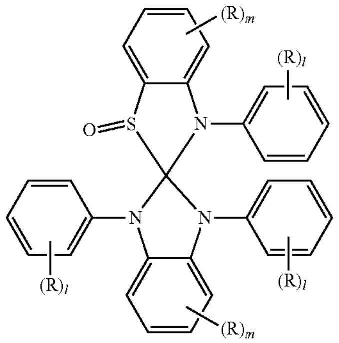
Formula (VIb-3)
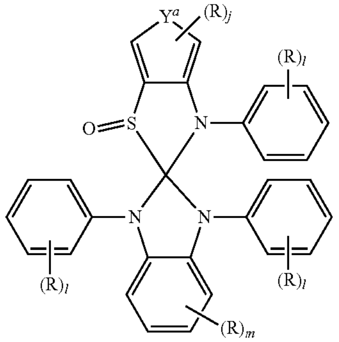
-continued
Formula (VIa-5)
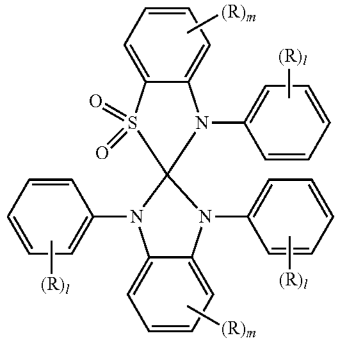
Formula (VIb-5)
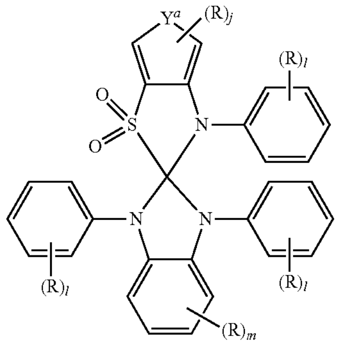
Formula (VIa-6)
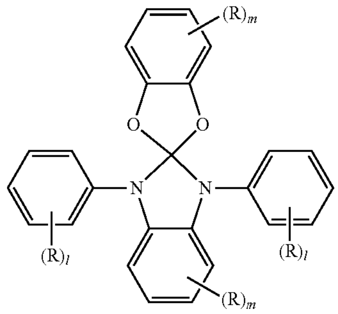
Formula (VIb-6)
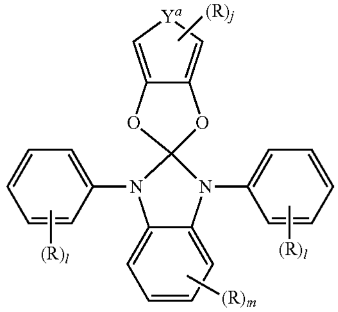
Formula (VIa-7)
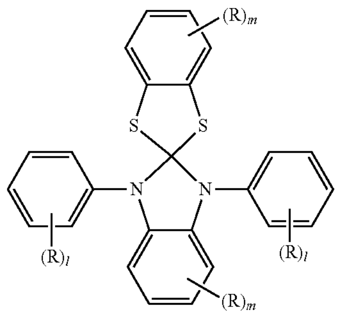

-continued
Formula (VIb-7)
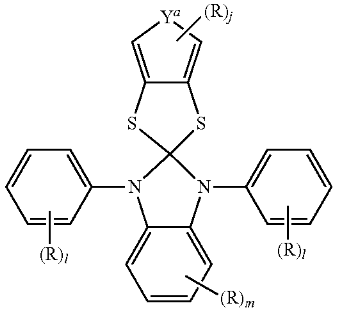
Formula (VIa-8)
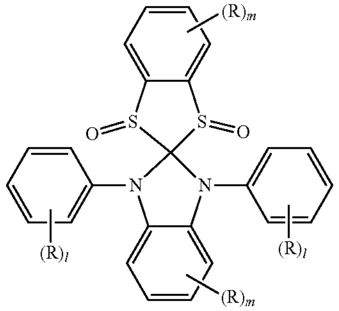
Formula (VIb-8)
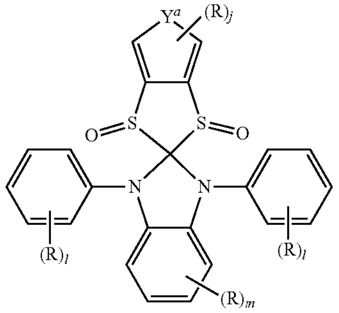
Formula (VIa-9)
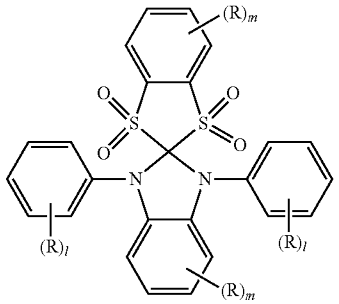
Formula (VIb-9)
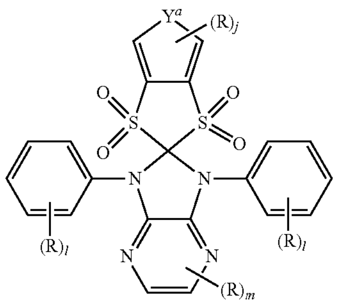
-continued
Formula (VIa-10)
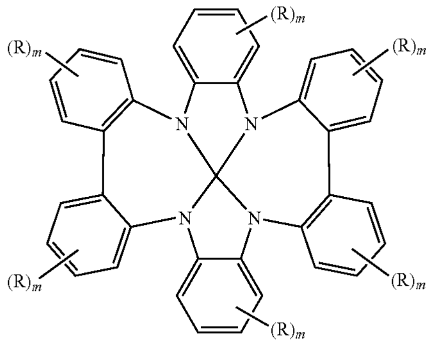
Formula (VIb-10)
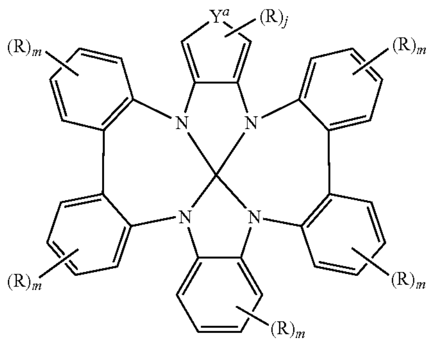
Formula (VIa-11)
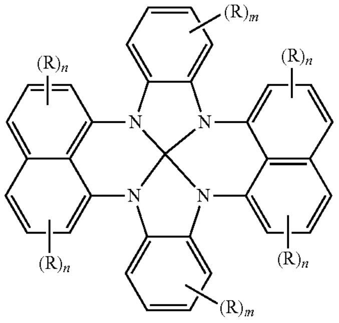
Formula (VIb-11)
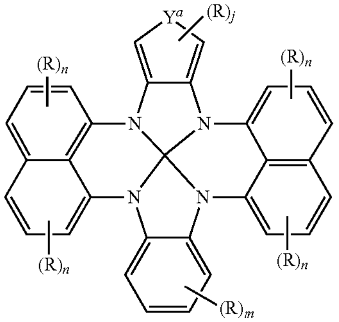

-continued

Formula (VIa-12)

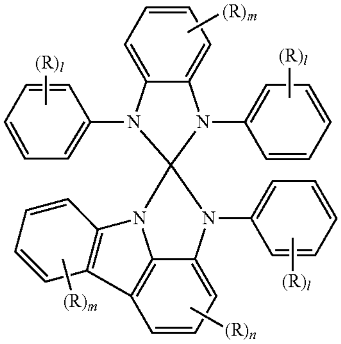

Formula (VIb-12)

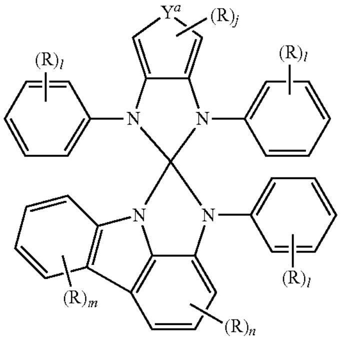

Formula (VIa-13)

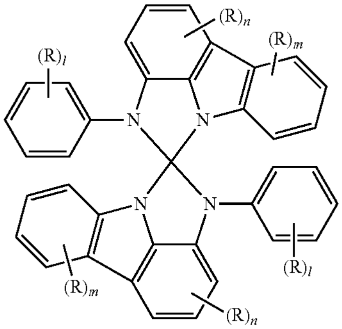

Formula (VIb-13)

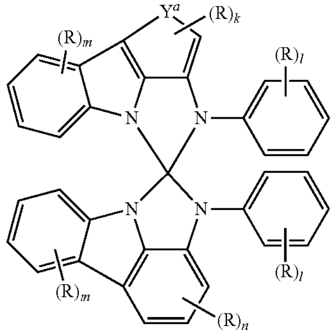

where R has the definitions given above, especially for formula (I), $Y^a$ has the definitions given above, especially for formula (IIc), the index l is 0, 1, 2, 3, 4 or 5, preferably 0, 1 or 2, the index m is 0, 1, 2, 3 or 4, preferably 0, 1 or 2, the index n is 0, 1, 2 or 3, preferably 0, 1 or 2, and the index j is 0, 1 or 2, preferably 0 or 1. Preference is given here to structures/compounds of the formulae (VIa-1), (VIa-2), (VIa-3), (VIb-1), (VIa-12) and (VIa-13), and particular preference to structures/compounds of the formulae (VIa-1) and (VIa-3).

In the formulae (Va-1) to (Va-12), (Vb-1) to (Vb-11), (Vc-1) to (Vc-11), (VIa-1) to (VIa-13) and/or (VIb-1) to (VIb-13), the sum total of the indices j, l and m is not more than 10, preferably not more than 8 and more preferably not more than 6.

In a preferred development of the present invention, it may be the case that at least two R radicals form a fused ring together with the further groups to which the two R radicals bind, where the two R radicals form at least one structure of the formulae (RA-1) to (RA-12):

Formula RA-1

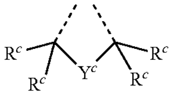

Formula RA-2

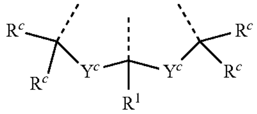

Formula RA-3

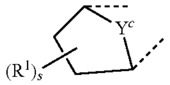

Formula RA-4

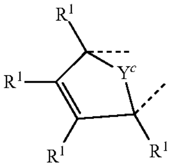

Formula RA-5

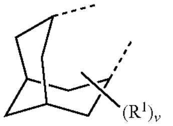

Formula RA-6

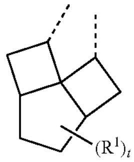

Formula RA-7

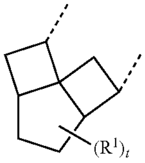

Formula RA-8

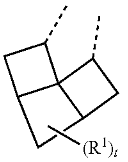

Formula RA-9

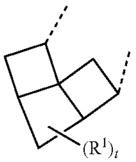

-continued

Formula RA-10

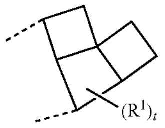

Formula RA-11

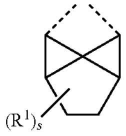

Formula RA-12

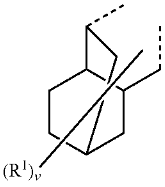

where $R^1$ has the definition set out above, especially for formula (I), the dotted bonds represent the sites of attachment to the atoms of the groups to which the two R radicals bind, and the further symbols have the following definition:

$Y^c$ is the same or different at each instance and is $C(R^1)_2$, $(R^1)_2C—C(R^1)_2$, $(R^1)C═C(R^1)$, $NR^1$, NAr', O or S, preferably $C(R^1)_2$, $(R^1)_2C—C(R^1)_2$, $(R^1)C═C(R^1)$, O or S, where Ar' has the definition detailed above;

$R^c$ is the same or different at each instance and is F, a straight-chain alkyl, alkoxy or thioalkoxy group having 1 to 40 carbon atoms or an alkyl or alkenyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may be substituted in each case by one or more $R^2$ radicals, where one or more adjacent $CH_2$ groups may be replaced by $R^2C═CR^2$, C≡C, $Si(R^2)_2$, C═O, C═S, C═Se, $C═NR^2$, —C(═O)O—, $—C(═O)NR^2—$, $NR^2$, $P(═O)(R^2)$, —O—, —S—, SO or $SO_2$, or an aromatic or heteroaromatic ring system which has 5 to 60 aromatic ring atoms and may be substituted in each case by one or more $R^2$ radicals, or an aryloxy or heteroaryloxy group which has 5 to 60 aromatic ring atoms and may be substituted by one or more $R^2$ radicals, where $R^2$ has the definition detailed above; at the same time, it is also possible for two $R^c$ radicals together to form a ring system;

s is 0, 1, 2, 3, 4, 5 or 6, preferably 0, 1, 2, 3 or 4, more preferably 0, 1 or 2;

t is 0, 1, 2, 3, 4, 5, 6, 7 or 8, preferably 0, 1, 2, 3 or 4, more preferably 0, 1 or 2;

v is 0, 1, 2, 3, 4, 5, 6, 7, 8 or 9, preferably 0, 1, 2, 3 or 4, more preferably 0, 1 or 2.

It may further be the case that the at least two R radicals that form structures of the formulae (RA-1) to (RA-12) and form a condensed ring are R radicals from adjacent X groups.

In a preferred embodiment of the invention, at least two R radicals form a fused ring together with the further groups to which the two R radicals bind, where the two R radicals preferably form at least one of the structures of the formulae (RA-1a) to (RA-4f):

Formula RA-1a

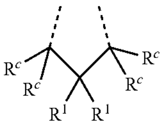

Formula RA-1b

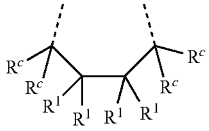

Formula RA-1c

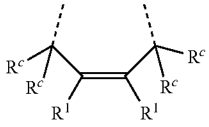

Formula RA-2a

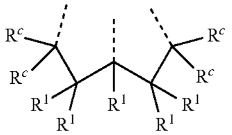

Formula RA-2b

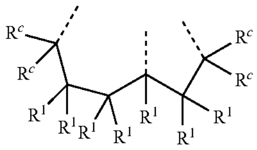

Formula RA-2c

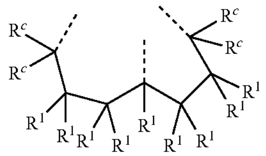

Formula RA-3a

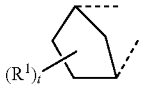

Formula RA-3b

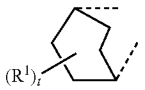

Formula RA-4a

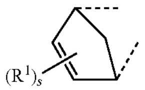

Formula RA-4b

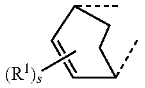

Formula RA-4c

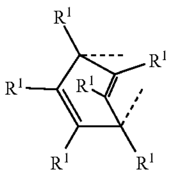

-continued

Formula RA-4d

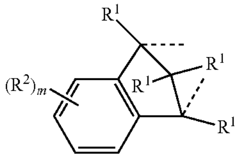

Formula RA-4e

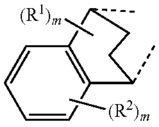

Formula RA-4f

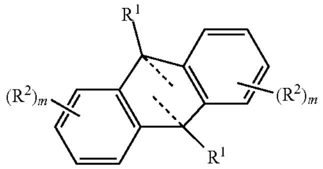

where the symbols $R^1$, $R^2$, R and the indices s and t have the definitions given above, especially for formulae (RA-1) to (RA-12), and the index m is 0, 1, 2, 3 or 4, preferably 0, 1 or 2.

In a further-preferred configuration, at least two R radicals form a fused ring together with the further groups to which the two R radicals bind, where the two R radicals form structures of the formula (RB):

Formula RB

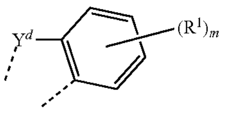

where $R^1$ has the definition set out above, especially for formula (I), the index m is 0, 1, 2, 3 or 4, preferably 0, 1 or 2, and $Y^d$ is $C(R^1)_2$, $N(R^1)$, N(Ar'), $B(R^1)$, B(Ar'), O or S, preferably $C(R^1)_2$, N(Ar') or O, where Ar' has the definition detailed above.

It may be the case here that the at least two R radicals that form structures of the formula (RB) and form a condensed ring are R radicals from adjacent X groups.

More preferably, the compounds include at least one structure of the formulae (VIIa) to (VIIj); more preferably, the compounds are selected from compounds of the formulae (VIIa) to (VIIj), where the compounds have at least one fused ring:

Formula (VIIa)

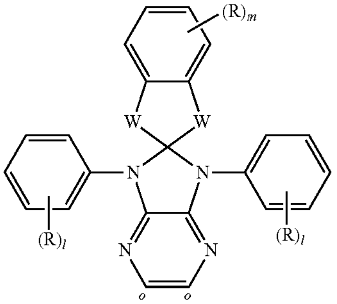

-continued

Formula (VIIb)

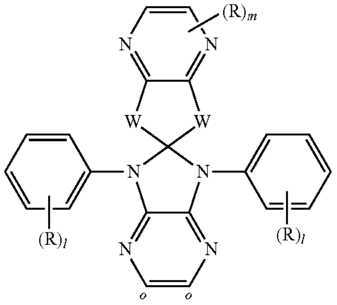

Formula (VIIc)

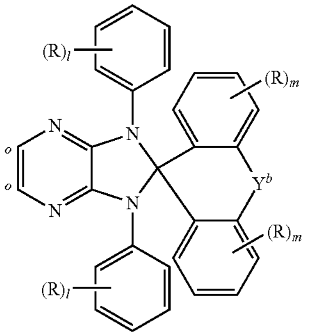

Formula (VIId)

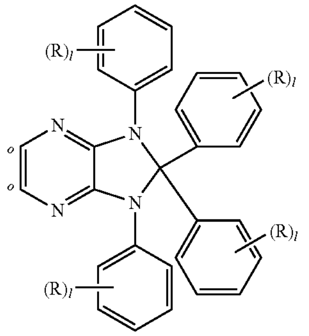

Formula (VIIe)

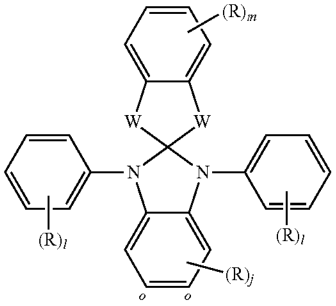

Formula (VIIf)

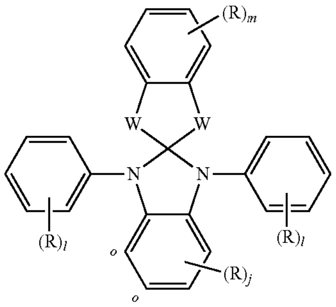

-continued

Formula (VIIg)

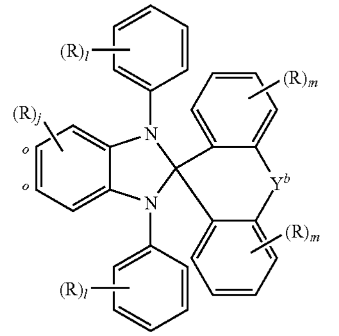

Formula (VIIh)

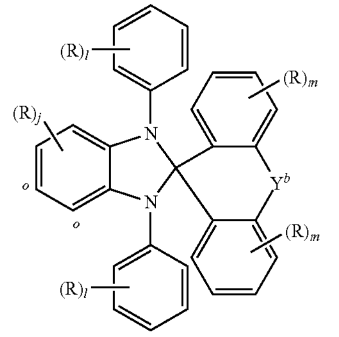

Formula (VIIi)

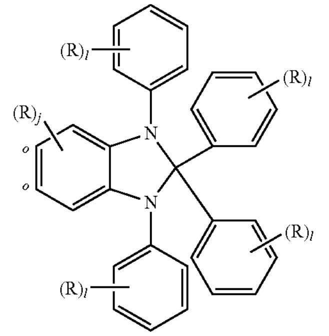

Formula (VIIj)

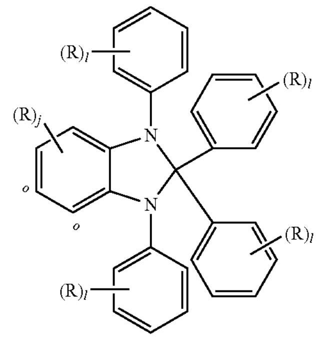

where R has the definitions given above, especially for formula (I), W, $Y^a$ and $Y^b$ have the definitions given above, especially for formulae (IIa) to (IIc), the symbol o represents the sites of attachment of the fused ring, the index l is 0, 1, 2, 3, 4 or 5, preferably 0, 1 or 2, the index m is 0, 1, 2, 3 or 4, preferably 0, 1 or 2, the index n is 0, 1, 2 or 3, preferably 0, 1 or 2, and the index j is 0, 1 or 2, preferably 0 or 1, where the sum total of the indices k, j, l, m and n is preferably 0, 1, 2, 3, 4, 5 or 6. Preference is given here to structures/compounds of the formulae (VIIa) to (IVh), and particular preference to structures/compounds of the formula (VIIa) and (VIIe).

The fused ring, especially in formulae (VIIa) to (VIIj), is preferably formed by at least one of the structures of the formulae (RA-1) to (RA-12), of the formulae (RA-1a) to (RA-4f) and/or of the formula (RB), together with the ring atoms marked by the symbol o, particular preference being given to structures of the formulae (RA-1) to (RA-12), of the formulae (RA-1a) to (RA-4f) and/or of the formula (RB) with Y═N(Ar') or O, more preferably $Y^d$ ═N(Ar'), where Ar' has the definition given above, especially formula (I).

It may be the case here that the compounds of the invention have at least two fused rings, where the fused rings are the same and the moiety formed by two R radicals can be represented by at least one structure of the formulae (RA-1) to (RA-12).

It may further be the case that the compounds of the invention have at least two fused rings, where the fused rings are different and the moiety formed by two R radicals can be represented in each case by at least one structure of the formulae (RA-1) to (RA-12).

It may additionally be the case that the compounds of the invention have at least two fused rings, where the fused rings are different and one of the two fused rings has a moiety formed by two R radicals that can be represented by at least one of the structures of the formulae (RA-1) to (RA-12), and one of the two fused rings has a moiety formed by two R radicals that can be represented by one of the structures of the formula (RB).

It may also be the case that the substituents R and $R^c$, $R^1$ and $R^2$ of the above formulae do not form a fused aromatic or heteroaromatic ring system with the ring atoms of the ring system to which R and $R^c$, $R^1$ and $R^2$ bind. This includes the formation of a fused aromatic or heteroaromatic ring system with possible substituents $R^1$ and $R^2$ which may be bonded to the R, $R^c$ and $R^1$ radicals. It may further be the case that the substituents R and $R^c$, $R^1$ and $R^2$ according to the above formulae do not form a fused ring system with the ring atoms of the ring system to which the R and $R^c$, $R^1$ and $R^2$ bind, apart from ring systems of the formula (RA-1) to (RA-12) and preferred embodiments of these ring systems, or ring systems of the formula (RB). This includes the formation of a fused ring system with possible substituents $R^1$ and $R^2$ which may be bonded to the R, $R^c$ and $R^1$ radicals.

When two radicals that may especially be selected from R, $R^c$, $R^1$ and/or $R^2$ form a ring system with one another, this ring system may be mono- or polycyclic, aliphatic, heteroaliphatic, aromatic or heteroaromatic. In this case, the radicals which together form a ring system may be adjacent, meaning that these radicals are bonded to the same carbon atom or to carbon atoms directly bonded to one another, or they may be further removed from one another. In addition, the ring systems provided with the substituents R, $R^c$, $R^1$ and/or $R^2$ may also be joined to one another via a bond, such that this can bring about a ring closure. In this case, each of the corresponding bonding sites has preferably been provided with a substituent R, $R^c$, $R^1$ and/or $R^2$.

In a preferred configuration, a compound of the invention can be represented by at least one of the structures of formula (I), (IIa) to (IId), (IIIa) to (IIIe), (IVa) to (IVd), (Va) to (Ve), (VIa) to (VId) and/or the preferred embodiments thereof. Preferably, compounds of the invention, preferably comprising structures of formula (I), (IIa) to (IId), (IIIa) to (IIIe), (IVa) to (IVd), (Va) to (Ve), (VIa) to (VId) and/or the preferred embodiments thereof have a molecular weight of not more than 5000 g/mol, preferably not more than 4000 g/mol, particularly preferably not more than 3000 g/mol, especially preferably not more than 2000 g/mol and most preferably not more than 1200 g/mol.

In addition, it is a feature of preferred compounds of the invention that they are sublimable. These compounds generally have a molar mass of less than about 1200 g/mol.

Preferred aromatic or heteroaromatic ring systems Ar, R and/or Ar' are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene, especially 1- or 2-bonded naphthalene, indole, benzofuran, benzothiophene, carbazole which may be joined via the 1, 2, 3 or 4 position, dibenzofuran which may be joined via the 1, 2, 3 or 4 position, dibenzothiophene which may be joined via the 1, 2, 3 or 4 position, indenocarbazole, indolocarbazole, pyridine, pyrimidine, pyrazine, pyridazine, triazine, quinoline, isoquinoline, quinazoline, quinoxaline, phenanthrene or triphenylene, each of which may be substituted by one or more $R^1$ radicals.

Preferably, at least one substituent R is the same or different at each instance and is selected from the group consisting of H, D or an aromatic or heteroaromatic ring system selected from the groups of the following formulae Ar-1 to Ar-75, where the substituents R preferably either form a ring according to the structures of the formulae (RA-1) to (RA-12) or (RB) or the substituent R is the same or different at each instance and is selected from the group consisting of H, D or an aromatic heteroaromatic ring system selected from the groups of the following formulae Ar-1 to Ar-75, and/or the Ar group is the same or different at each instance and is selected from the groups of the following formulae Ar-1 to Ar-75:

Ar-1

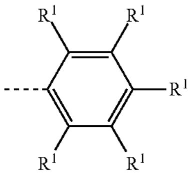

Ar-2

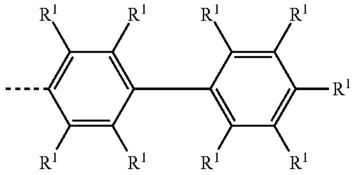

Ar-3

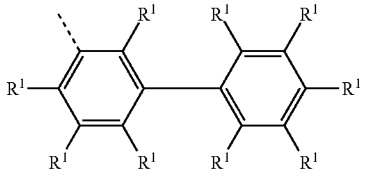

Ar-4

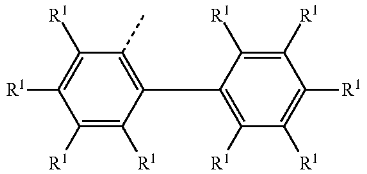

-continued

Ar-5

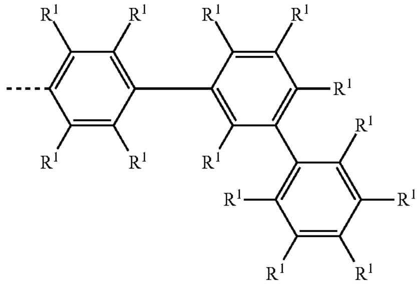

Ar-6

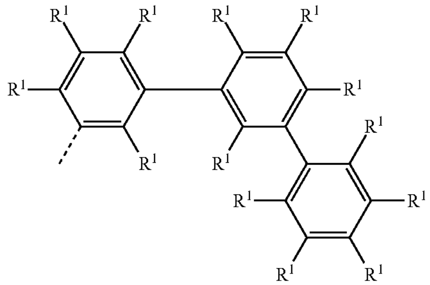

Ar-7

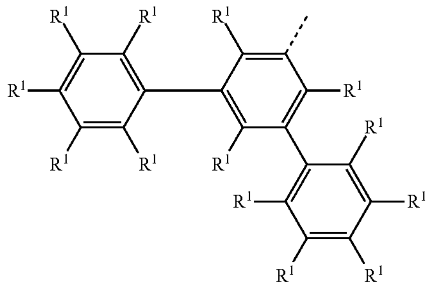

Ar-8

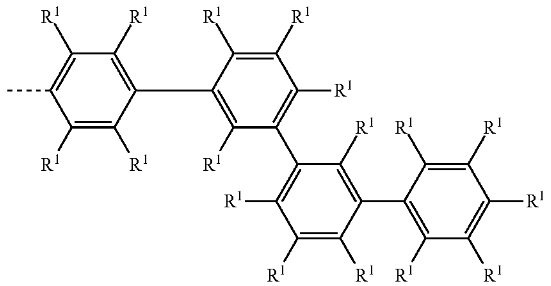

Ar-9

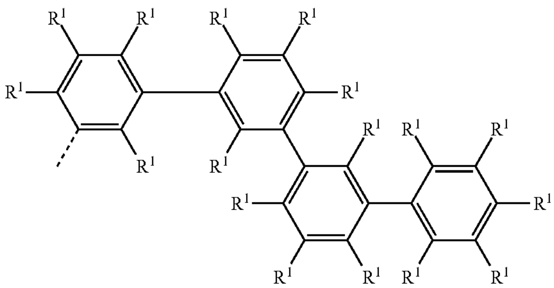

-continued
Ar-10
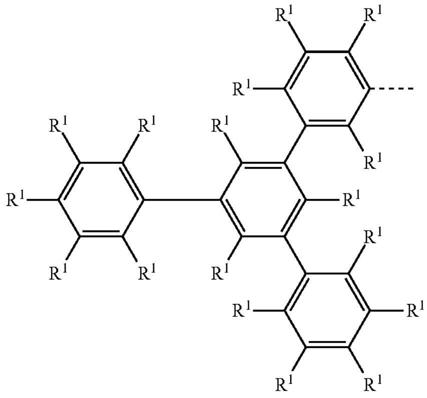
Ar-11
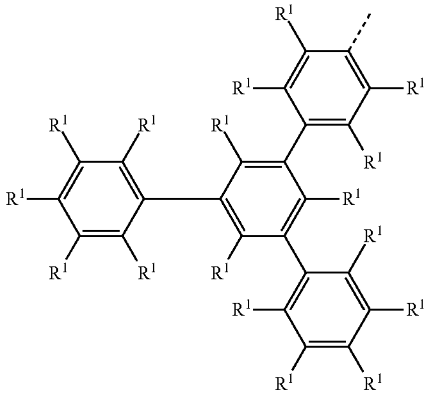
Ar-12
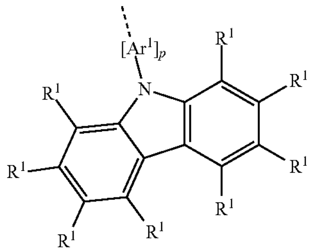
Ar-13
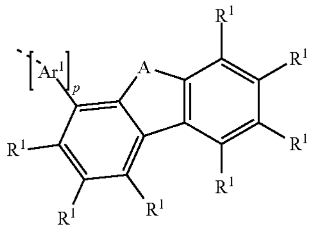
Ar-14
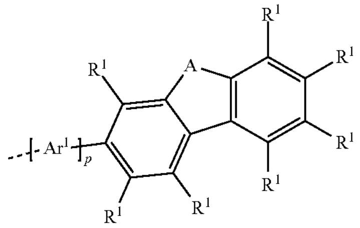
-continued
Ar-15
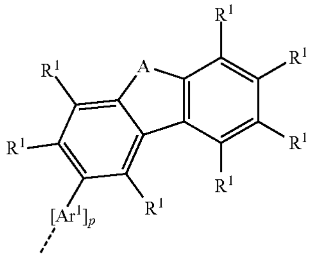
Ar-16
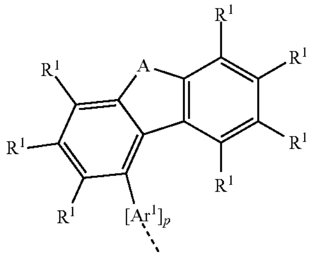
Ar-17
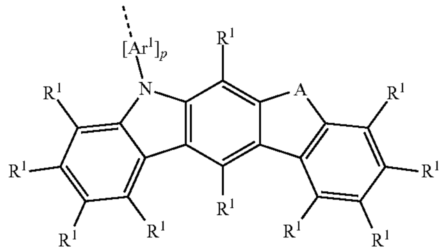
Ar-18
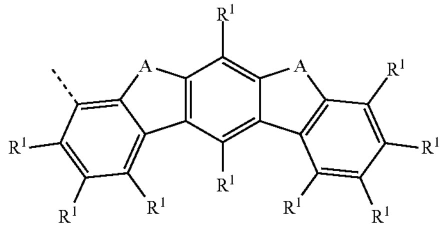
Ar-19
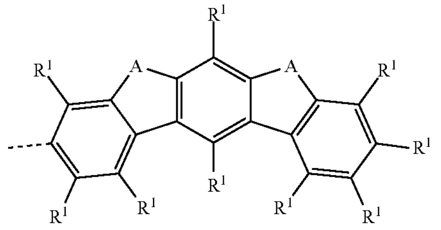
Ar-20
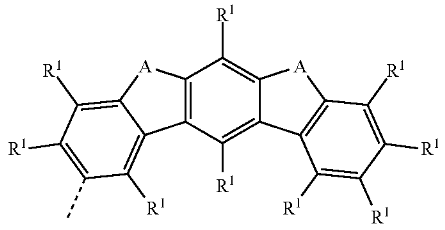

-continued
Ar-21
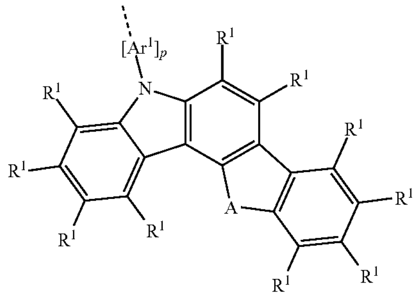
Ar-22
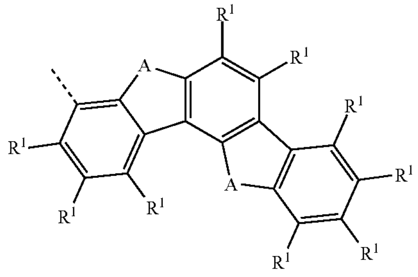
Ar-23
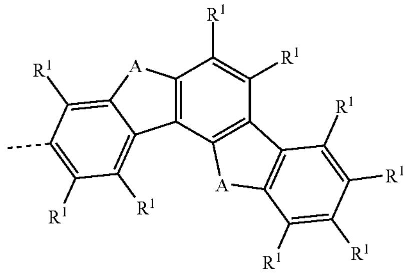
Ar-24
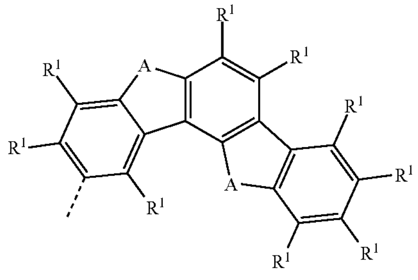
Ar-25
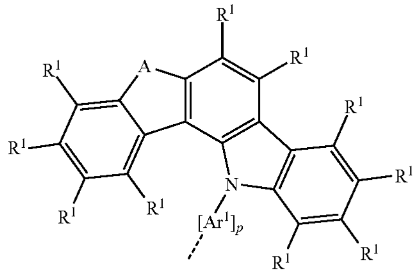
-continued
Ar-26
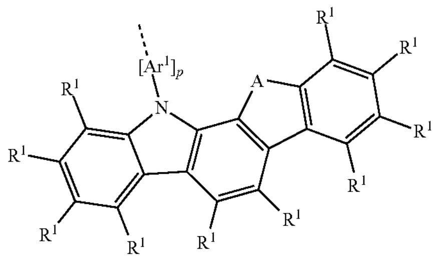
Ar-27
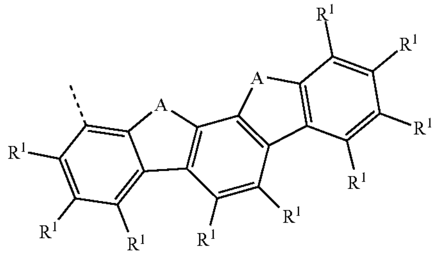
Ar-28
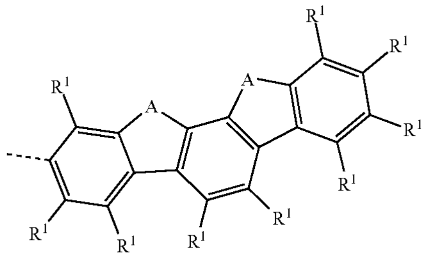
Ar-29
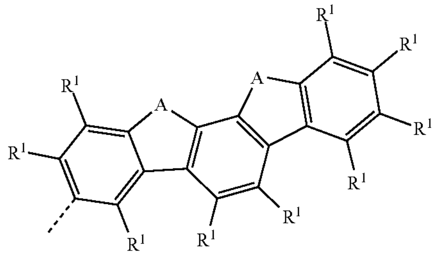
Ar-30
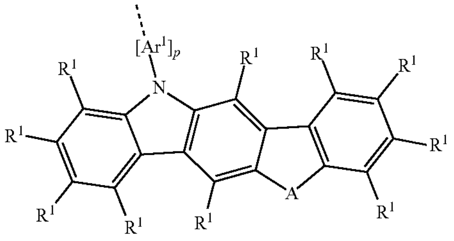
Ar-31
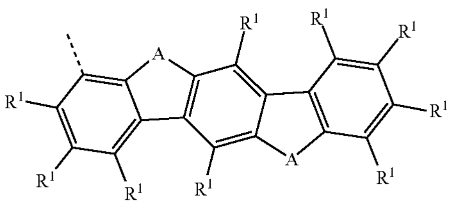

Ar-32
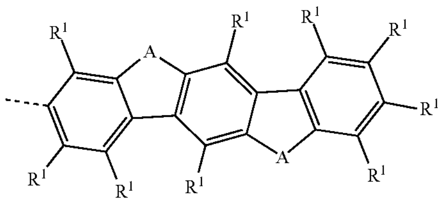
Ar-33
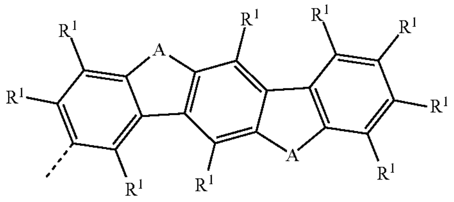
Ar-34
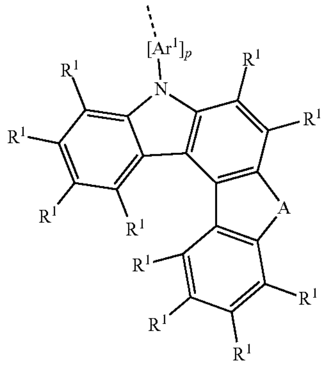
Ar-35
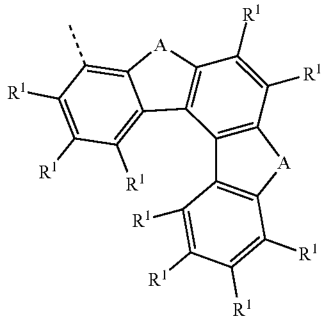
Ar-36
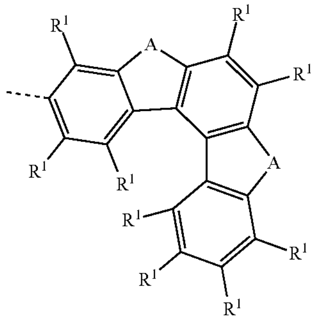
Ar-37
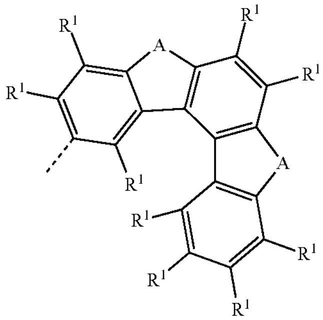
Ar-38
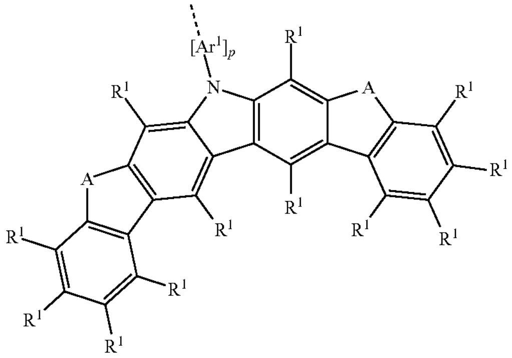
Ar-39
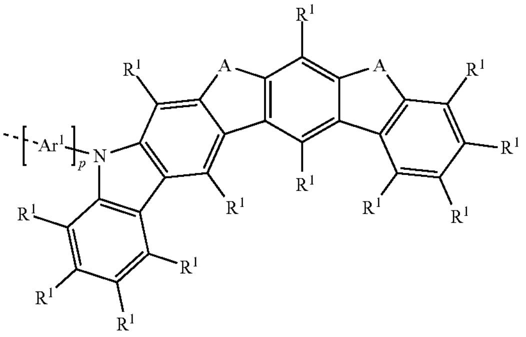
Ar-40
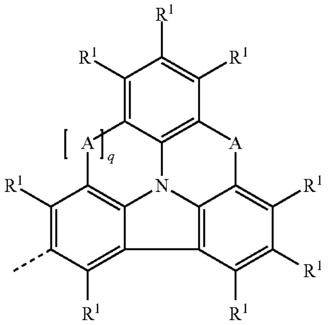

-continued
Ar-41
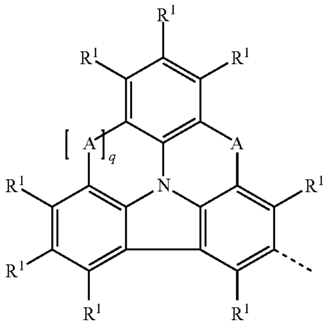
Ar-42
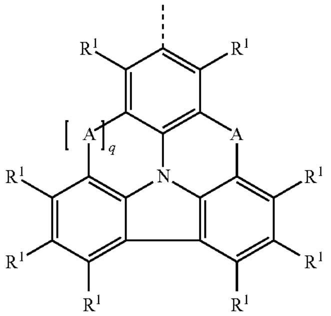
Ar-43
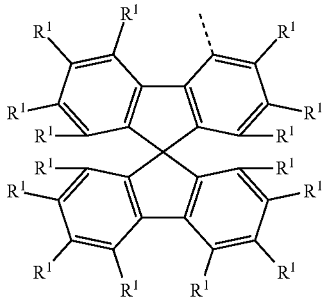
Ar-44
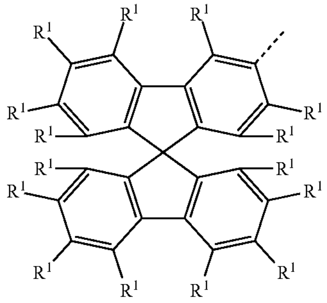
Ar-45
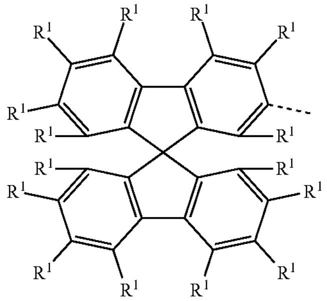
-continued
Ar-46
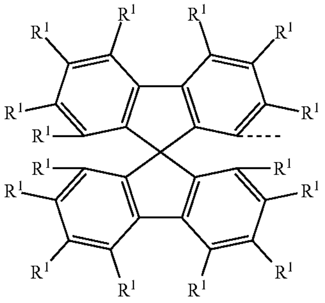
Ar-47
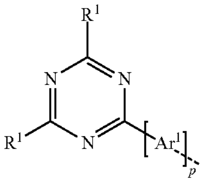
Ar-48
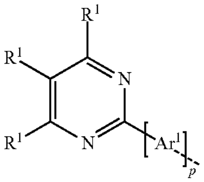
Ar-49
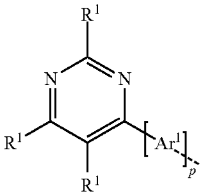
Ar-50
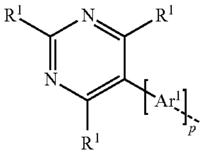
Ar-51
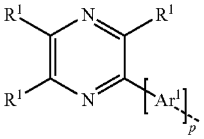
Ar-52
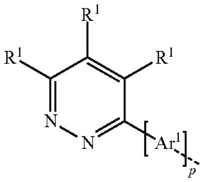
Ar-3
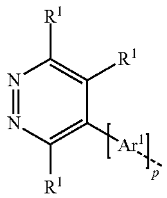

-continued
Ar-54
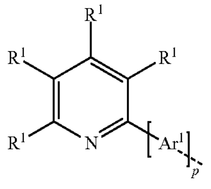
Ar-55
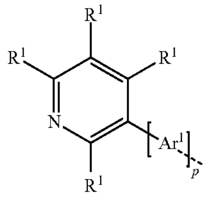
Ar-56
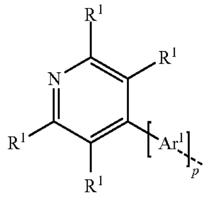
Ar-57
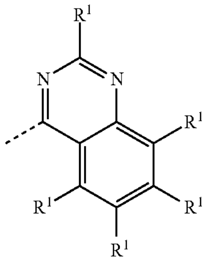
Ar-58
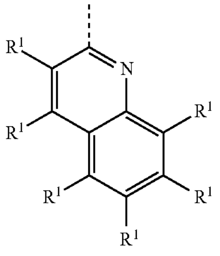
Ar-59
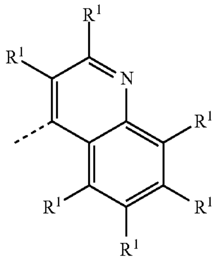
-continued
Ar-60
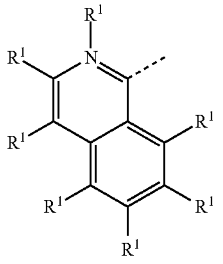
Ar-61
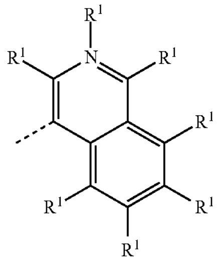
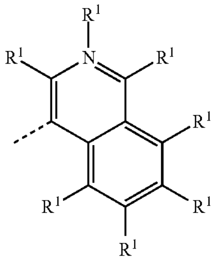
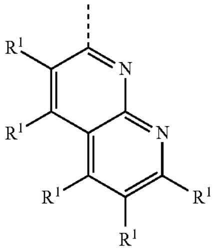
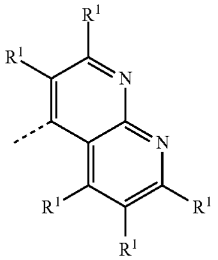
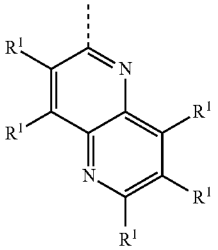

-continued

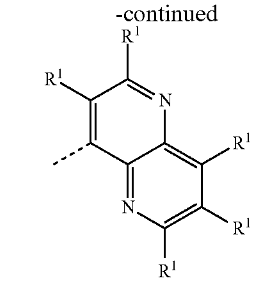

Ar-67

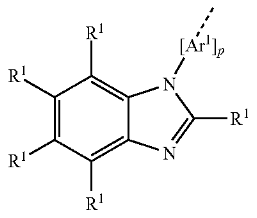

Ar-68

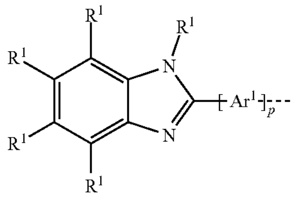

Ar-69

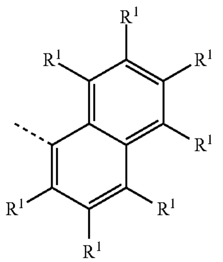

Ar-70

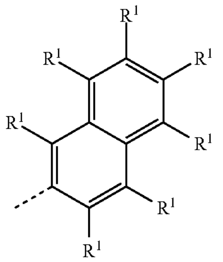

Ar-71

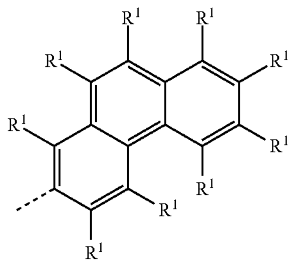

-continued

Ar-72

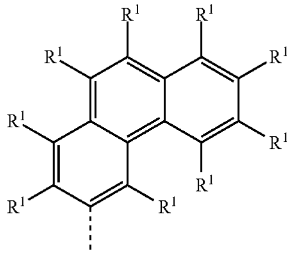

Ar-73

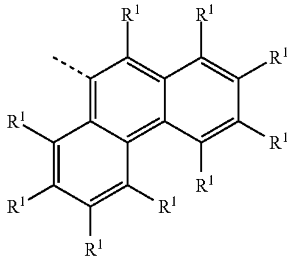

Ar-74

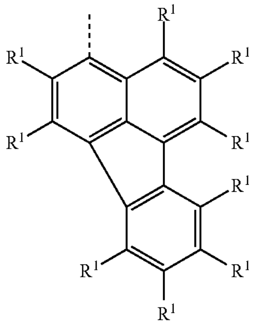

Ar-75

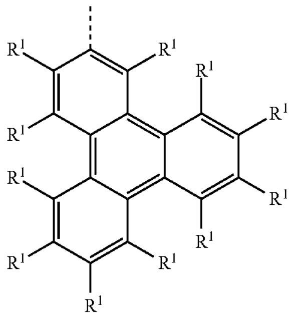

where $R^1$ is as defined above, the dotted bond represents the attachment site and, in addition:

$Ar^1$ is the same or different at each instance and is a bivalent aromatic or heteroaromatic ring system which has 6 to 18 aromatic ring atoms and may be substituted in each case by one or more $R^1$ radicals;

A is the same or different at each instance and is $C(R^1)_2$, $NR^1$, O or S;

p is 0 or 1, where p=0 means that the $Ar^1$ group is absent and that the corresponding aromatic or heteroaromatic group is bonded directly to HetAr;

q is 0 or 1, where q=0 means that no A group is bonded at this position and $R^1$ radicals are bonded to the corresponding carbon atoms instead.

When the abovementioned groups for Ar-1 to Ar-75 have two or more A groups, possible options for these include all combinations from the definition of A. Preferred embodiments in that case are those in which one A group is $NR^1$ and the other A group is $C(R^1)_2$ or in which both A groups are $NR^1$ or in which both A groups are O.

When A is $NR^1$, the substituent $R^1$ bonded to the nitrogen atom is preferably an aromatic or heteroaromatic ring system which has 5 to 24 aromatic ring atoms and may also be substituted by one or more $R^2$ radicals. In a particularly preferred embodiment, this $R^1$ substituent is the same or different at each instance and is an aromatic or heteroaromatic ring system which has 6 to 24 aromatic ring atoms, especially 6 to 18 aromatic ring atoms, which does not have any fused aryl groups and which does not have any fused heteroaryl groups in which two or more aromatic or heteroaromatic 6-membered ring groups are fused directly to one another, and which may also be substituted in each case by one or more $R^2$ radicals. Preference is given to phenyl, biphenyl, terphenyl and quaterphenyl having bonding patterns as listed above for Ar-1 to Ar-11, where these structures, rather than by $R^1$, may be substituted by one or more $R^2$ radicals, but are preferably unsubstituted. Preference is further given to triazine, pyrimidine and quinazoline as listed above for Ar-47 to Ar-50, Ar-57 and Ar-58, where these structures, rather than by $R^1$, may be substituted by one or more $R^2$ radicals.

Preferred Ar groups that are especially mentioned in formulae (I), (IIa) to (IId), (IIIa) to (IIIe), (IVa) to (IVd) are derived from structures of the formulae (Ar-1) to (Ar-75), where the substituents $R^1$ should be replaced by R. Preferably, the Ar groups mentioned in formulae (I), (IIa) to (IId), (IIIa) to (IIIe), (IVa) to (IVd) in particular may have substituents $R^1$ in place of R.

It may preferably be the case that the compound of the invention comprises a hole transport group, in which case preferably at least one of the Ar and/or R groups comprises and preferably represents a hole transport group. In addition, the $Y^a$, $Y^b$, $Y^c$ and/or $Y^d$ group may represent or form a hole transport group.

In a further embodiment, one of the Ar and/or R radicals is a group selected from arylamino groups, preferably di- or triarylamino groups, heteroarylamino groups, preferably di- or triheteroarylamino groups, carbazole groups, preference being given to carbazole groups. These groups may also be regarded as a hole-transporting group.

Particular preference is further given to inventive compounds having structures of the formula (IId) that have the following properties:

| At least one Ar radical comprises and preferably represents one of the groups | preferably | more preferably | most preferably |
|---|---|---|---|
| Ar-1 to Ar-75 | Ar-1 to Ar-42, with inclusion of at least one hole transport group | Ar-12 to Ar-42, with inclusion of at least one hole transport group | Ar-12 to Ar-16, with inclusion of at least one hole transport group |

In this context, particularly preferred embodiments of the compounds detailed in the table above and having structures of the formula (IIId), which more preferably have an Ar-12 to Ar-16 group, may contain a fused ring, preferably a ring of formulae (RA-1) to (RA-12), of the formulae (RA-1a) to (RA-4f) and/or of the formula (RB), particular preference being given to structures of the formulae (RA-1) to (RA-12), of the formulae (RA-1a) to (RA-4f) and/or of the formula (RB) with $Y^d$=N(Ar') or O, more preferably $Y^d$ =N(Ar'), where Ar' has the definition given above, especially for formula (I). Particularly preferred attachment sites have been detailed above by the structures of the formulae (VIIa) to (VIIj).

Particular preference is further given to inventive compounds having structures of the formula (IIIe) that have the following properties:

| At least one Ar radical comprises and preferably represents one of the groups | preferably | more preferably | most preferably |
|---|---|---|---|
| Ar-1 to Ar-75 | Ar-1 to Ar-42, with inclusion of at least one hole transport group | Ar-12 to Ar-42, with inclusion of at least one hole transport group | Ar-12 to Ar-16, with inclusion of at least one hole transport group |

In this context, particularly preferred embodiments of the compounds detailed in the table above and having structures of the formula (IIIe), which more preferably have an Ar-12 to Ar-16 group, may contain a fused ring, preferably a ring of formulae (RA-1) to (RA-12), of the formulae (RA-1a) to (RA-4f) and/or of the formula (RB), particular preference being given to structures of the formulae (RA-1) to (RA-12), of the formulae (RA-1a) to (RA-4f) and/or of the formula (RB) with $Y^d$=N(Ar') or O, more preferably $Y^d$ =N(Ar'), where Ar' has the definition given above, especially for formula (I). Particularly preferred attachment sites have been detailed above by the structures of the formulae (VIIa) to (VIIj).

Particular preference is further given to inventive compounds having structures of the formula (IVc) that have the following properties:

| At least one Ar radical comprises and preferably represents one of the groups | preferably | more preferably | most preferably |
|---|---|---|---|
| Ar-1 to Ar-75 | Ar-1 to Ar-42, with inclusion of at least one hole transport group | Ar-12 to Ar-42, with inclusion of at least one hole transport group | Ar-12 to Ar-16, with inclusion of at least one hole transport group |

In this context, particularly preferred embodiments of the compounds detailed in the table above and having structures of the formula (IVc), which more preferably have an Ar-12 to Ar-16 group, may contain a fused ring, preferably a ring of formulae (RA-1) to (RA-12), of the formulae (RA-1a) to (RA-4f) and/or of the formula (RB), particular preference being given to structures of the formulae (RA-1) to (RA-12), of the formulae (RA-1a) to (RA-4f) and/or of the formula (RB) with $Y^d$=N(Ar') or O, more preferably $Y^d$ =N(Ar'), where Ar' has the definition given above, especially for formula (I). Particularly preferred attachment sites have been detailed above by the structures of the formulae (VIIa) to (VIIj).

Particular preference is further given to inventive compounds having structures of the formula IVd that have the following properties:

| At least one Ar radical comprises and preferably represents one of the groups | preferably | more preferably | most preferably |
|---|---|---|---|
| Ar-1 to Ar-75 | Ar-1 to Ar-42, with inclusion of at least one hole transport group | Ar-12 to Ar-42, with inclusion of at least one hole transport group | Ar-12 to Ar-16, with inclusion of at least one hole transport group |

In this context, particularly preferred embodiments of the compounds detailed in the table above and having structures of the formula (IVd), which more preferably have an Ar-12 to Ar-16 group, may contain a fused ring, preferably a ring of formulae (RA-1) to (RA-12), of the formulae (RA-1a) to (RA-4f) and/or of the formula (RB), particular preference being given to structures of the formulae (RA-1) to (RA-12), of the formulae (RA-1a) to (RA-4f) and/or of the formula (RB) with $Y^d$=N(Ar') or O, more preferably $Y^d$=N(Ar'), where Ar' has the definition given above, especially for formula (I). Particularly preferred attachment sites have been detailed above by the structures of the formulae (VIIa) to (VIIj).

Particular preference is further given to inventive compounds having structures of the formula (Va) that have the following properties:

| At least one W radical is N(Ar), where Ar comprises and preferably represents one of the groups | preferably | more preferably | most preferably |
|---|---|---|---|
| Ar-1 to Ar-75 | Ar-1 to Ar-42, with inclusion of at least one hole transport group | Ar-12 to Ar-42, with inclusion of at least one hole transport group | Ar-12 to Ar-16, with inclusion of at least one hole transport group |

In this context, particularly preferred embodiments of the compounds detailed in the table above and having structures of the formula (Va), which more preferably have an Ar-12 to Ar-16 group, may contain a fused ring, preferably a ring of formulae (RA-1) to (RA-12), of the formulae (RA-1a) to (RA-4f) and/or of the formula (RB), particular preference being given to structures of the formulae (RA-1) to (RA-12), of the formulae (RA-1a) to (RA-4f) and/or of the formula (RB) with $Y^d$=N(Ar') or O, more preferably $Y^d$ =N(Ar'), where Ar' has the definition given above, especially for formula (I). Particularly preferred attachment sites have been detailed above by the structures of the formulae (VIIa) to (VIIj).

Particular preference is further given to inventive compounds having structures of the formula (VIa) that have the following properties:

| At least one W radical is N(Ar), where Ar comprises and preferably represents one of the groups | preferably | more preferably | most preferably |
|---|---|---|---|
| Ar-1 to Ar-75 | Ar-1 to Ar-42, with inclusion of at least one hole transport group | Ar-12 to Ar-42, with inclusion of at least one hole transport group | Ar-12 to Ar-16, with inclusion of at least one hole transport group |

In this context, particularly preferred embodiments of the compounds detailed in the table above and having structures of the formula (VIa), which more preferably have an Ar-12 to Ar-16 group, may contain a fused ring, preferably a ring of formulae (RA-1) to (RA-12), of the formulae (RA-1a) to (RA-4f) and/or of the formula (RB), particular preference being given to structures of the formulae (RA-1) to (RA-12), of the formulae (RA-1a) to (RA-4f) and/or of the formula (RB) with $Y^d$=N(Ar') or O, more preferably $Y^d$ =N(Ar'), where Ar' has the definition given above, especially for formula (I). Particularly preferred attachment sites have been detailed above by the structures of the formulae (VIIa) to (VIIj).

In the tables shown above, the preferences expressed that hole transport group is included. In this case, a carbazole group is preferably formed, such that, for example, in the structures Ar-13 to Ar-16, the A group represents an $N(R^1)$ radical. The structures Ar-12, Ar-17 already include a carbazole group, which constitutes a preferred hole transport group. In the structures Ar-18 to Ar-20, Ar-22 to Ar-25, it is sufficient that one A group represents an $N(R^1)$ radical. In addition, a triaryl group may formed by corresponding substitution. This is especially true of Ar-1 to Ar-11 radicals.

It may preferably be the case that the compound comprises an electron transport group, in which case preferably at least one of the Ar and/or R groups comprises and preferably represents an electron transport group. Electron transport groups are widely known in the technical field and promote the ability of compounds to transport and/or to conduct electrons. In addition, the $Y^a$, $Y^b$, $Y^c$ and/or $Y^d$ group may represent or form an electron transport group.

Furthermore, surprising advantages are exhibited by compounds comprising at least one structure of formula (I), (IIa) to (IId), (IIIa) to (IIIe), (IVa) to (IVd), (Va) to (Ve) and/or (VIa) to (VId) or preferred embodiments thereof in which at least one of the Ar and/or R groups comprises at least one structure selected from the group of pyridines, pyrimidines, pyrazines, pyridazines, triazines, quinazolines, quinoxalines, quinolines, isoquinolines, imidazoles and/or benzimidazoles, particular preference being given to pyrimidines, triazines and quinazolines.

Particular preference is further given to inventive compounds having structures of the formula (IId) that have the following properties:

| At least one Ar radical comprises and preferably represents one of the groups | preferably | more preferably | most preferably |
|---|---|---|---|
| Ar-1 to Ar-75 | Ar-1 to Ar-11, and Ar-47 to Ar-75 | Ar-47 to Ar-68 | Ar-47 to Ar-51 |

In this context, particularly preferred embodiments of the compounds detailed in the table above and having structures of the formula (IIId), which more preferably have an Ar-47 to Ar-51 group, may contain a fused ring, preferably a ring of formulae (RA-1) to (RA-12), of the formulae (RA-1a) to (RA-4f) and/or of the formula (RB), particular preference being given to structures of the formulae (RA-1) to (RA-12), of the formulae (RA-1a) to (RA-4f) and/or of the formula (RB) with $Y^d$=N(Ar') or O, more preferably $Y^d$ =N(Ar'), where Ar' has the definition given above, especially for formula (I). Particularly preferred attachment sites have been detailed above by the structures of the formulae (VIIa) to (VIIj).

Particular preference is further given to inventive compounds having structures of the formula (IIIe) that have the following properties:

| At least one Ar radical comprises and preferably represents one of the groups | preferably | more preferably | most preferably |
|---|---|---|---|
| Ar-1 to Ar-75 | Ar-1 to Ar-11, and Ar-47 to Ar-75 | Ar-47 to Ar-68 | Ar-47 to Ar-51 |

In this context, particularly preferred embodiments of the compounds detailed in the table above and having structures of the formula (IIIe), which more preferably have an Ar-47 to Ar-51 group, may contain a fused ring, preferably a ring of formulae (RA-1) to (RA-12), of the formulae (RA-1a) to (RA-4f) and/or of the formula (RB), particular preference being given to structures of the formulae (RA-1) to (RA-12), of the formulae (RA-1a) to (RA-4f) and/or of the formula (RB) with $Y^d$=N(Ar') or O, more preferably $Y^d$ =N(Ar'), where Ar' has the definition given above, especially for formula (I). Particularly preferred attachment sites have been detailed above by the structures of the formulae (VIIa) to (VIIj).

Particular preference is further given to inventive compounds having structures of the formula (IVc) that have the following properties:

| At least one Ar radical comprises and preferably represents one of the groups | preferably | more preferably | most preferably |
|---|---|---|---|
| Ar-1 to Ar-75 | Ar-1 to Ar-11, and Ar-47 to Ar-75 | Ar-47 to Ar-68 | Ar-47 to Ar-51 |

In this context, particularly preferred embodiments of the compounds detailed in the table above and having structures of the formula (IVc), which more preferably have an Ar-47 to Ar-51 group, may contain a fused ring, preferably a ring of formulae (RA-1) to (RA-12), of the formulae (RA-1a) to (RA-4f) and/or of the formula (RB), particular preference being given to structures of the formulae (RA-1) to (RA-12), of the formulae (RA-1a) to (RA-4f) and/or of the formula (RB) with $Y^d$=N(Ar') or O, more preferably $Y^d$ =N(Ar'), where Ar' has the definition given above, especially for formula (I). Particularly preferred attachment sites have been detailed above by the structures of the formulae (VIIa) to (VIIj).

Particular preference is further given to inventive compounds having structures of the formula (IVd) that have the following properties:

| At least one Ar radical comprises and preferably represents one of the groups | preferably | more preferably | most preferably |
|---|---|---|---|
| Ar-1 to Ar-75 | Ar-1 to Ar-11, and Ar-47 to Ar-75 | Ar-47 to Ar-68 | Ar-47 to Ar-51 |

In this context, particularly preferred embodiments of the compounds detailed in the table above and having structures of the formula (IVd), which more preferably have an Ar-47 to Ar-51 group, may contain a fused ring, preferably a ring of formulae (RA-1) to (RA-12), of the formulae (RA-1a) to (RA-4f) and/or of the formula (RB), particular preference being given to structures of the formulae (RA-1) to (RA-12), of the formulae (RA-1a) to (RA-4f) and/or of the formula (RB) with $Y^d$=N(Ar') or O, more preferably $Y^d$=N(Ar'), where Ar' has the definition given above, especially for formula (I). Particularly preferred attachment sites have been detailed above by the structures of the formulae (VIIa) to (VIIj).

Particular preference is further given to inventive compounds having structures of the formula (Va that have the following properties:

| At least one W radical is N(Ar), where Ar comprises and preferably represents one of the groups | preferably | more preferably | most preferably |
|---|---|---|---|
| Ar-1 to Ar-75 | Ar-1 to Ar-11, and Ar-47 to Ar-75 | Ar-47 to Ar-68 | Ar-47 to Ar-51 |

In this context, particularly preferred embodiments of the compounds detailed in the table above and having structures of the formula (Va), which more preferably have an Ar-47 to Ar-51 group, may contain a fused ring, preferably a ring of formulae (RA-1) to (RA-12), of the formulae (RA-1a) to (RA-4f) and/or of the formula (RB), particular preference being given to structures of the formulae (RA-1) to (RA-12), of the formulae (RA-1a) to (RA-4f) and/or of the formula (RB) with $Y^d$=N(Ar') or O, more preferably $Y^d$=N(Ar'), where Ar' has the definition given above, especially for formula (I).

Particularly preferred attachment sites have been detailed above by the structures of the formulae (VIIa) to (VIIj).

Particular preference is further given to inventive compounds having structures of the formula (VIa) that have the following properties:

| At least one W radical is N(Ar), where Ar comprises and preferably represents one of the groups | preferably | more preferably | most preferably |
|---|---|---|---|
| Ar-1 to Ar-75 | Ar-1 to Ar-11, and Ar-47 to Ar-75 | Ar-47 to Ar-68 | Ar-47 to Ar-51 |

In this context, particularly preferred embodiments of the compounds detailed in the table above and having structures of the formula (VIa), which more preferably have an Ar-47 to Ar-51 group, may contain a fused ring, preferably a ring of formulae (RA-1) to (RA-12), of the formulae (RA-1a) to (RA-4f) and/or of the formula (RB), particular preference being given to structures of the formulae (RA-1) to (RA-12), of the formulae (RA-1a) to (RA-4f) and/or of the formula (RB) with $Y^d$=N(Ar') or O, more preferably $Y^d$=N(Ar'), where Ar' has the definition given above, especially for formula (I). Particularly preferred attachment sites have been detailed above by the structures of the formulae (VIIa) to (VIIj).

There follows a description of preferred substituents R and $R^c$.

In a preferred embodiment of the invention, R is the same or different at each instance and is selected from the group consisting of H, D, F, CN, $NO_2$, $Si(R^1)_3$, $B(OR^1)_2$, a straight-chain alkyl group having 1 to 20 carbon atoms or a branched or cyclic alkyl group having 3 to 20 carbon atoms, where the alkyl group may be substituted in each case by one or more $R^1$ radicals, or an aromatic or heteroaromatic ring system which has 5 to 60 aromatic ring atoms, preferably 5 to 40 aromatic ring atoms, and may be substituted in each case by one or more $R^1$ radicals.

In a further-preferred embodiment of the invention, R is the same or different at each instance and are selected from the group consisting of H, D, F, a straight-chain alkyl group having 1 to 20 carbon atoms or a branched or cyclic alkyl group having 3 to 20 carbon atoms, where the alkyl group may be substituted in each case by one or more $R^1$ radicals, or an aromatic or heteroaromatic ring system which has 5 to 60 aromatic ring atoms, preferably 5 to 40 aromatic ring atoms, and may be substituted in each case by one or more $R^1$ radicals.

It may further be the case that at least one substituent R is the same or different at each instance and is selected from the group consisting of H, D, an aromatic or heteroaromatic ring system which has 6 to 30 aromatic ring atoms and may be substituted by one or more $R^1$ radicals, and an $N(Ar')_2$ group. In a further-preferred embodiment of the invention, the substituents either form a ring according to the structures of the formulae (RA-1) to (RA-12) or R is the same or different at each instance and is selected from the group consisting of H, D, an aromatic or heteroaromatic ring system which has 6 to 30 aromatic ring atoms and may be substituted by one or more $R^1$ radicals, and an $N(Ar')_2$ group. More preferably, R is the same or different at each instance and is selected from the group consisting of H or an aromatic or heteroaromatic ring system which has 6 to 24 aromatic ring atoms, preferably 6 to 18 aromatic ring atoms, more preferably 6 to 13 aromatic ring atoms, and may be substituted in each case by one or more $R^1$ radicals.

In a preferred embodiment of the invention, $R^c$ is the same or different at each instance and is selected from the group consisting of a straight-chain alkyl group having 1 to 20 carbon atoms or a branched or cyclic alkyl group having 3 to 20 carbon atoms, where the alkyl group may be substituted in each case by one or more $R^2$ radicals, or an aromatic or heteroaromatic ring system which has 5 to 60 aromatic ring atoms, preferably 5 to 40 aromatic ring atoms, and may be substituted in each case by one or more $R^2$ radicals.

In a further-preferred embodiment of the invention, $R^c$ is the same or different at each instance and are selected from the group consisting of a straight-chain alkyl group having 1 to 10 carbon atoms or a branched or cyclic alkyl group having 3 to 10 carbon atoms, where the alkyl group may be substituted in each case by one or more $R^1$ radicals, an aromatic or heteroaromatic ring system which has 6 to 30 aromatic ring atoms and may be substituted by one or more $R^2$ radicals. More preferably, $R^c$ is the same or different at each instance and are selected from the group consisting of a straight-chain alkyl group having 1 to 5 carbon atoms or a branched or cyclic alkyl group having 3 to 5 carbon atoms, where the alkyl group may be substituted in each case by one or more $R^2$ radicals, or an aromatic or heteroaromatic ring system which has 6 to 24 aromatic ring atoms, preferably 6 to 18 aromatic ring atoms, more preferably 6 to 13 aromatic ring atoms, and may be substituted in each case by one or more $R^2$ radicals.

In a preferred embodiment of the invention, $R^c$ is the same or different at each instance and is selected from the group consisting of a straight-chain alkyl group having 1 to 6 carbon atoms or a cyclic alkyl group having 3 to 6 carbon atoms, where the alkyl group may be substituted in each case by one or more $R^2$ radicals, or an aromatic or heteroaromatic ring system which has 6 to 24 aromatic ring atoms and may be substituted in each case by one or more $R^1$ radicals; at the same time, two $R^c$ radicals together may also form a ring system. More preferably, $R^c$ is the same or different at each instance and is selected from the group consisting of a straight-chain alkyl group having 1, 2, 3 or 4 carbon atoms or a branched or cyclic alkyl group having 3 to 6 carbon atoms, where the alkyl group may be substituted in each case by one or more $R^1$ radicals, but is preferably unsubstituted, or an aromatic ring system which has 6 to 12 aromatic ring atoms, especially 6 aromatic ring atoms, and may be substituted in each case by one or more preferably nonaromatic $R^2$ radicals, but is preferably unsubstituted; at the same time, two $R^c$ radicals together may form a ring system. Most preferably, $R^c$ is the same or different at each instance and is selected from the group consisting of a straight-chain alkyl group having 1, 2, 3 or 4 carbon atoms, or a branched alkyl group having 3 to 6 carbon atoms. Most preferably, $R^c$ is a methyl group or is a phenyl group, where two phenyl groups together may form a ring system, preference being given to a methyl group over a phenyl group.

Preferred aromatic or heteroaromatic ring systems R, $R^c$ or Ar are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene, especially 1- or 2-bonded naphthalene, indole, benzofuran, benzothiophene, carbazole which may be joined via the 1, 2, 3 or 4 position, dibenzofuran which may be joined via the 1, 2, 3 or 4 position, dibenzothiophene which may be joined via the 1, 2, 3 or 4 position, indenocarbazole, indolocarbazole, pyridine, pyrimidine, pyrazine, pyridazine, triazine, quinoline, isoquinoline, quinazoline, quinoxaline, phenanthrene or triphenylene, each of which may be substituted by one or more $R^1$ radicals. The structures Ar-1 to Ar-75 listed above are particularly preferred, preference being given to structures of the formulae (Ar-1), (Ar-2), (Ar-3), (Ar-12), (Ar-13), (Ar-14), (Ar-15), (Ar-16), (Ar-69), (Ar-70), (Ar-75), and particular preference to structures of the formulae (Ar-1), (Ar-2), (Ar-3), (Ar-12), (Ar-13), (Ar-14), (Ar-15), (Ar-16).

Further suitable R groups are groups of the formula $—Ar^4—N(Ar^2)(Ar^3)$ where $Ar^2$, $Ar^3$ and $Ar^4$ are the same or different at each instance and are an aromatic or heteroaromatic ring system which has 5 to 24 aromatic ring atoms and may be substituted in each case by one or more $R^1$ radicals. The total number of aromatic ring atoms in $Ar^2$, $Ar^3$ and $Ar^4$ here is not more than 60 and preferably not more than 40.

In this case, $Ar^4$ and $Ar^2$ may also be bonded to one another and/or $Ar^2$ and $Ar^3$ to one another by a group selected from $C(R^1)_2$, $NR^1$, O and S. Preferably, $Ar^4$ and $Ar^2$ are joined to one another and $Ar^2$ and $Ar^3$ to one another in the respective ortho position to the bond to the nitrogen atom. In a further embodiment of the invention, none of the $Ar^2$, $Ar^3$ and $Ar^4$ groups are bonded to one another.

Preferably, $Ar^4$ is an aromatic or heteroaromatic ring system which has 6 to 24 aromatic ring atoms, preferably 6 to 12 aromatic ring atoms, and may be substituted in each case by one or more $R^1$ radicals. More preferably, $Ar^4$ is selected from the group consisting of ortho-, meta- or para-phenylene or ortho-, meta- or para-biphenyl, each of which may be substituted by one or more $R^1$ radicals, but are preferably unsubstituted. Most preferably, $Ar^4$ is an unsubstituted phenylene group.

Preferably, $Ar^2$ and $Ar^3$ are the same or different at each instance and are an aromatic or heteroaromatic ring system which has 6 to 24 aromatic ring atoms and may be substituted in each case by one or more $R^1$ radicals. Particularly preferred $Ar^2$ and $Ar^3$ groups are the same or different at each instance and are selected from the group consisting of benzene, ortho-, meta- or para-biphenyl, ortho-, meta- or para-terphenyl or branched terphenyl, ortho-, meta- or para-quaterphenyl or branched quaterphenyl, 1-, 2-, 3- or 4-fluorenyl, 1-, 2-, 3- or 4-spirobifluorenyl, 1- or 2-naphthyl, indole, benzofuran, benzothiophene, 1-, 2-, 3- or 4-carbazole, 1-, 2-, 3- or 4-dibenzofuran, 1-, 2-, 3- or 4-dibenzothiophene, indenocarbazole, indolocarbazole, 2-, 3- or 4-pyridine, 2-, 4- or 5-pyrimidine, pyrazine, pyridazine, triazine, phenanthrene or triphenylene, each of which may be substituted by one or more $R^1$ radicals. Most preferably, $Ar^2$ and $Ar^3$ are the same or different at each instance and are selected from the group consisting of benzene, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene, especially 1-, 2-, 3- or 4-fluorene, or spirobifluorene, especially 1-, 2-, 3- or 4-spirobifluorene.

In a further preferred embodiment of the invention, $R^1$ is the same or different at each instance and is selected from the group consisting of H, D, F, CN, a straight-chain alkyl group having 1 to 10 carbon atoms or a branched or cyclic alkyl group having 3 to 10 carbon atoms, where the alkyl group may be substituted in each case by one or more $R^2$ radicals, or an aromatic or heteroaromatic ring system which has 6 to 24 aromatic ring atoms and may be substituted in each case by one or more $R^2$ radicals. In a particularly preferred embodiment of the invention, $R^1$ is the same or different at each instance and is selected from the group consisting of H, a straight-chain alkyl group having 1 to 6 carbon atoms, especially having 1, 2, 3 or 4 carbon atoms, or a branched or cyclic alkyl group having 3 to 6 carbon atoms, where the alkyl group may be substituted by one or more $R^5$ radicals, but is preferably unsubstituted, or an aromatic or heteroaromatic ring system which has 6 to 13 aromatic ring atoms and may be substituted in each case by one or more $R^5$ radicals, but is preferably unsubstituted.

In a further preferred embodiment of the invention, $R^2$ is the same or different at each instance and is H, an alkyl group having 1 to 4 carbon atoms or an aryl group having 6 to 10 carbon atoms, which may be substituted by an alkyl group having 1 to 4 carbon atoms, but is preferably unsubstituted.

At the same time, in compounds of the invention that are processed by vacuum evaporation, the alkyl groups preferably have not more than five carbon atoms, more preferably not more than 4 carbon atoms, most preferably not more than 1 carbon atom. For compounds that are processed from solution, suitable compounds are also those substituted by alkyl groups, especially branched alkyl groups, having up to 10 carbon atoms or those substituted by oligoarylene groups, for example ortho-, meta- or para-terphenyl or branched terphenyl or quaterphenyl groups.

It may further be the case that the compound comprises exactly two or exactly three structures of formula (I), (IIa) to (IId), (IIIa) to (IIIe), (IVa) to (IVd), (Va) to (Ve), (VIa) to (VId) and/or preferred embodiments thereof.

The abovementioned preferred embodiments may be combined with one another as desired within the restrictions defined in claim 1. In a particularly preferred embodiment of the invention, the abovementioned preferences occur simultaneously.

Examples of preferred compounds according to the embodiments detailed above are the compounds shown in the following table:

1

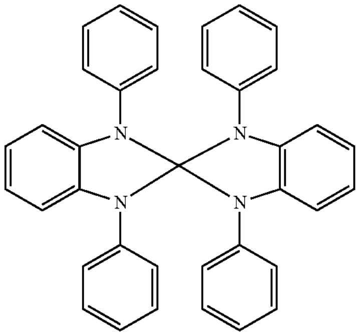

-continued
2
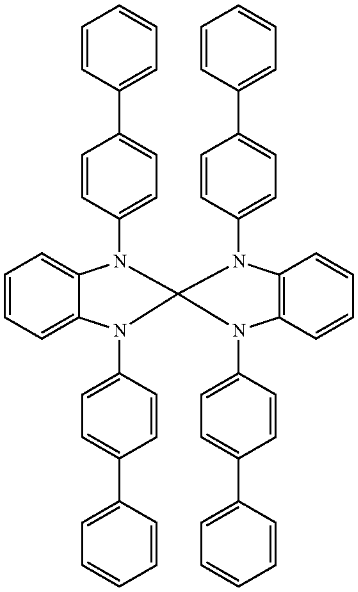
3
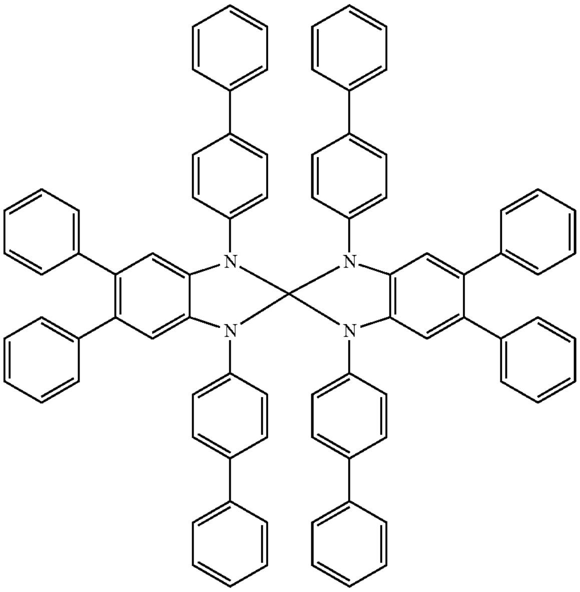
4
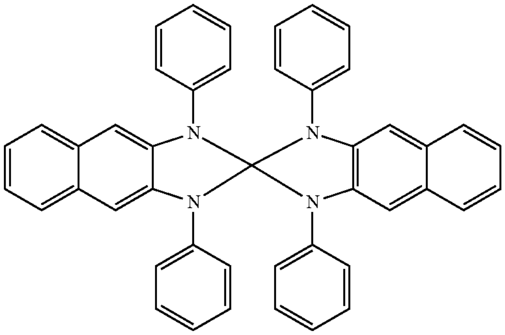
-continued
5
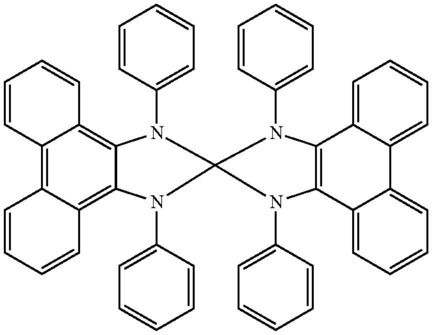
6
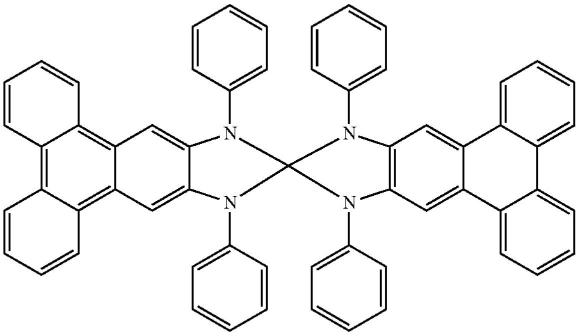
7
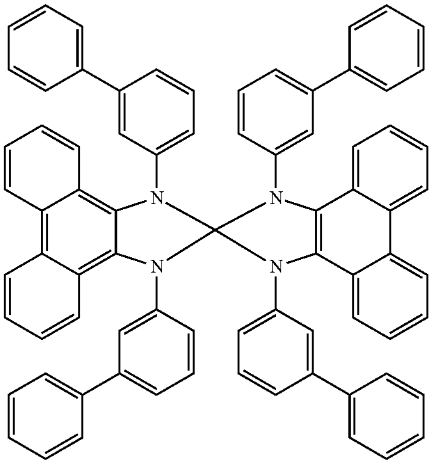
8
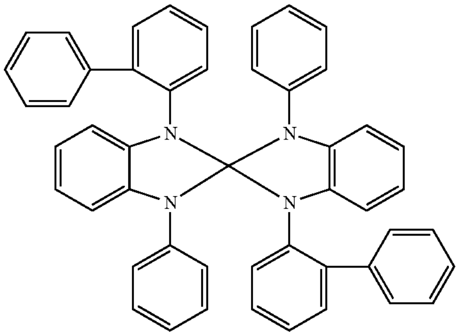

-continued
9
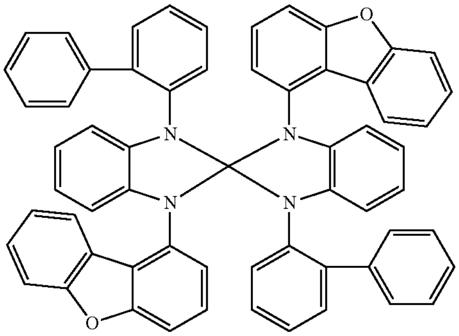
10
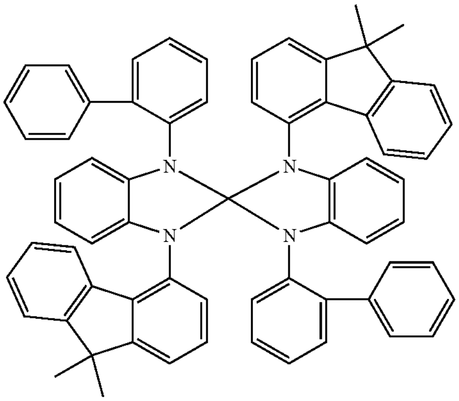
11
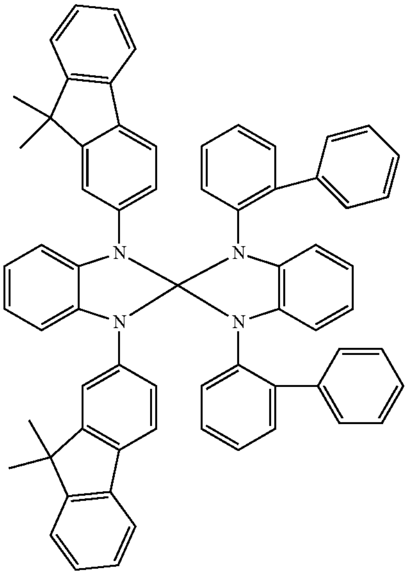
-continued
12
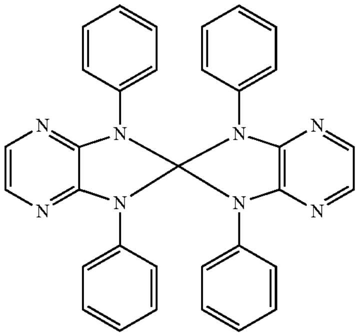
13
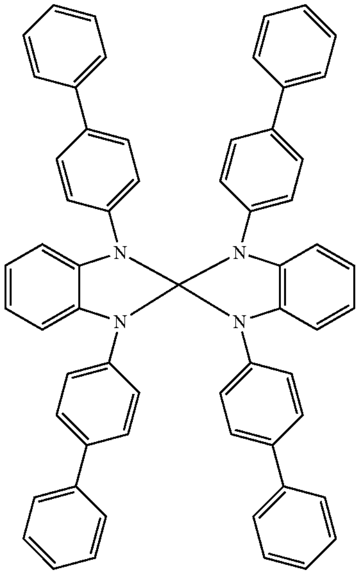
14
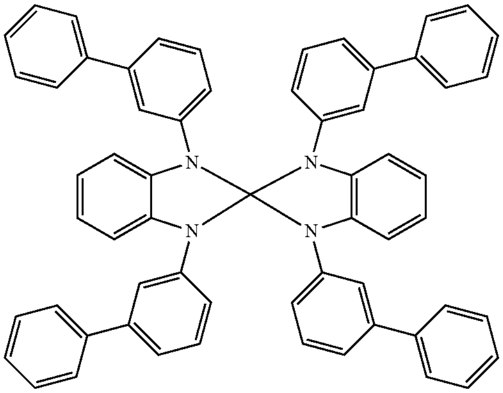

-continued
15
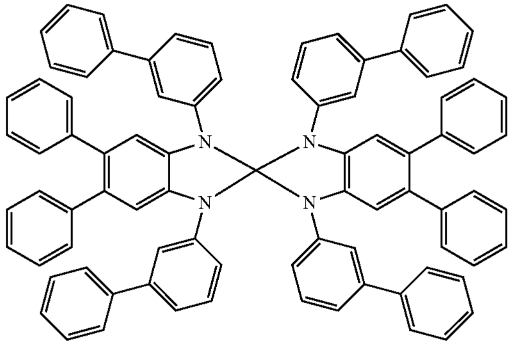
16
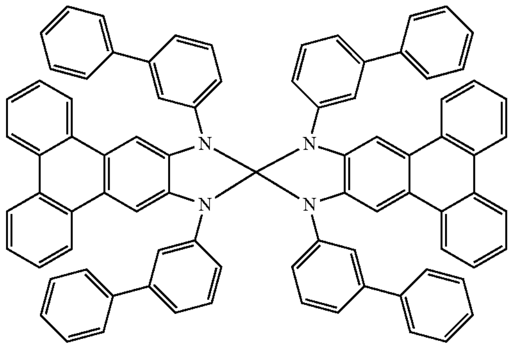
17
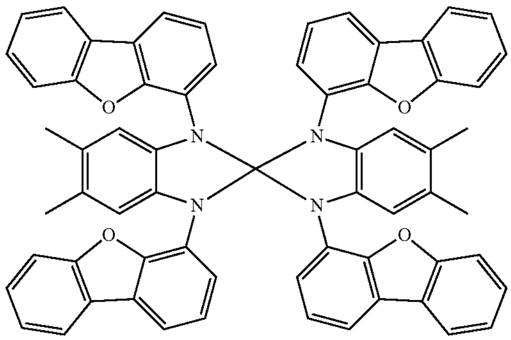
18
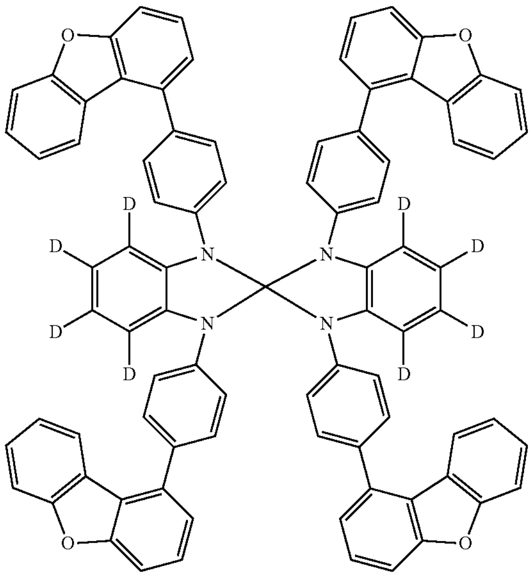
-continued
19
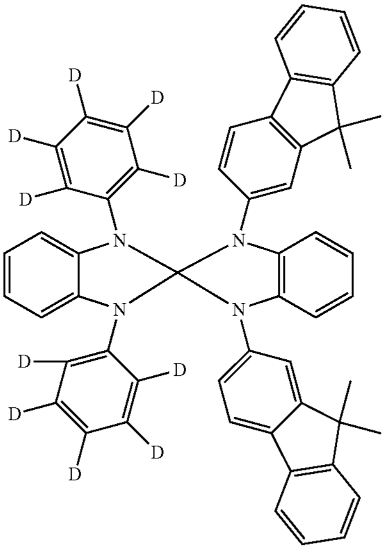
20
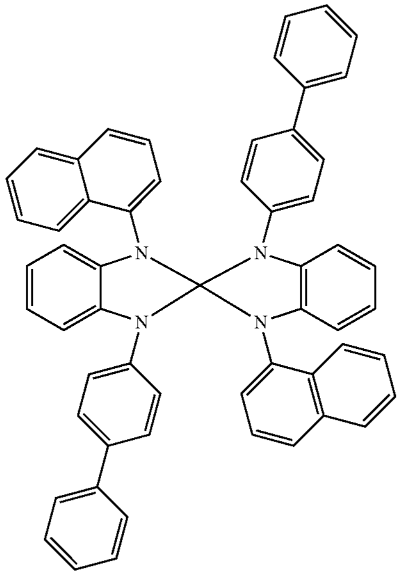
21
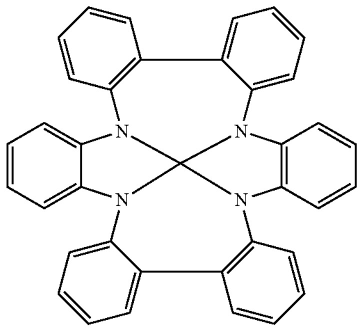

-continued
22
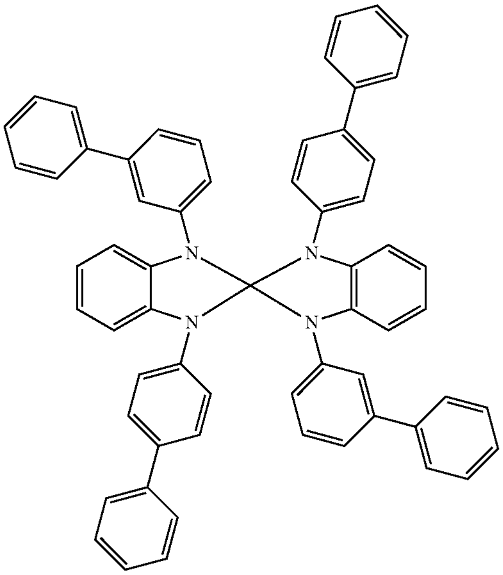
23
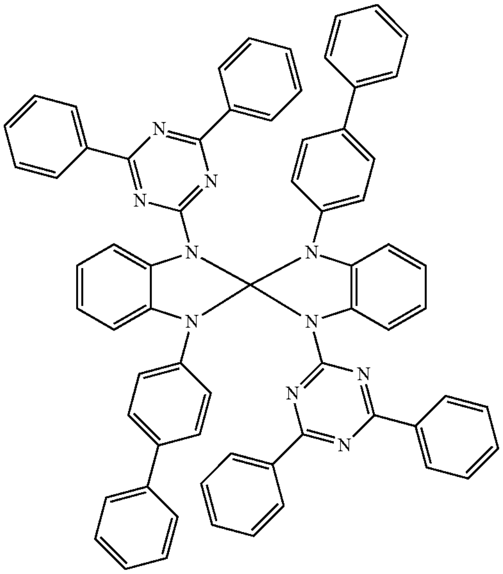
-continued
24
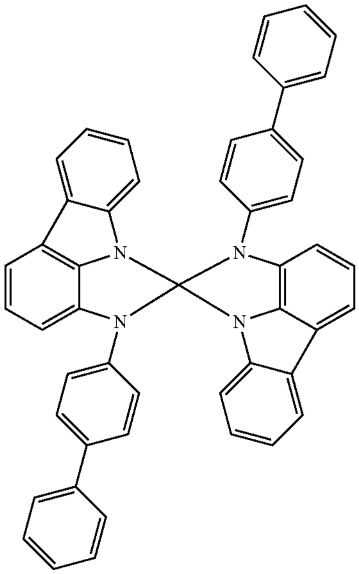
25
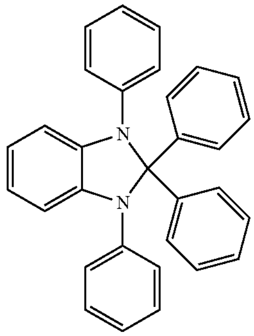
26
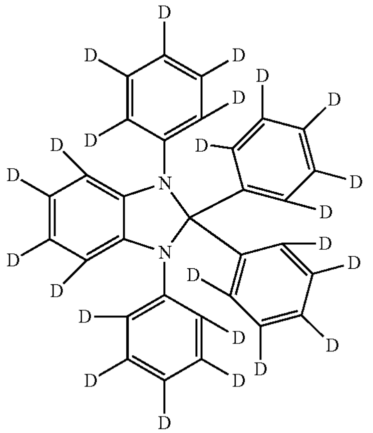

-continued
27
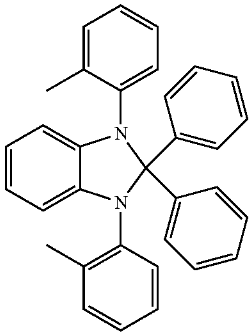
28
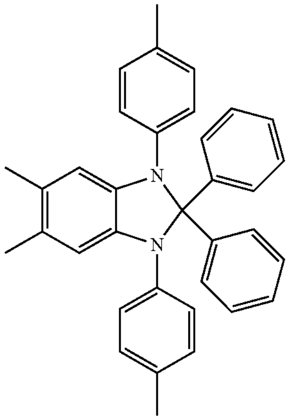
29
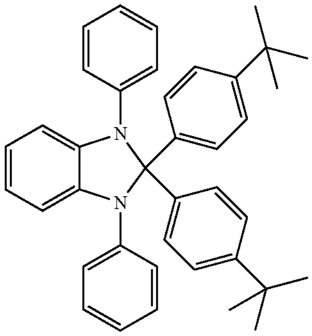
30
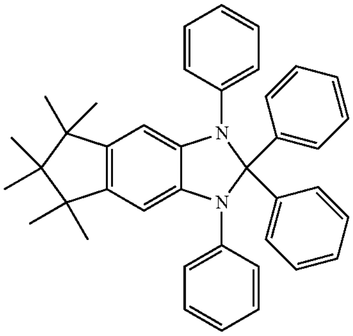
-continued
31
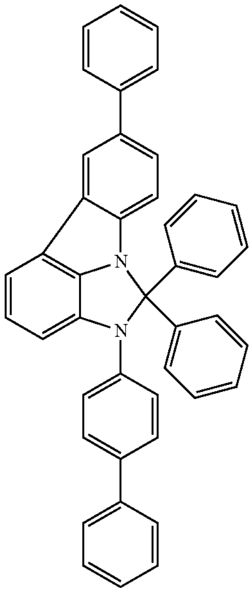
32
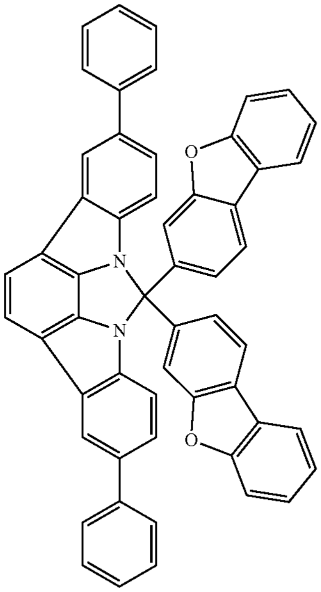

33
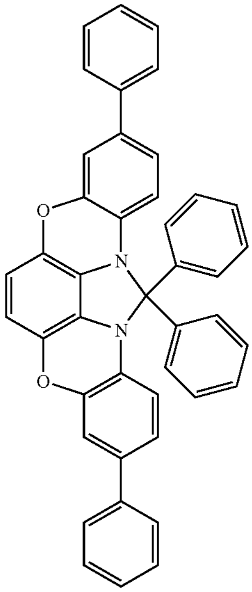
34
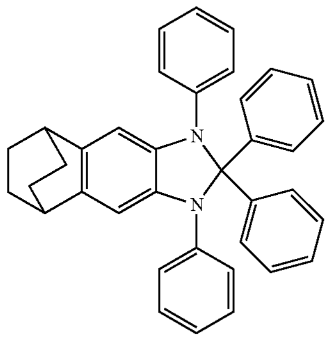
35
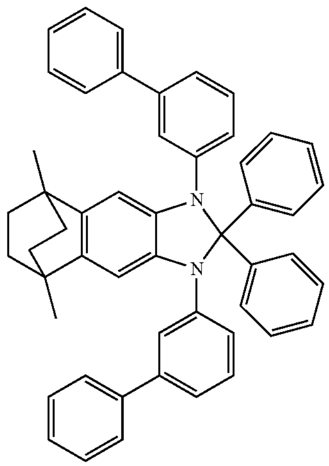
36
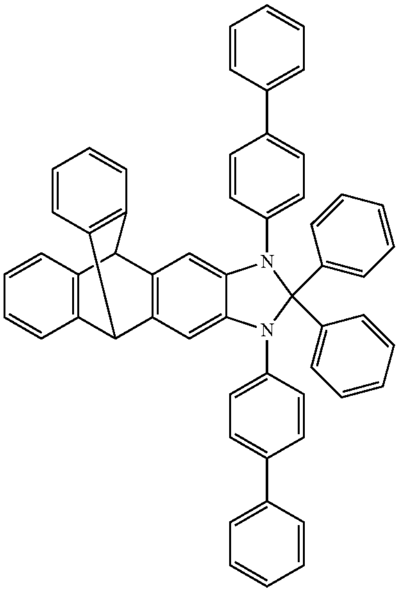
37
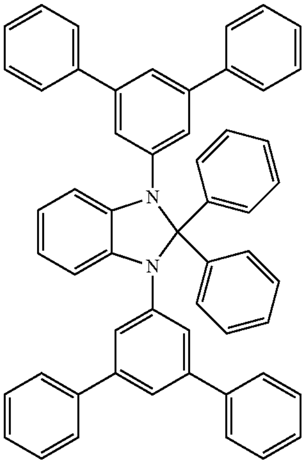
38
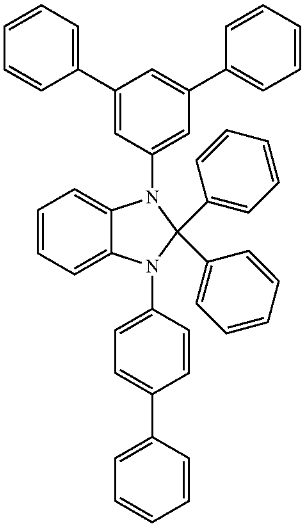

-continued
39
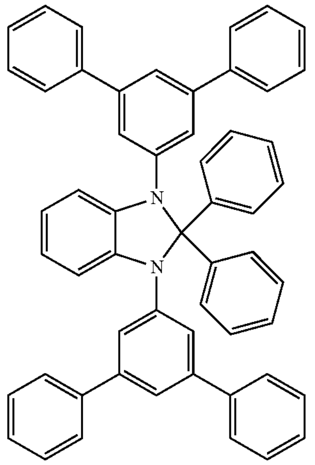
40
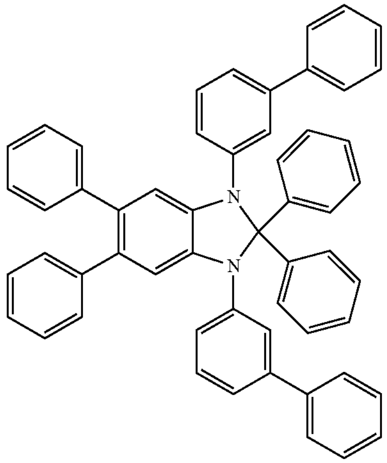
41
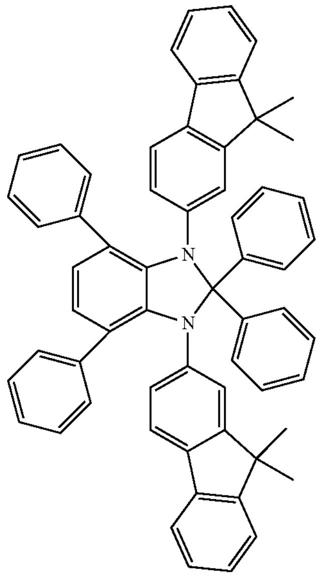
-continued
42
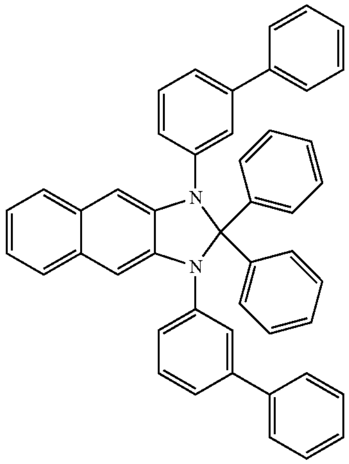
43
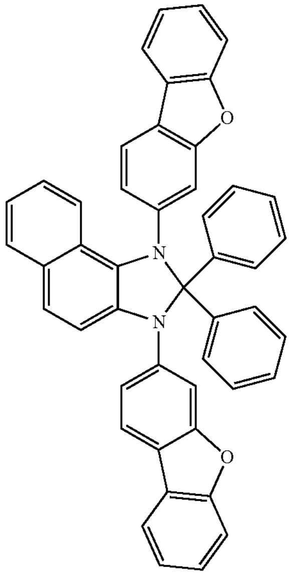
44
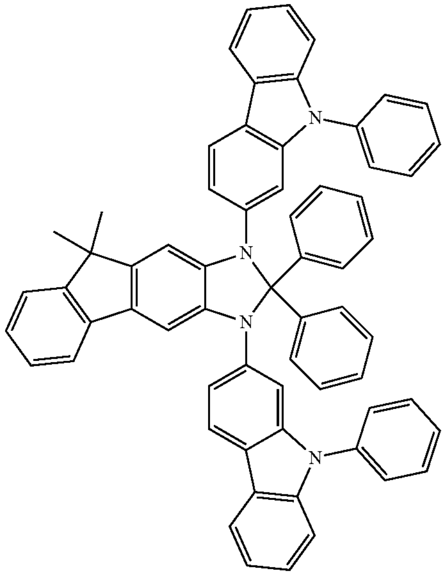

-continued
45
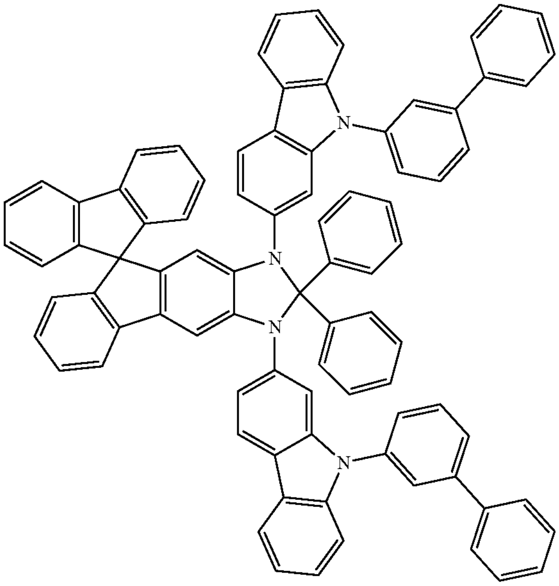
46
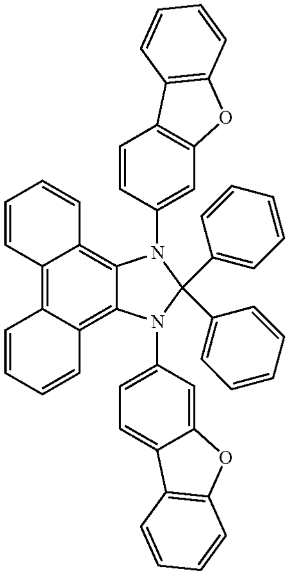
-continued
47
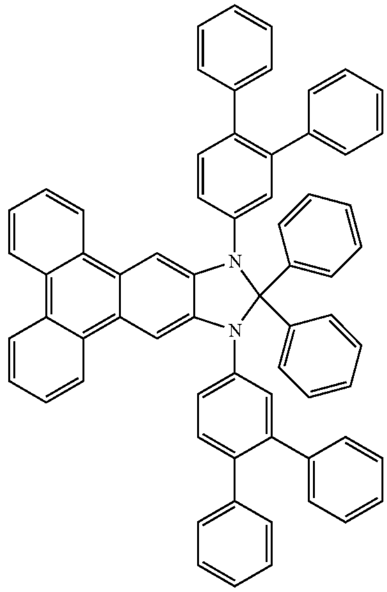
48
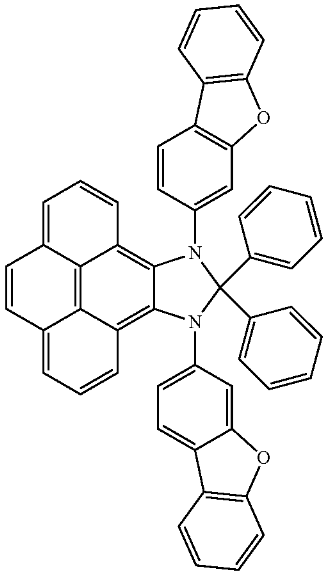

-continued
49
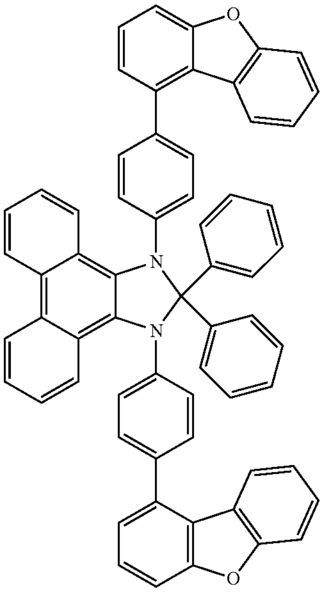
50
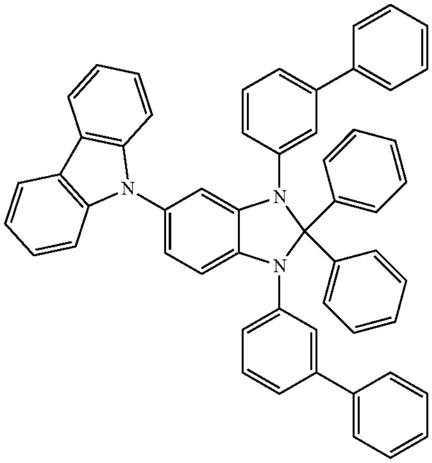
51
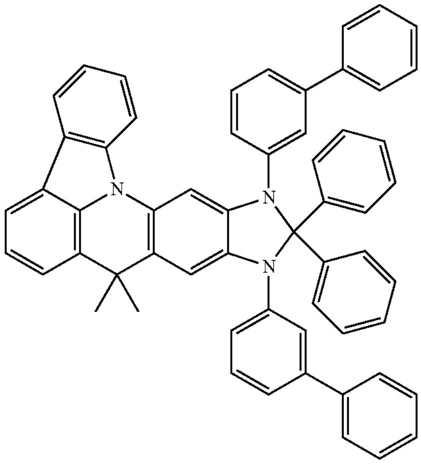
-continued
52
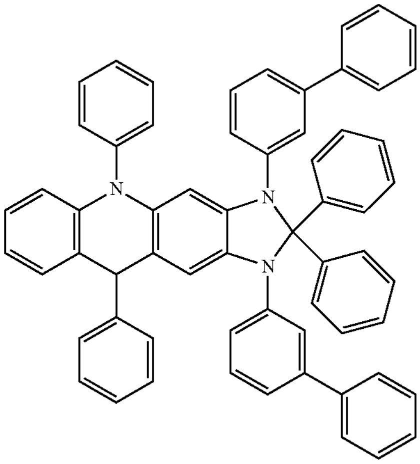
53
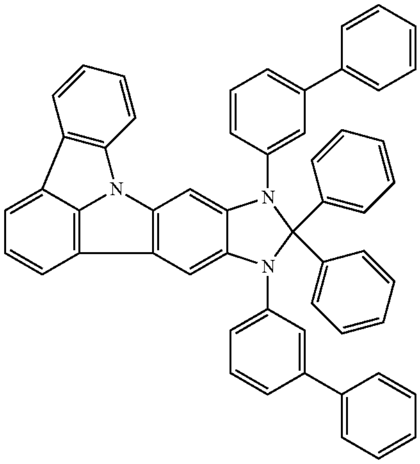
54
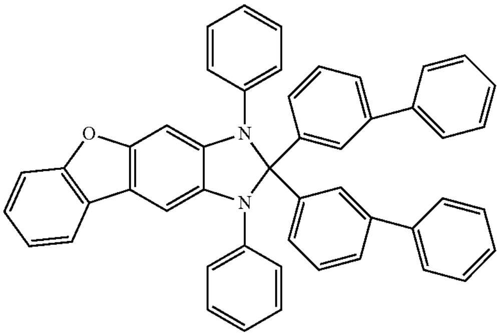
55
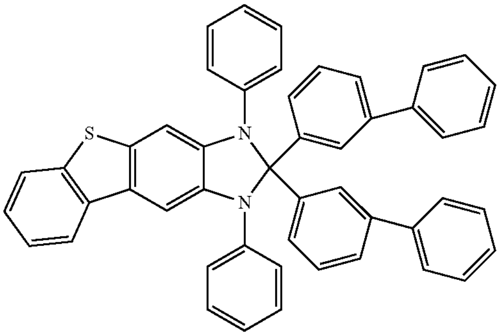

-continued
56
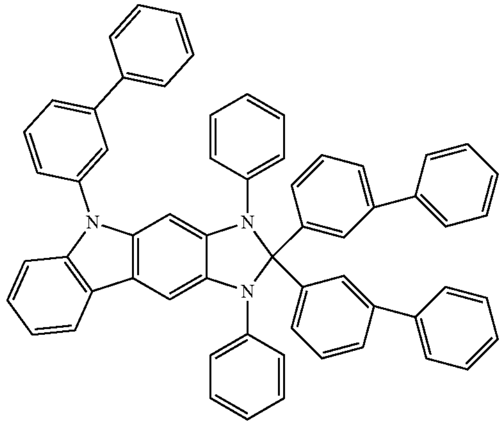
57
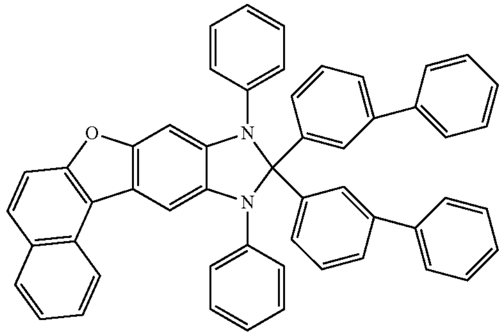
58
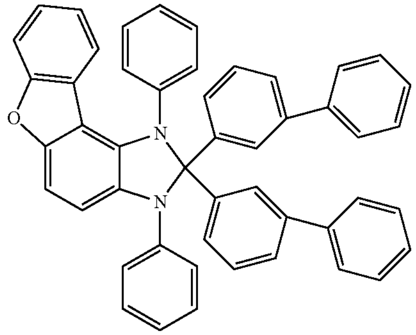
-continued
59
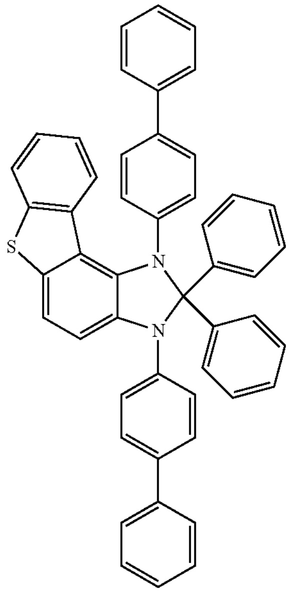
60
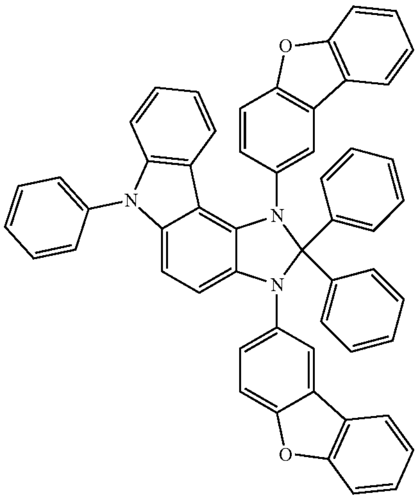
61
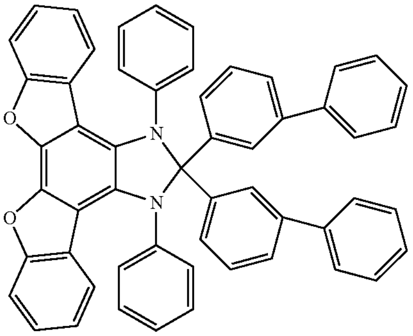

-continued
62
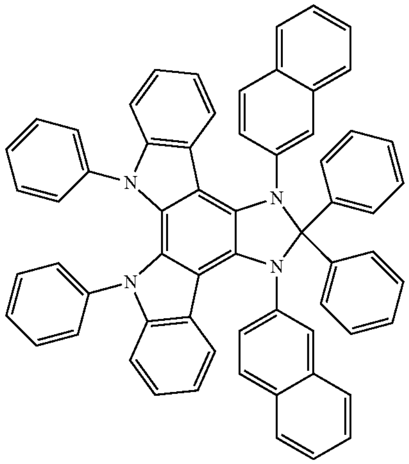
63
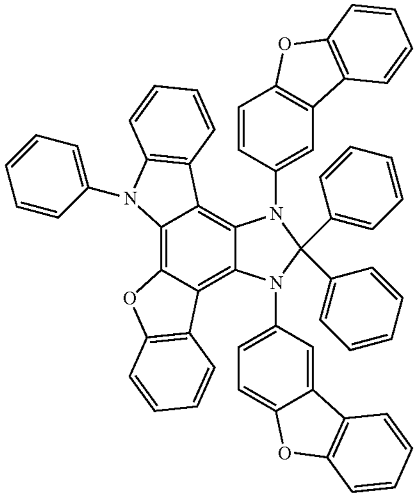
64
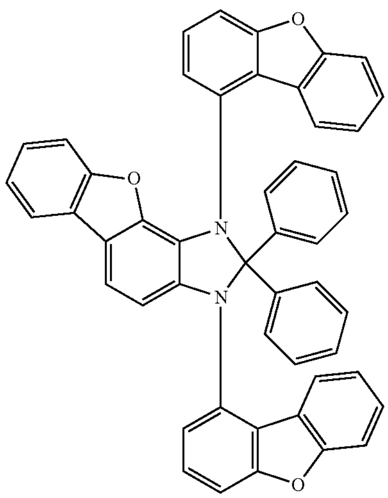
-continued
65
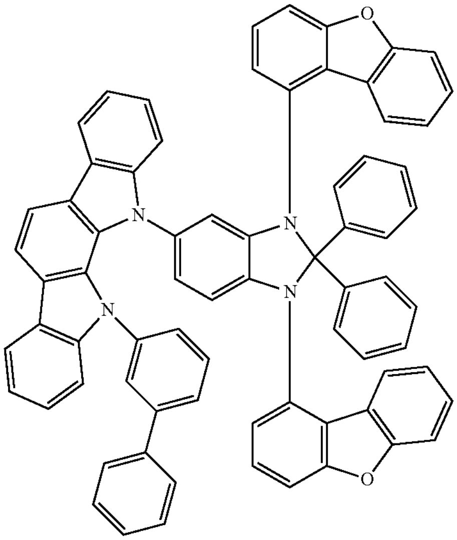
66
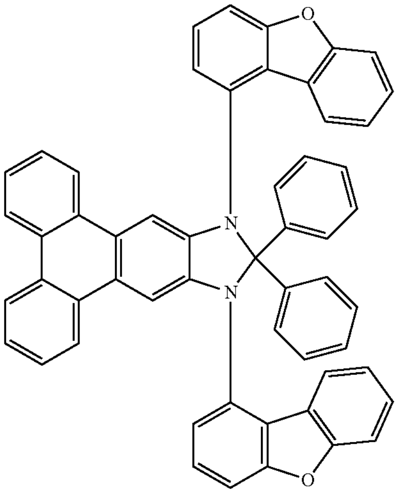
67
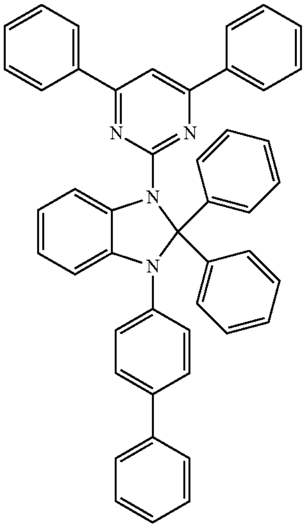

-continued
68
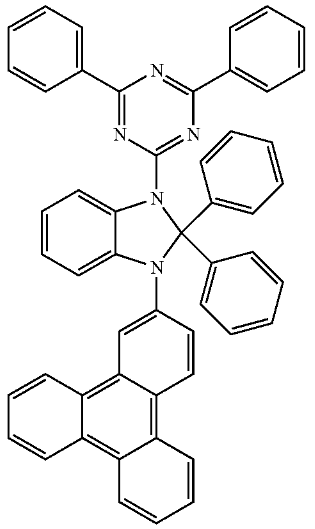
69
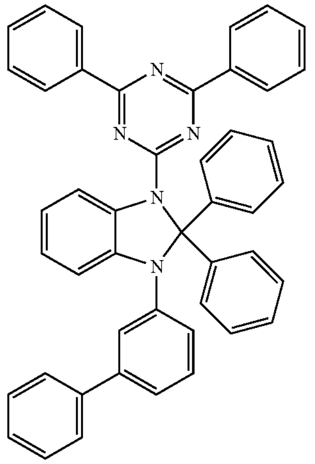
70
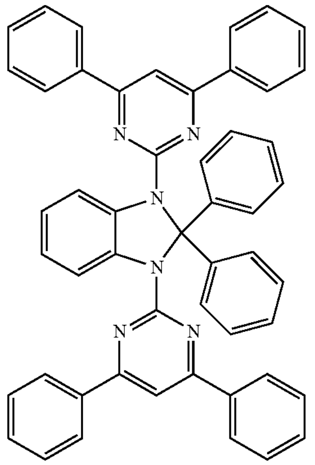
-continued
71
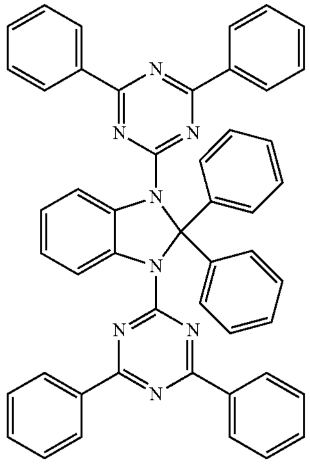
72
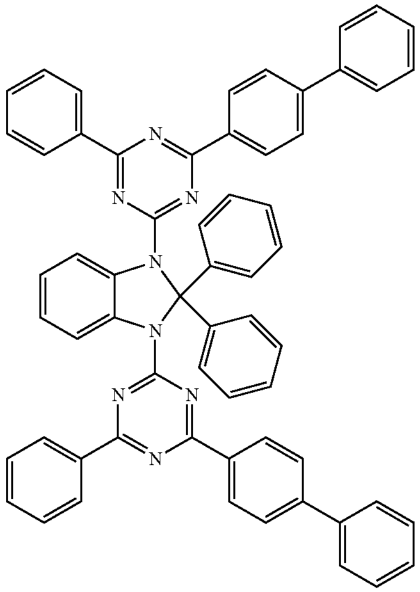
73
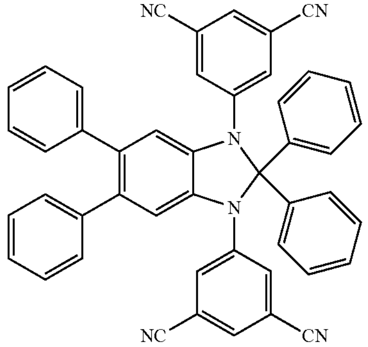

-continued
74
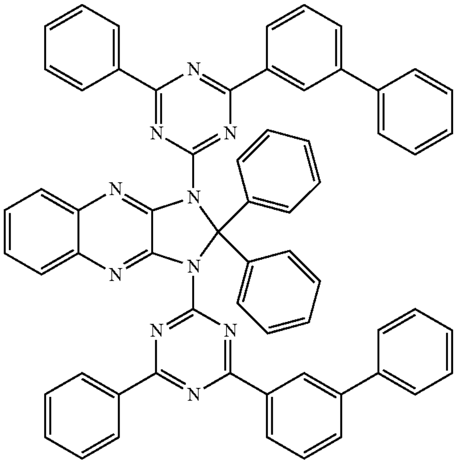
75
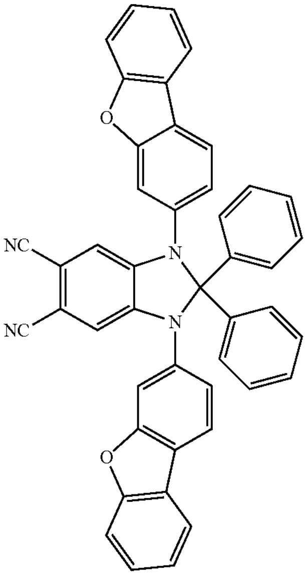
76
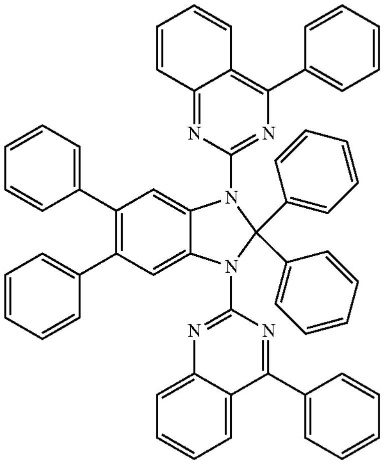
-continued
77
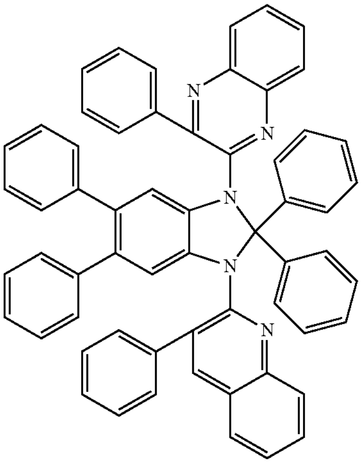
78
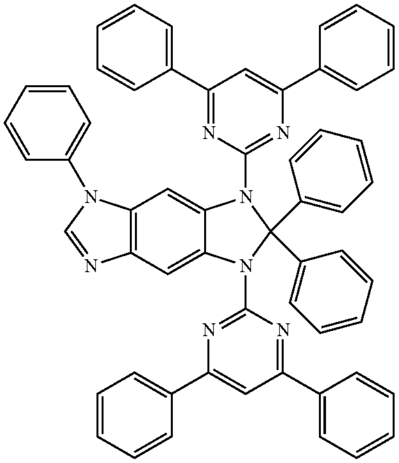
79
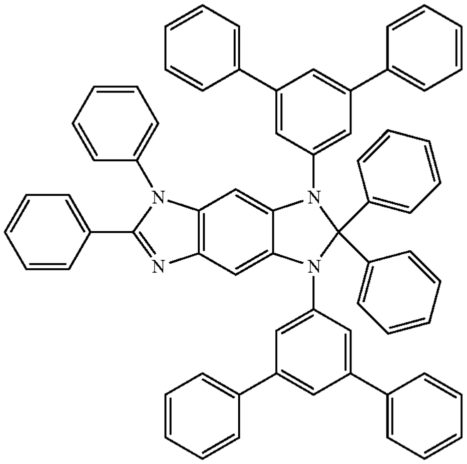

-continued
80
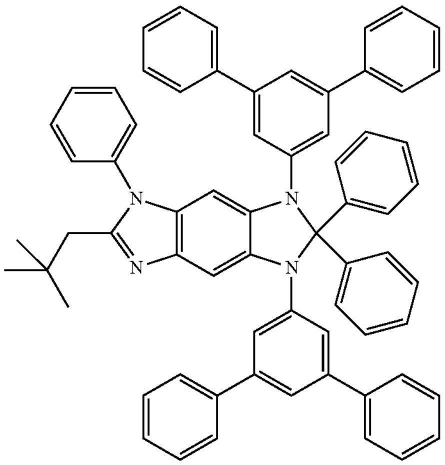
81
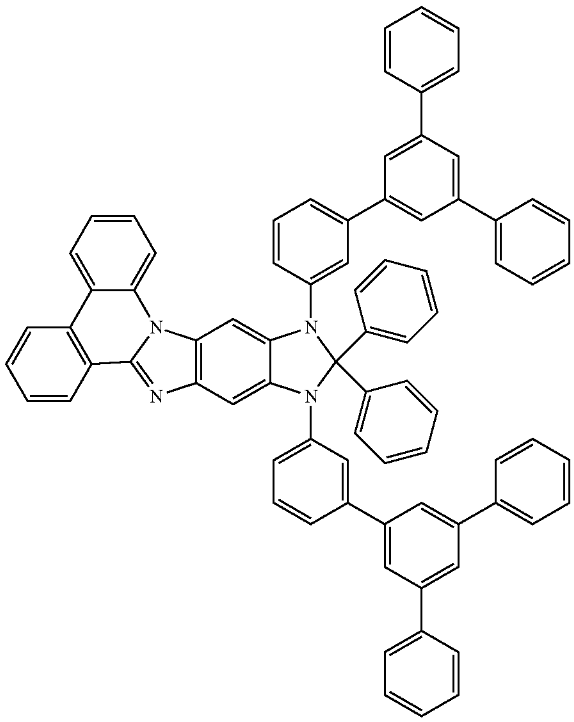
82
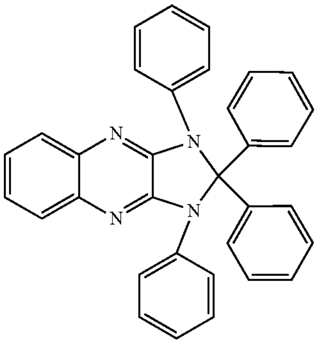
-continued
83
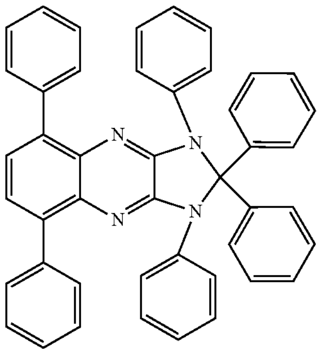
84
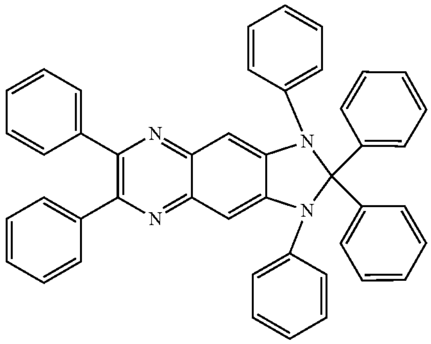
85
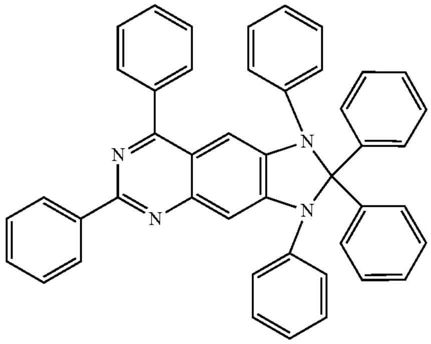
86
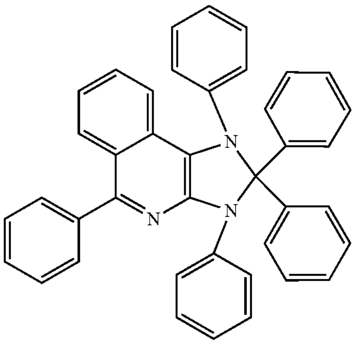

-continued
87
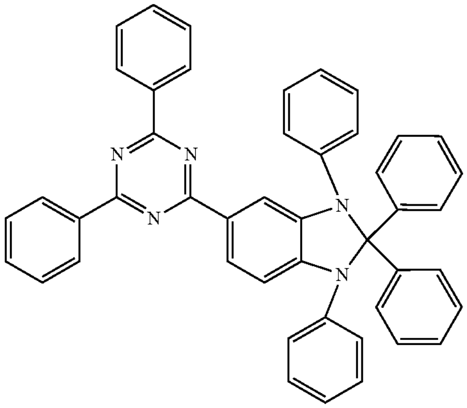
88
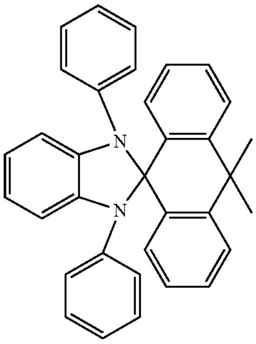
89
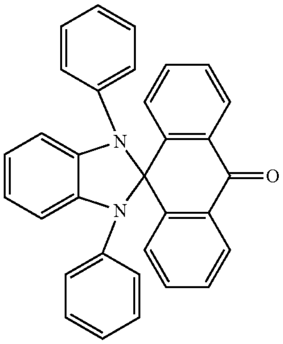
90
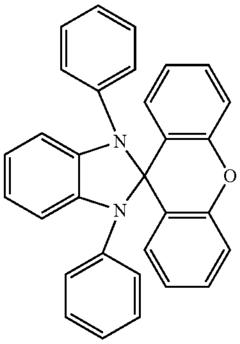
-continued
91
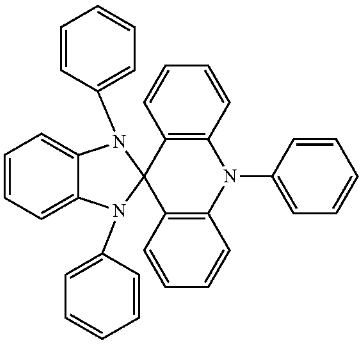
92
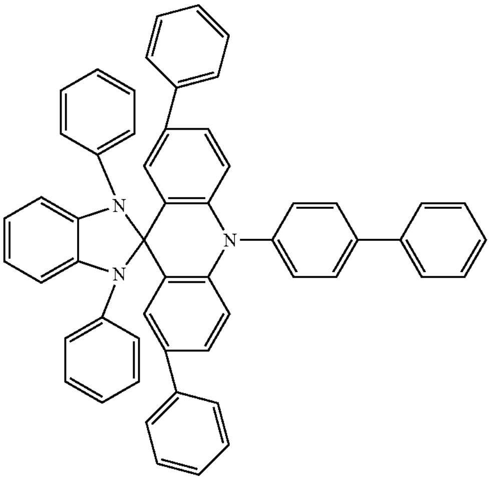
93
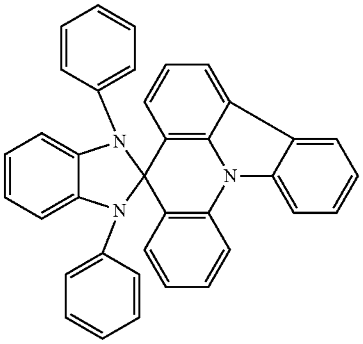

-continued
94
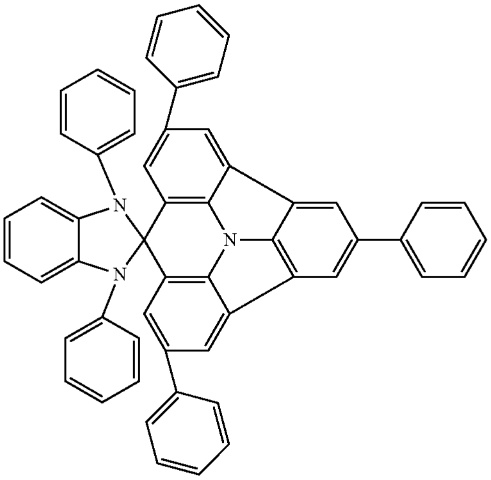
95
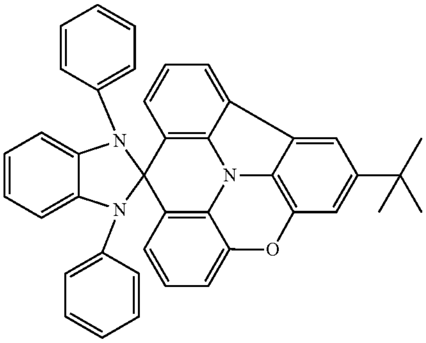
96
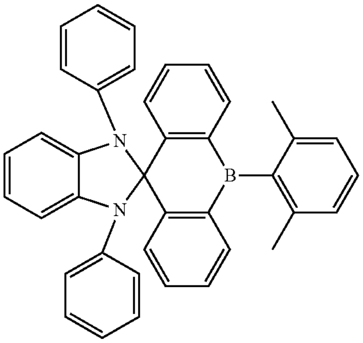
97
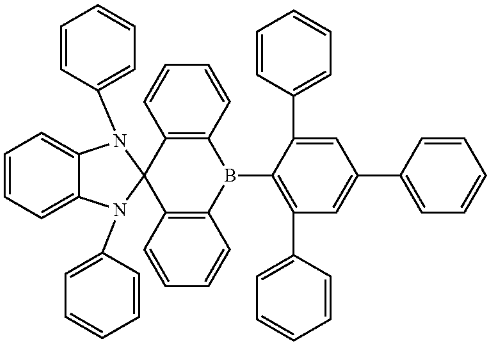
-continued
98
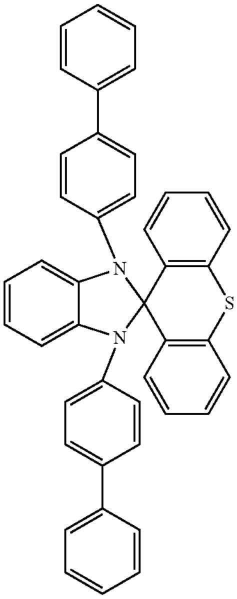
99
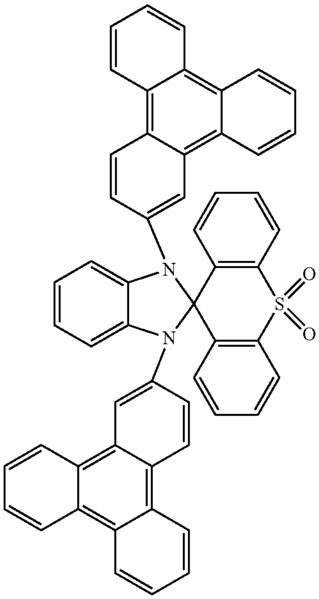

-continued
99
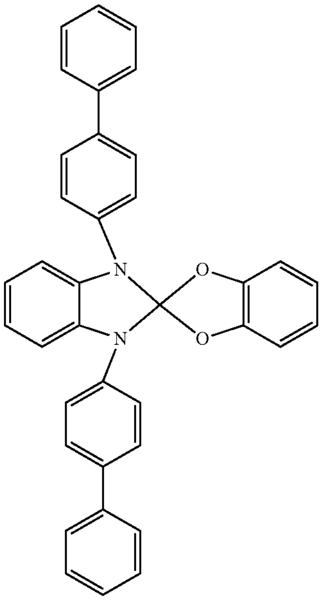
100
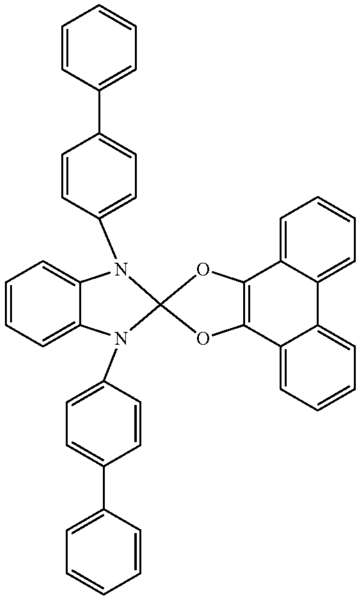
101
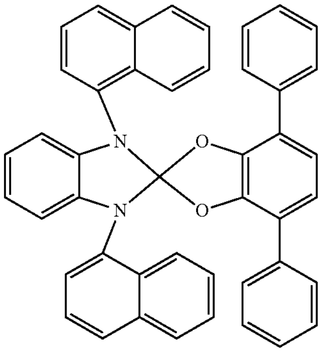
-continued
102
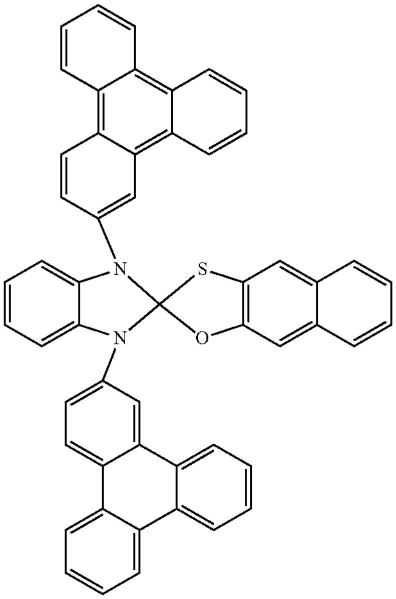
103
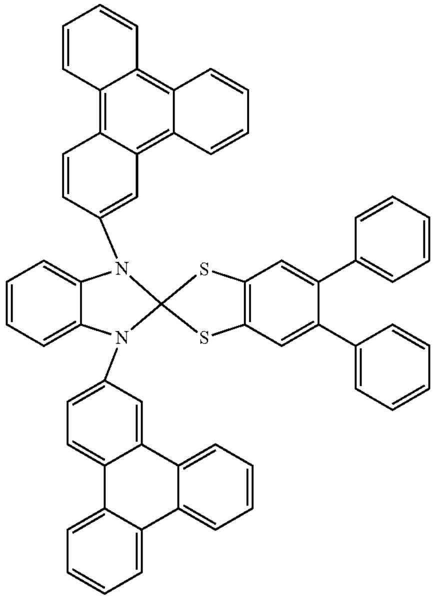
104
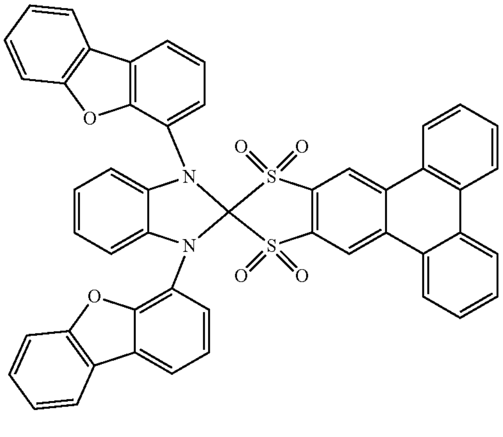

-continued
105
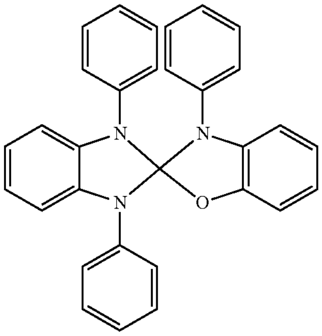
106
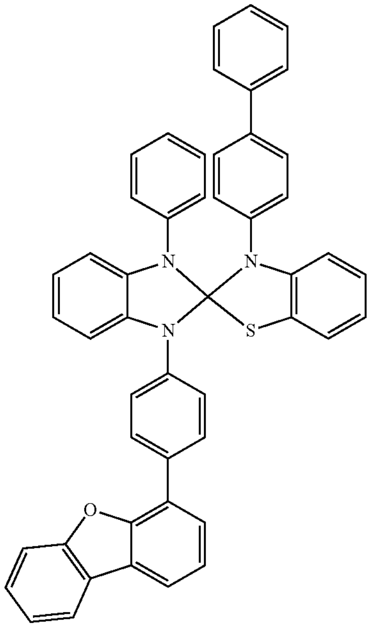
107
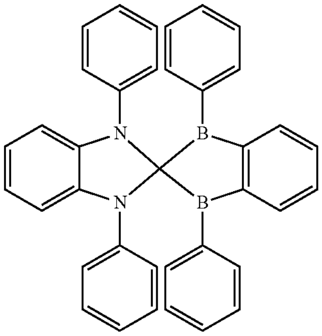
108
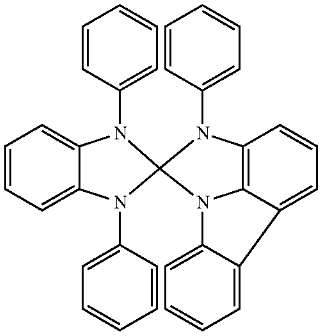
-continued
109
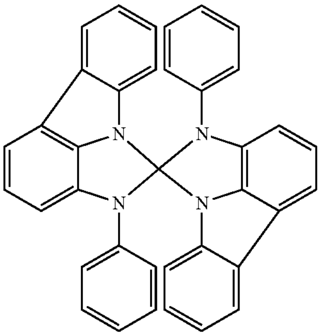
110
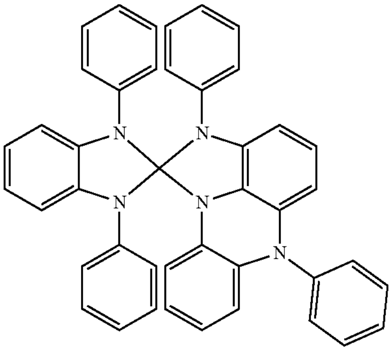
111
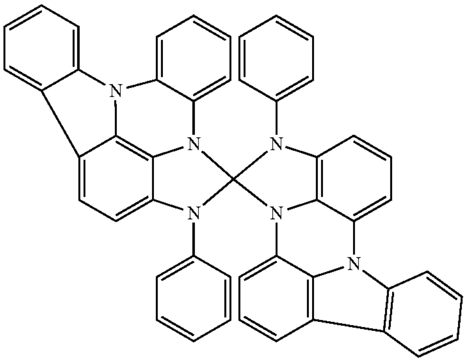
112
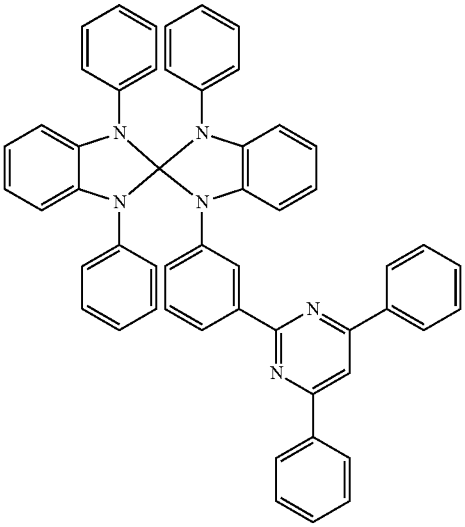

-continued
113
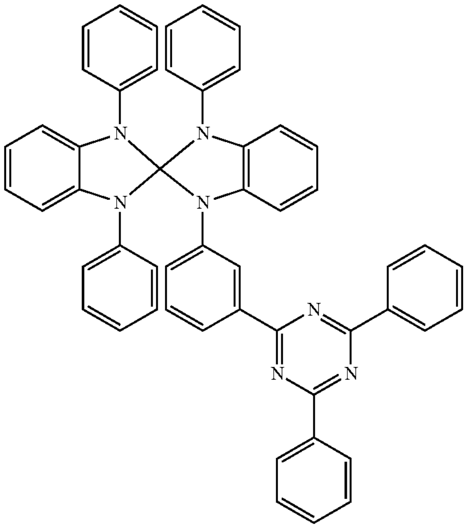
115
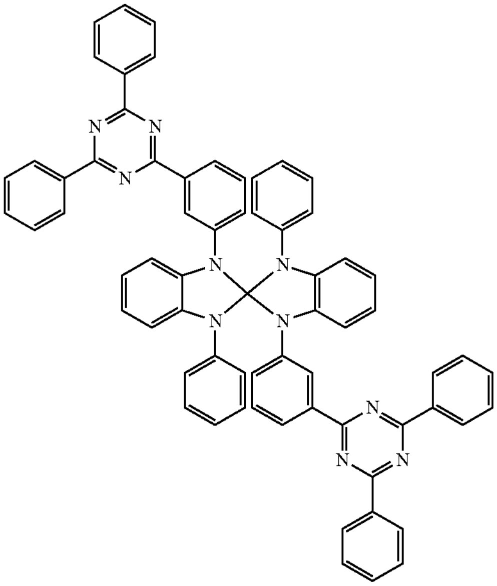
116
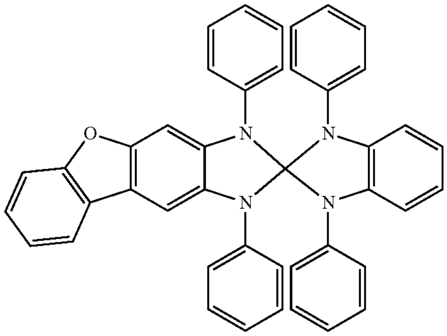
-continued
117
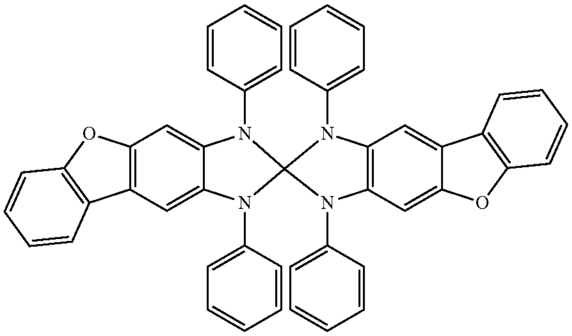
118
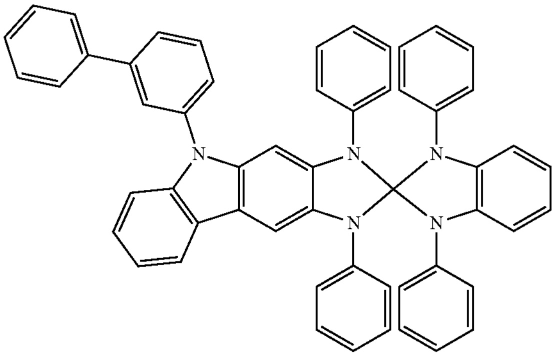
119
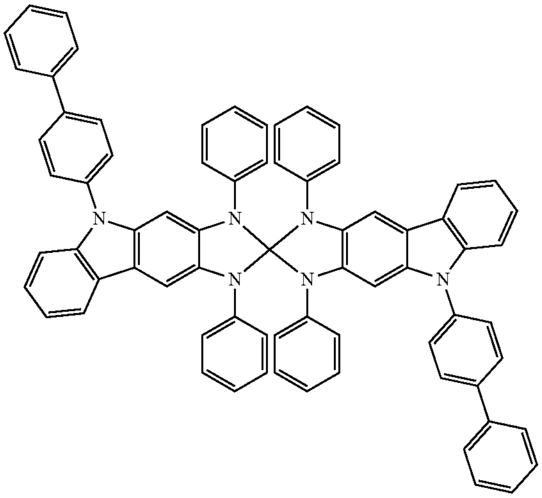
120
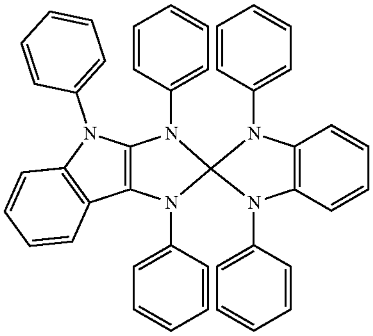

121
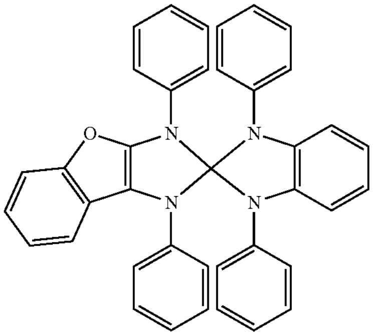
122
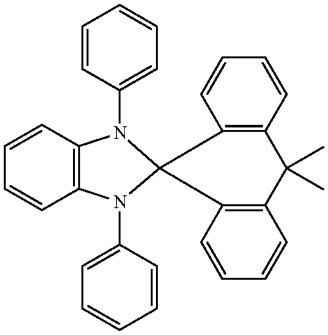
123
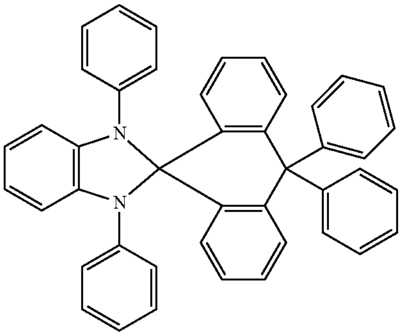
124
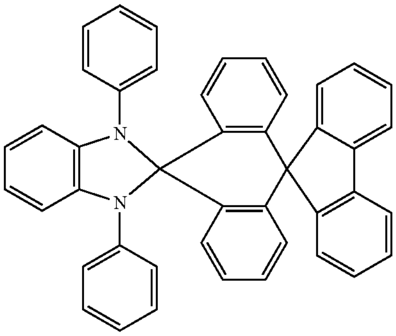
125
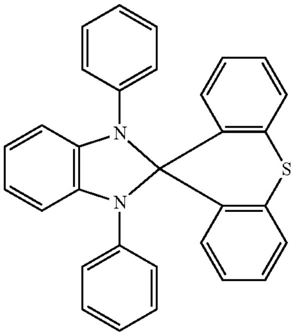
126
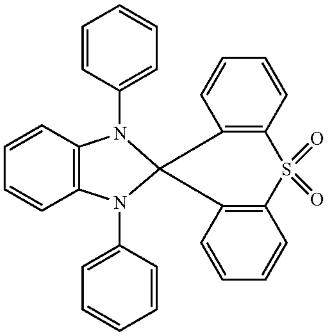
127
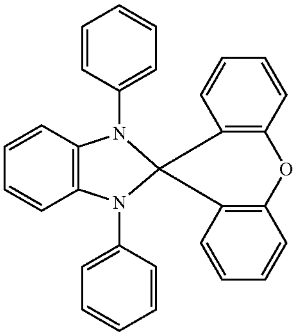
128
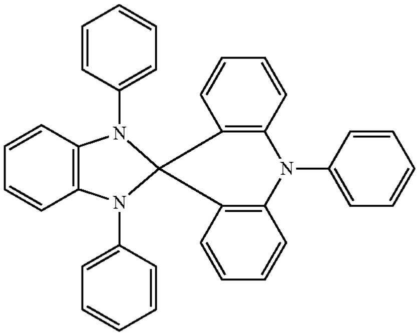

-continued
129
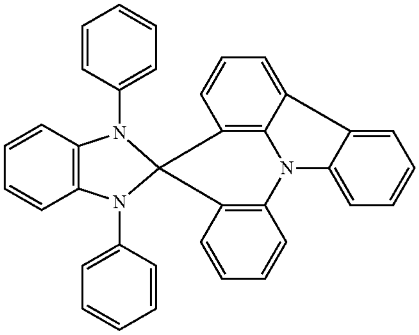
130
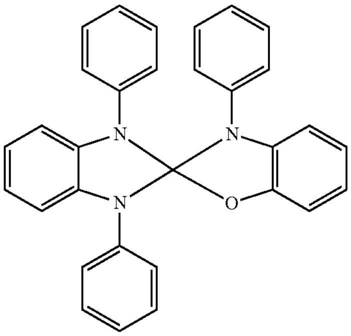
131
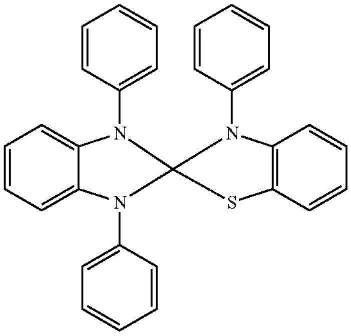
132
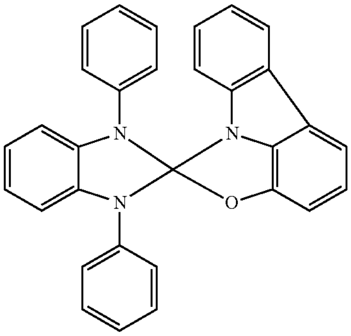
-continued
133
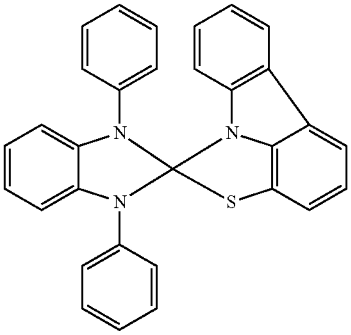
134
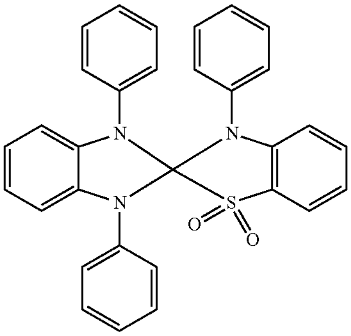
135
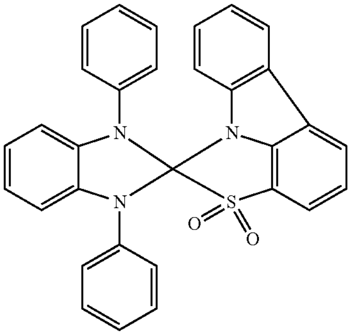
136
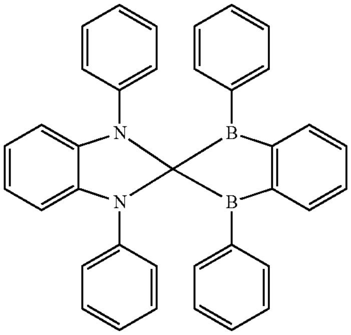

-continued

137

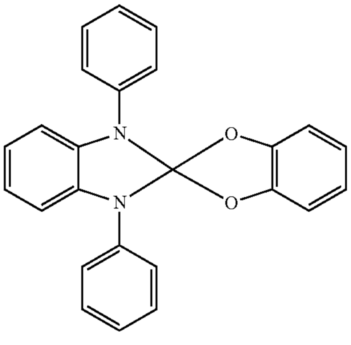

138

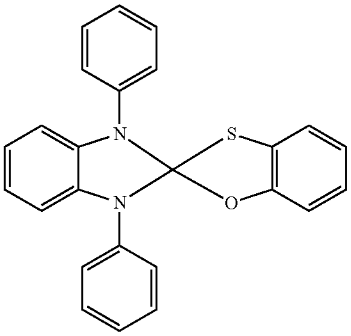

139

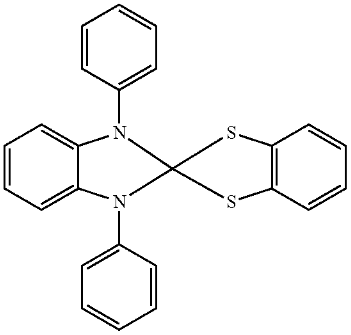

140

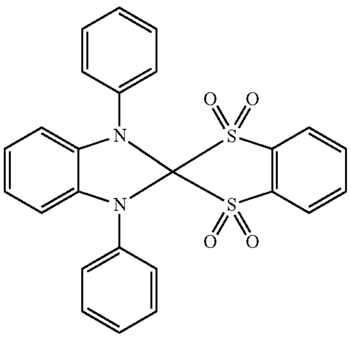

Preferred embodiments of compounds of the invention are recited in detail in the examples, these compounds being usable alone or in combination with further compounds for all purposes of the invention.

Provided that the conditions specified in claim 1 are met, the abovementioned preferred embodiments can be combined with one another as desired. In a particularly preferred embodiment of the invention, the abovementioned preferred embodiments apply simultaneously.

The compounds of the invention are preparable in principle by various processes. However, the processes described hereinafter have been found to be particularly suitable.

Therefore, the present invention further provides a process for preparing the compounds of the invention, in which a base skeleton having two aromatic amino groups is synthesized and this is then converted to a compound of formula (I) by means of a nucleophilic aromatic substitution reaction, a nucleophilic addition reaction or a coupling reaction.

Suitable compounds comprising at least one base skeleton having two aromatic amino groups are in many cases commercially available, and the starting compounds detailed in the examples are obtainable by known processes, and so reference is made thereto.

These compounds can be reacted with further compounds comprising at least one aromatic or heteroaromatic group by known coupling reactions, the necessary conditions for this purpose being known to the person skilled in the art, and detailed specifications in the examples assisting the person skilled in the art in conducting these reactions.

Particularly suitable and preferred coupling reactions which all lead to C—C bond formations and/or C—N bond formations are those according to BUCHWALD, SUZUKI, YAMAMOTO, STILLE, HECK, NEGISHI, SONOGASHIRA and HIYAMA. These reactions are widely known, and the examples will provide the person skilled in the art with further pointers.

The principles of the preparation processes detailed above are known in principle from the literature for similar compounds and can be adapted easily by the person skilled in the art for the preparation of the compounds of the invention. Further information can be found in the examples.

In addition, the compounds of the invention can be obtained by conversion of benzophenone imine derivatives, as set out in detail in the examples. One description of methods of this kind for preparation of other compounds is given by P.-Y. Gu et al., in Dyes and Pigments, 2016, 131, 224.

It is possible by these methods, if necessary followed by purification, for example recrystallization or sublimation, to obtain the compounds of the invention in high purity, preferably more than 99% (determined by means of $^{1}H$ NMR and/or HPLC).

The compounds of the invention may also be mixed with a polymer. It is likewise possible to incorporate these compounds covalently into a polymer. This is especially possible with compounds substituted by reactive leaving groups such as bromine, iodine, chlorine, boronic acid or boronic ester, or by reactive polymerizable groups such as olefins or oxetanes. These may find use as monomers for production of corresponding oligomers, dendrimers or polymers. The oligomerization or polymerization is preferably effected via the halogen functionality or the boronic acid functionality or via the polymerizable group. It is additionally possible to crosslink the polymers via groups of this kind. The compounds and polymers of the invention may be used in the form of a crosslinked or uncrosslinked layer.

The invention therefore further provides oligomers, polymers or dendrimers containing one or more of the above-detailed structures of the formula (I) and preferred embodiments of this formula or compounds of the invention, wherein one or more bonds of the compounds of the invention or of the structures of the formula (I) and preferred embodiments of that formula to the polymer, oligomer or dendrimer are present. According to the linkage of the structures of the formula (I) and preferred embodiments of this formula or of the compounds, these therefore form a side chain of the oligomer or polymer or are bonded within the main chain. The polymers, oligomers or dendrimers may be conjugated, partly conjugated or nonconjugated. The oligomers or polymers may be linear, branched or dendritic. For the repeat units of the compounds of the invention in oligomers, dendrimers and polymers, the same preferences apply as described above.

For preparation of the oligomers or polymers, the monomers of the invention are homopolymerized or copolymerized with further monomers. Preference is given to copolymers wherein the units of formula (I) or the preferred embodiments recited above and hereinafter are present to an extent of 0.01 to 99.9 mol %, preferably 5 to 90 mol %, more preferably 20 to 80 mol %. Suitable and preferred comonomers which form the polymer base skeleton are chosen from fluorenes (for example according to EP 842208 or WO 2000/022026), spirobifluorenes (for example according to EP 707020, EP 894107 or WO 2006/061181), paraphenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units.

Additionally of particular interest are compounds of the invention which feature a high glass transition temperature. In this connection, preference is given especially to compounds of the invention comprising structures of the formula (I) or the preferred embodiments recited above and hereinafter which have a glass transition temperature of at least 70° C., more preferably of at least 110° C., even more preferably of at least 125° C. and especially preferably of at least 150° C., determined in accordance with DIN 51005 (2005-08 version).

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, 2-methylbiphenyl, 3-methylbiphenyl, 1-methylnaphthalene, 1-ethylnaphthalene, ethyl octanoate, diethyl sebacate, octyl octanoate, heptylbenzene, menthyl isovalerate, cyclohexyl hexanoate or mixtures of these solvents.

The present invention therefore further provides a formulation or a composition comprising at least one compound of the invention and at least one further compound. The further compound may, for example, be a solvent, especially one of the abovementioned solvents or a mixture of these solvents. If the further compound comprises a solvent, this mixture is referred to herein as formulation. The further compound may alternatively be at least one further organic or inorganic compound which is likewise used in the electronic device, for example an emitter and/or a matrix material, where these compounds differ from the compounds of the invention. Suitable emitters and matrix materials are listed at the back in connection with the organic electroluminescent device. The further compound may also be polymeric.

The present invention therefore still further provides a composition comprising a compound of the invention and at least one further organofunctional material. Functional materials are generally the organic or inorganic materials introduced between the anode and cathode. Preferably, the organically functional material is selected from the group consisting of fluorescent emitters, phosphorescent emitters, emitters that exhibit TADF (thermally activated delayed fluorescence), host materials, electron transport materials, electron injection materials, hole conductor materials, hole injection materials, electron blocker materials, hole blocker materials, wide bandgap materials and n-dopants.

The present invention further provides for the use of a compound of the invention in an electronic device, especially in an organic electroluminescent device, preferably as host material, preferably as host material for phosphorescent emitters or as host material for emitters that exhibit TADF (thermally activated delayed fluorescence), as electron transport material, as electron injection material, as hole transport material, as hole injection material, as electron blocker material and/or as hole blocker material. Preferably, the compound of the invention may be used as host material, preferably as host material for phosphorescent emitters or as host material for emitters that exhibit TADF (thermally activated delayed fluorescence), for blue-emitting emitters, especially as blue-emitting phosphorescent emitters.

With regard to the end use of the present compounds, it should be emphasized that these fundamentally lead to an improvement in the desired properties, especially with regard to efficiency and operating voltage, as set out in detail in the examples. The base structure detailed in the claims in many cases leads to a material of good suitability as host material or as hole transport material. By appropriate substitution with electron-conducting groups, especially with a nitrogen-comprising base structure as shown in formulae (IIIa) to (IIIe) inter alia, it is possible to obtain compounds that have excellent properties as electron transport material and/or as hole blocker material.

The present invention still further provides an electronic device comprising at least one compound of the invention. An electronic device in the context of the present invention is a device comprising at least one layer comprising at least one organic compound. This component may also comprise inorganic materials or else layers formed entirely from inorganic materials.

The electronic device is preferably selected from the group consisting of organic electroluminescent devices (OLEDs, sOLED, PLEDs, LECs, etc.), preferably organic light-emitting diodes (OLEDs), organic light-emitting diodes based on small molecules (sOLEDs), organic light-emitting diodes based on polymers (PLEDs), light-emitting electrochemical cells (LECs), organic laser diodes (O-laser), organic plasmon-emitting devices (D. M. Koller et al., *Nature Photonics* 2008, 1-4), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs) and organic electrical sensors, preferably organic electroluminescent devices (OLEDs, sOLED, PLEDs, LECs, etc.), more preferably organic light-emitting diodes (OLEDs), organic light-emitting diodes based on small molecules (sOLEDs), organic light-emitting diodes based on polymers (PLEDs), especially phosphorescent OLEDs.

The organic electroluminescent device comprises cathode, anode and at least one emitting layer. Apart from these layers, it may also comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are systems having three emitting layers, where the three layers show blue, green and orange or red emission. The organic electroluminescent device of the invention may also be a tandem electroluminescent device, especially for white-emitting OLEDs.

The compound of the invention may be used in different layers, according to the exact structure. Preference is given to an organic electroluminescent device comprising a compound of formula (I) or the above-detailed preferred embodiments in an emitting layer as host material that provides hole-conducting properties, preferably as host material for blue emitters, more preferably blue triplet emitters.

Preference is given to an organic electroluminescent device comprising a compound of formula (I) or the preferred embodiments detailed above as hole transport material, hole injection material and/or as electron blocker layer, preferably in a hole transport layer, hole injection layer and/or electron blocker layer.

When the compound of the invention is used as matrix material for a phosphorescent compound in an emitting layer, it is preferably used in combination with one or more phosphorescent materials (triplet emitters). Phosphorescence in the context of this invention is understood to mean luminescence from an excited state having higher spin multiplicity, i.e. a spin state >1, especially from an excited triplet state. In the context of this application, all luminescent complexes with transition metals or lanthanides, especially all iridium, platinum and copper complexes, shall be regarded as phosphorescent compounds.

The mixture of the compound of the invention and the emitting compound contains between 99% and 1% by volume, preferably between 98% and 10% by volume, more preferably between 97% and 60% by volume and especially between 95% and 80% by volume of the compound of the invention, based on the overall mixture of emitter and matrix material. Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material.

In one embodiment of the invention, the compound of the invention is used here as the sole matrix material ("single host") for the phosphorescent emitter.

In a preferred embodiment of the invention, the organic electroluminescent device contains the compound of the invention, preferably a compound comprising structures of formula (I), (IIa) to (IId), (IIIa) to (IIIe), (IVa) to (IVd), (Va) to (Ve) and/or (VIa) to (VId) or the above-detailed preferred embodiments as matrix material, preferably as hole-conducting matrix material, in one or more emitting layers, preferably in combination with a further matrix material, preferably an electron-conducting matrix material. In a further preferred embodiment of the invention, the further matrix material is a hole-transporting compound. In yet a further preferred embodiment, the further matrix material is a compound having a large band gap which is not involved to a significant degree, if at all, in the hole and electron transport in the layer. An emitting layer comprises at least one emitting compound.

Suitable matrix materials which can be used in combination with the inventive compounds are aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527, WO 2008/086851 or WO 2013/041176, indolocarbazole derivatives, for example according to WO 2007/063754 or WO 2008/056746, indenocarbazole derivatives, for example according to WO 2010/136109, WO 2011/000455, WO 2013/041176 or WO 2013/056776, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2007/063754, WO 2008/056746, WO 2010/015306, WO 2011/057706, WO 2011/060859 or WO 2011/060877, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to WO 2011/042107, WO 2011/060867, WO 2011/088877 and WO 2012/143080, triphenylene derivatives, for example according to WO 2012/048781, dibenzofuran derivatives, for example according to WO 2015/169412, WO 2016/015810, WO 2016/023608, WO 2017/148564 or WO 2017/148565, or biscarbazoles, for example according to JP 3139321 B2.

In addition, the co-host used may be a compound that does not take part in charge transport to a significant degree, if at all, as described, for example, in WO 2010/108579. Especially suitable in combination with the compound of the invention as co-matrix material are compounds which have a large bandgap and themselves take part at least not to a significant degree, if any at all, in the charge transport of the emitting layer. Such materials are preferably pure hydrocarbons. Examples of such materials can be found, for example, in WO 2009/124627 or in WO 2010/006680.

Phosphorescence in the context of this invention is understood to mean luminescence from an excited state having higher spin multiplicity, i.e. a spin state >1, especially from an excited triplet state. In the context of this application, all luminescent complexes with transition metals or lanthanides, especially all iridium, platinum and copper complexes, shall be regarded as phosphorescent compounds.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum.

Examples of the above-described phosphorescent organometallic complexes can be found in applications WO00/70655, WO2001/41512, WO2002/02714, WO2002/15645, EP1191612, WO2005/033244, WO2005/019373, US2005/0258742, WO2006/056418, WO2007/115970, WO2007/115981, WO2008/000727, WO2009/050281, WO2009/050290, WO2011/051404, WO2011/073149, WO2012/121936, US2012/0305894, WO2012/170571, WO2012/170461, WO2012/170463, WO2006/121811, WO2007/095118, WO2008/156879, WO2008/156879, WO2010/068876, WO2011/106344, WO2012/172482, EP3126371, WO2015/014835, WO2015/014944, WO2016/020516, US2016/0072081, WO2010/086089, WO2011/044988, WO2014/008982, WO2014/023377, WO2014/094961, WO2010/069442, WO2012/163471, WO2013/020631, US2015/0243912, WO2008/000726, WO2010/015307, WO2010/054731, WO2010/054728, WO2010/099852, WO2011/032626, WO2011/157339, WO2012/007086, WO2015/036074, WO2015/104045, WO2015/117718, WO2016/015815. In general, all phosphorescent complexes as used for phosphorescent electroluminescent devices according to the prior art and as known to those skilled in the art in the field of organic electroluminescence are suitable, and the person skilled in the art will be able to use further phosphorescent complexes without exercising inventive skill.

Further examples of phosphorescent emitters are organometallic complexes having polypodal ligands as described in WO2004081017, WO2005042550, US20050170206, WO2009/146770, WO2010/102709, WO2011/066898, WO2016124304, WO2017032439, WO2018019688, EP3184534, WO2018/011186, WO 2016/193243 and WO 2015/091716A1.

These additionally also include binuclear organometallic complexes as described in WO2011/045337, US2015/0171350, WO2016/079169, WO2018/019687, WO2018/041769, WO2018/054798, WO2018/069196, WO2018/069197, WO2018/069273.

These additionally also include copper complexes as described in WO2010/031485, US2013/150581, WO2013/017675, WO2013/007707, WO2013/001086, WO2012/156378, WO2013/072508, EP2543672.

Examples of suitable phosphorescent palladium complexes are described in WO2014/109814.

In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Explicit examples of phosphorescent compounds are $Ir(ppy)_3$ and its derivatives, and the structures detailed in the overviews that follow.

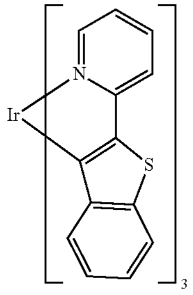
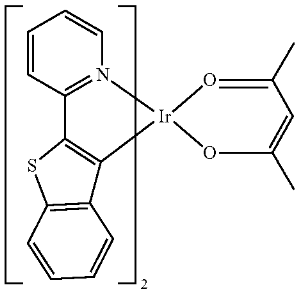
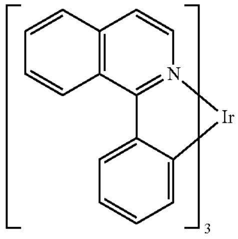
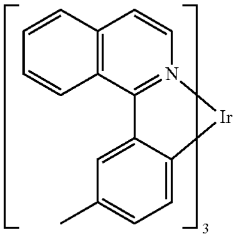
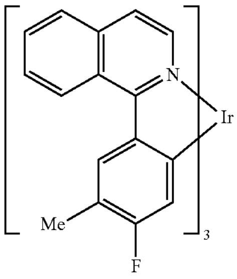
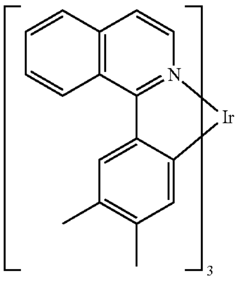
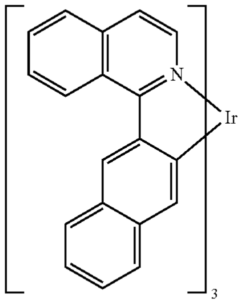
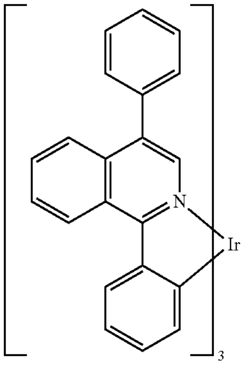
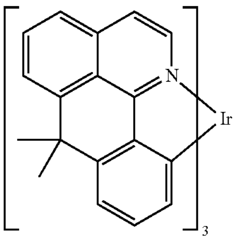
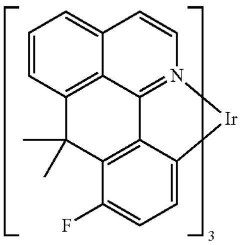

-continued
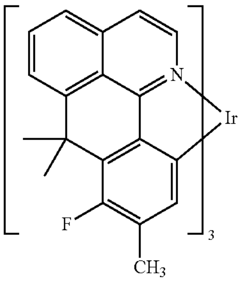
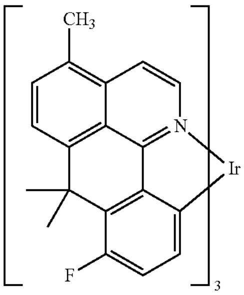
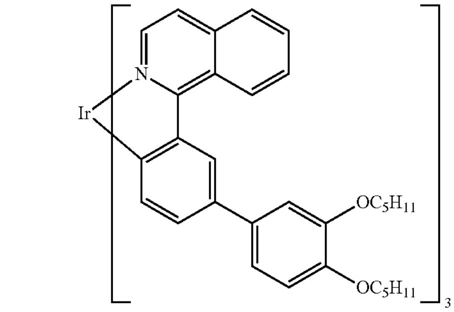
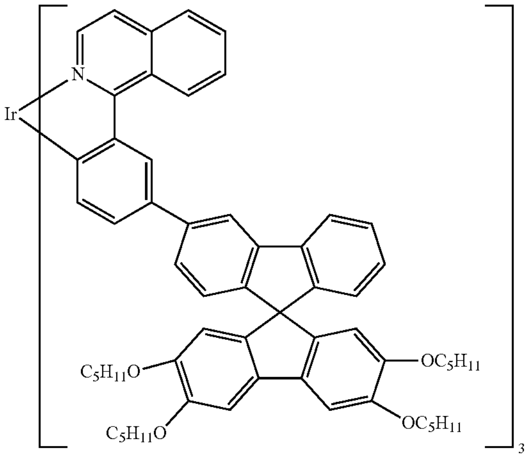
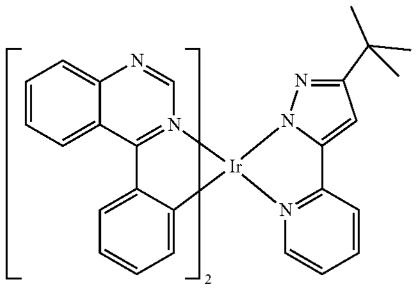
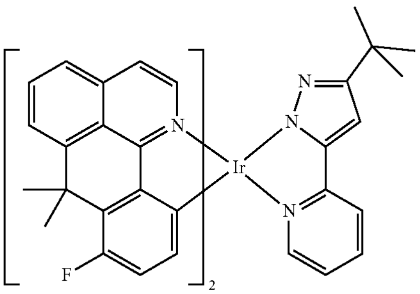
-continued
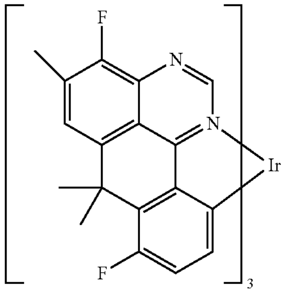
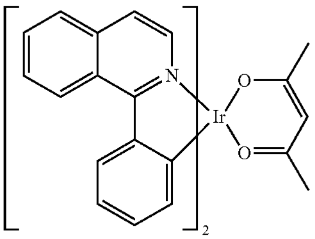
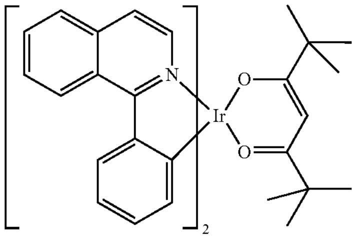
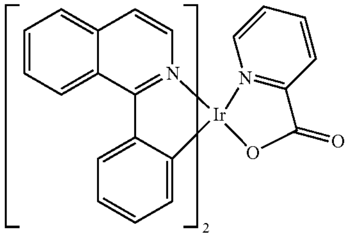
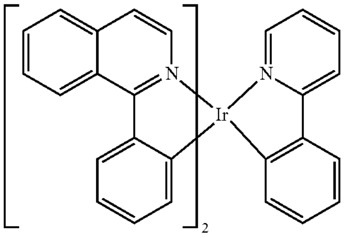
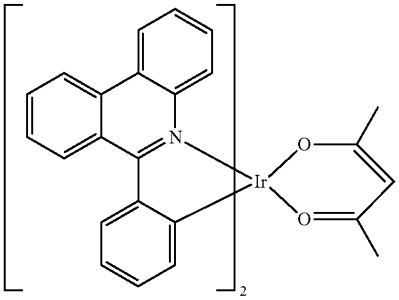

-continued
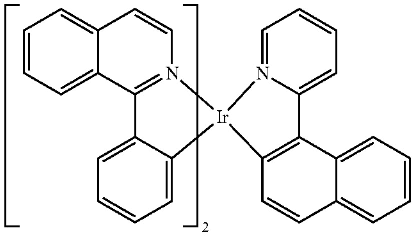
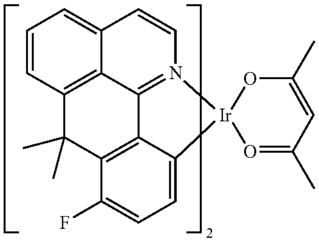
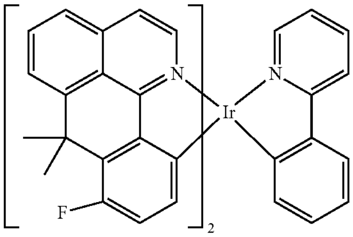
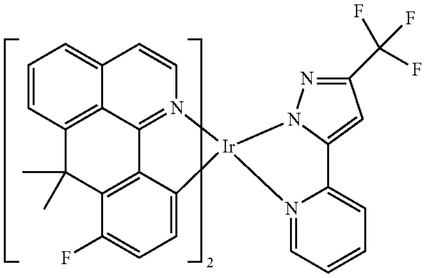
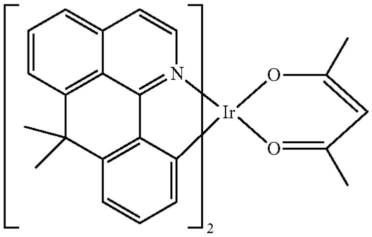
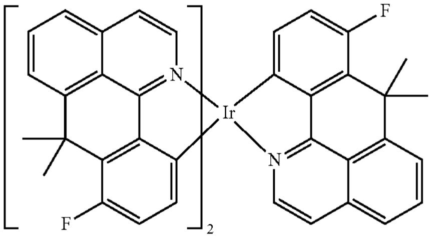
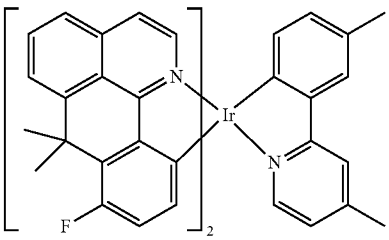
-continued
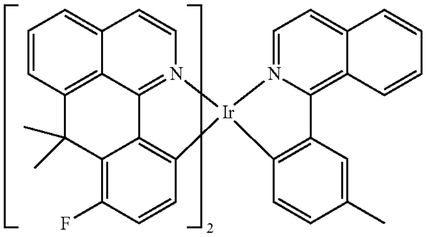
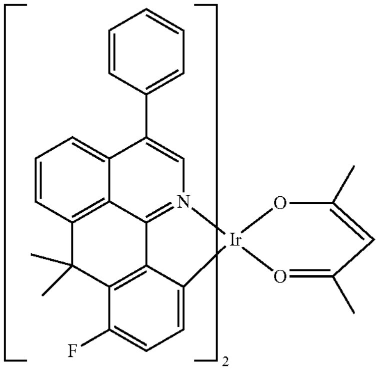
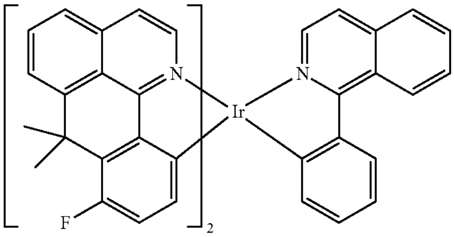
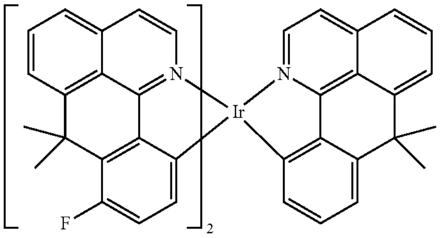
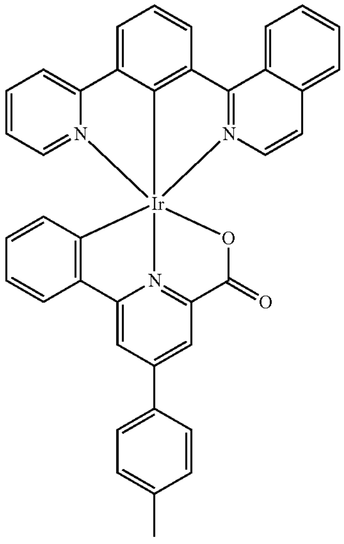

-continued
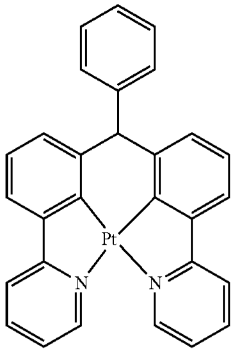
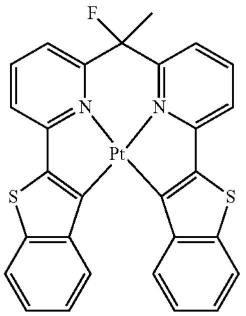
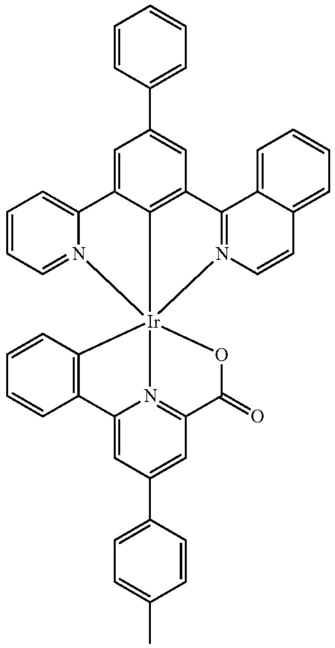
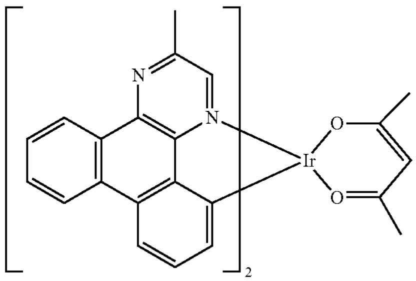
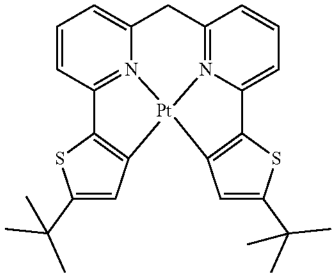
-continued
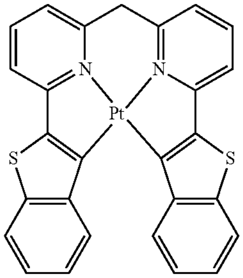
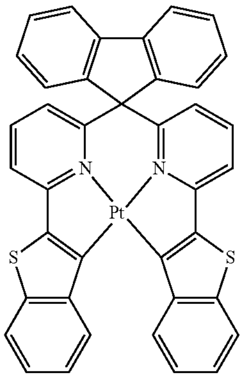
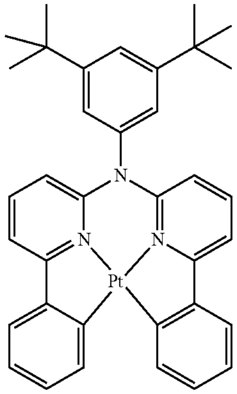
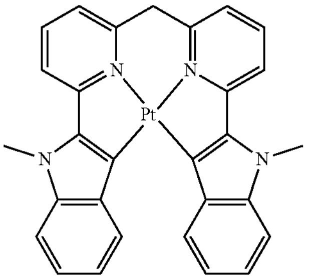
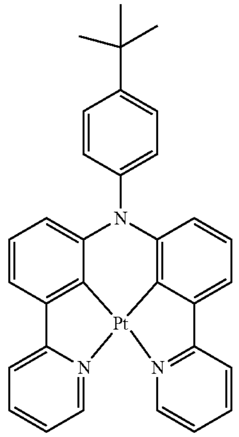
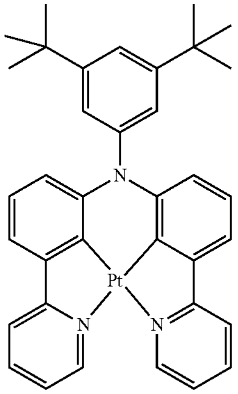
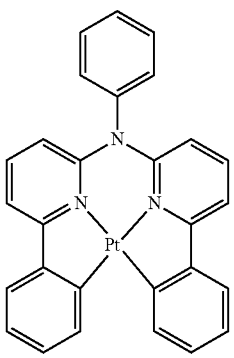
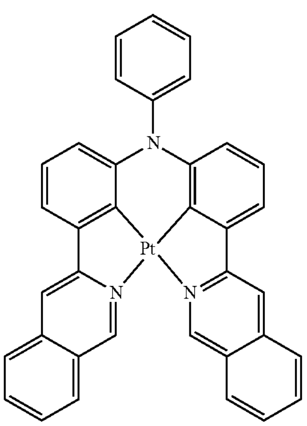

-continued
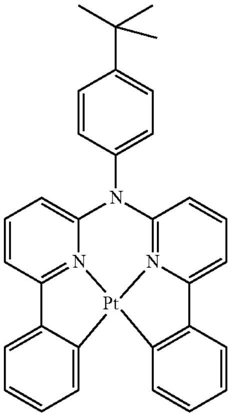
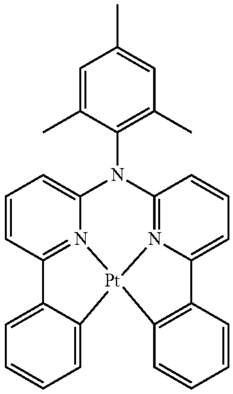
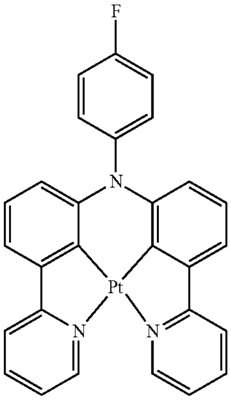
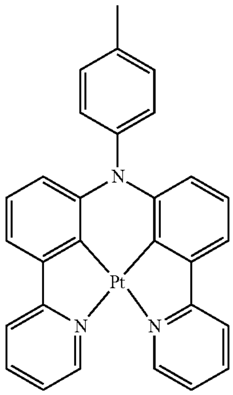
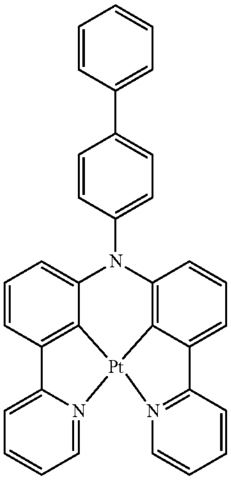
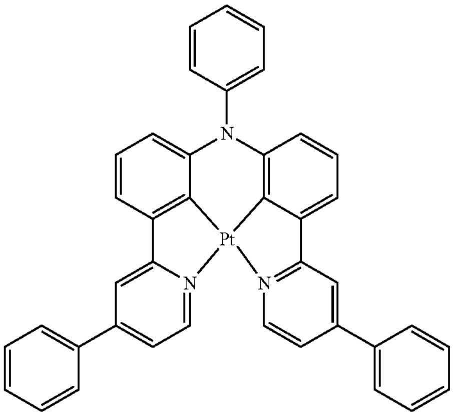
-continued
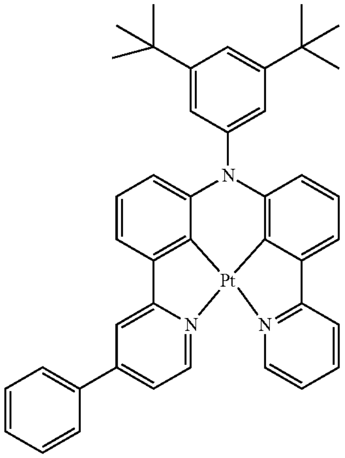
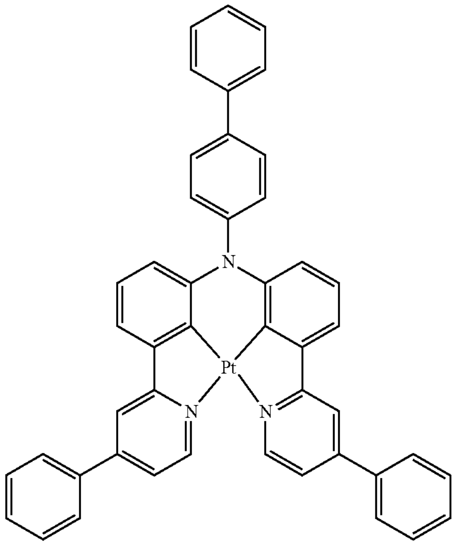
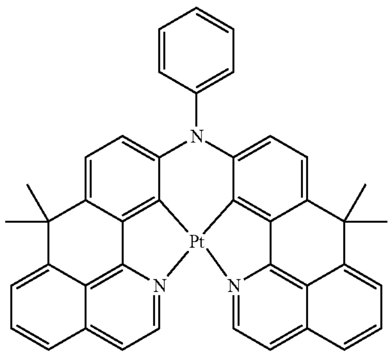

-continued
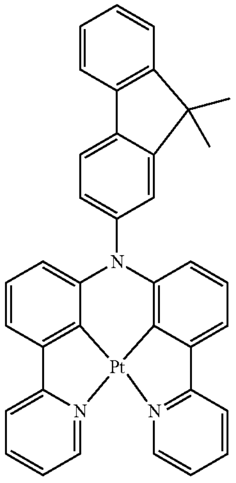
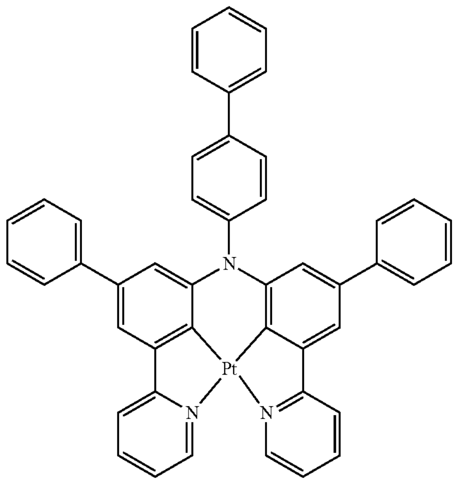
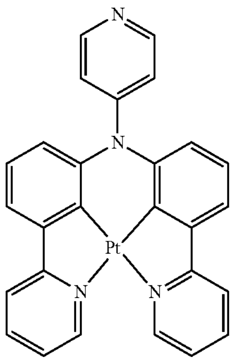
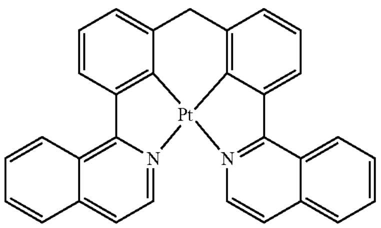
-continued
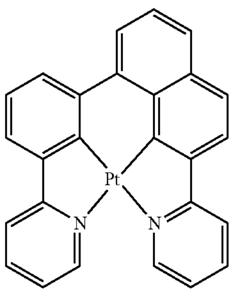
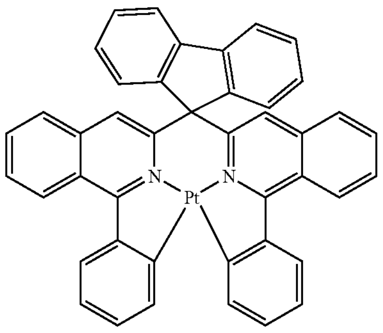
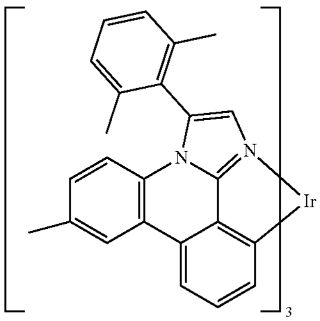
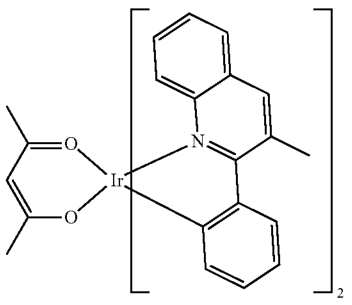
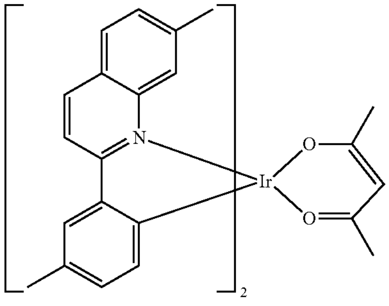

-continued
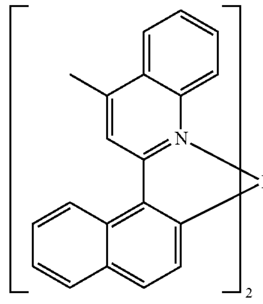
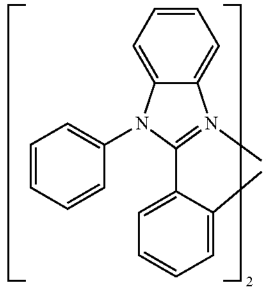
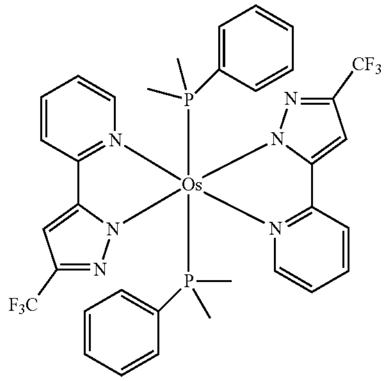
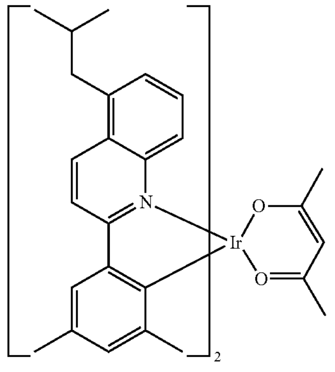
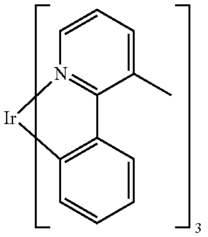
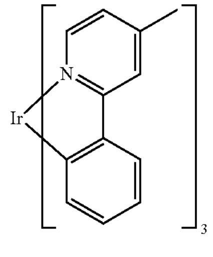
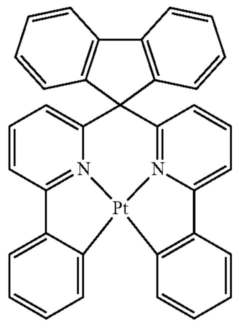
-continued
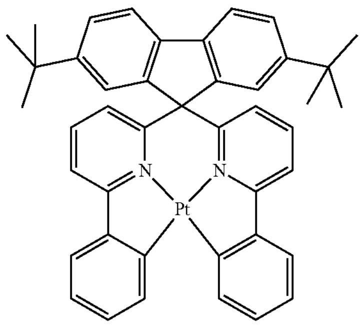
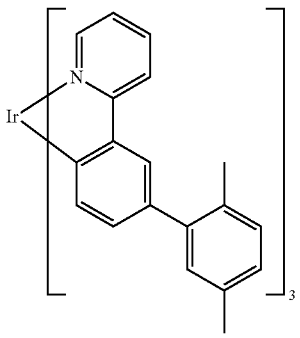
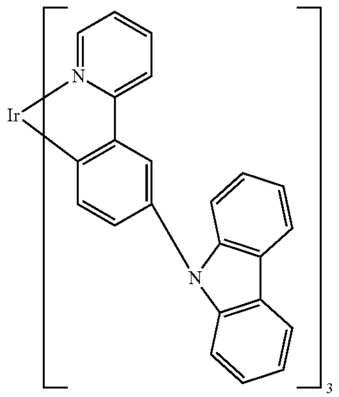
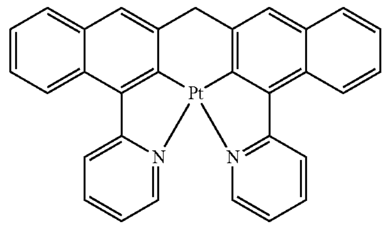
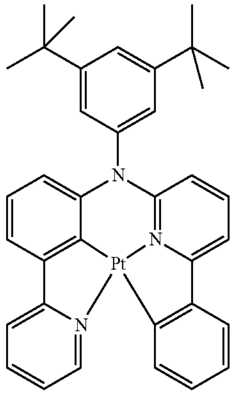

-continued
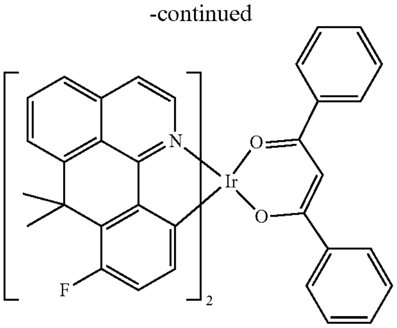
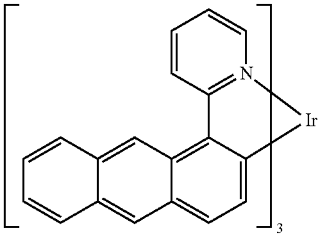
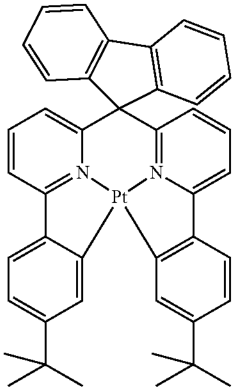
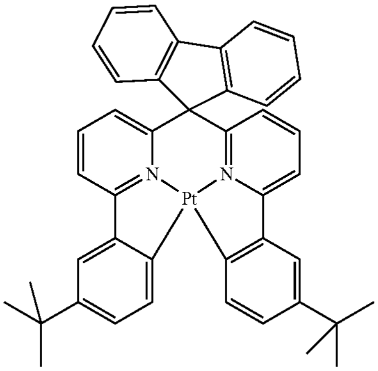
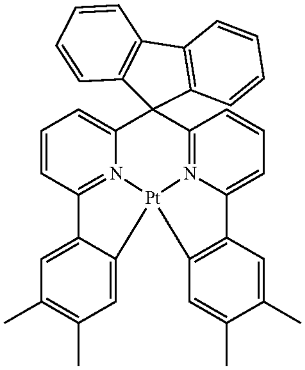
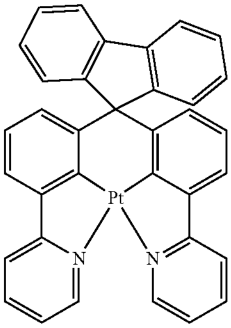
-continued
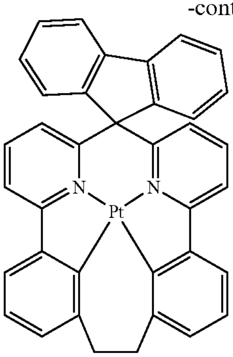
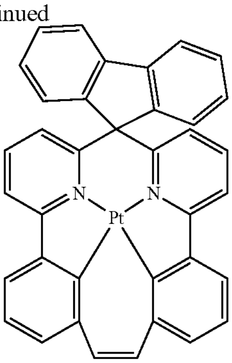
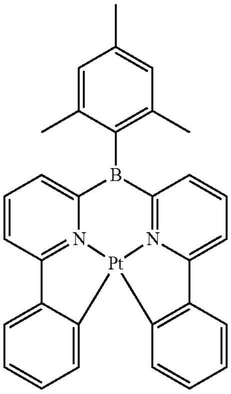
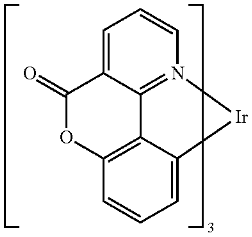
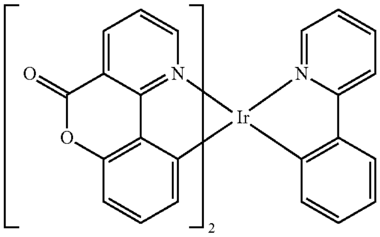
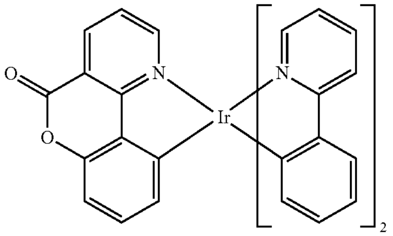
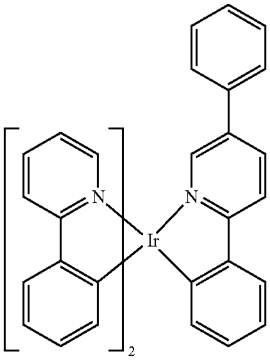

-continued
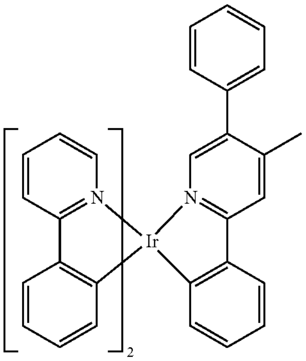
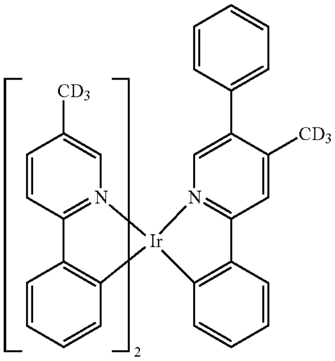
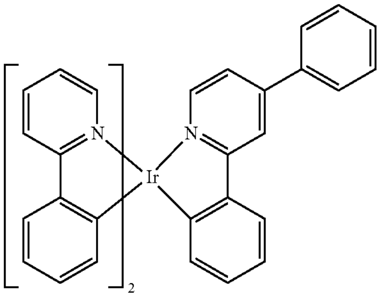
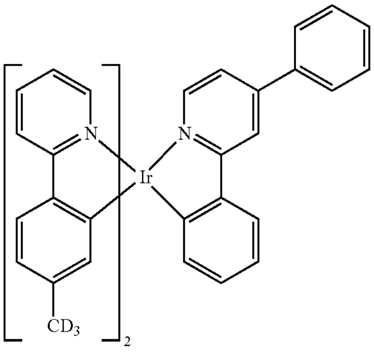
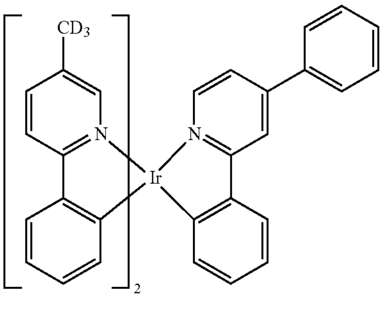
-continued
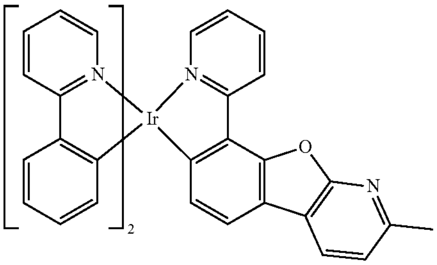
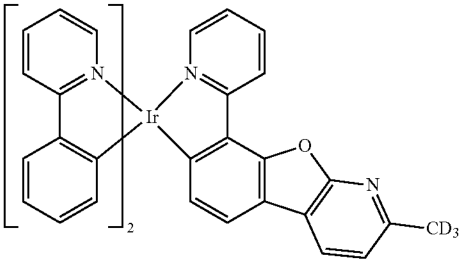
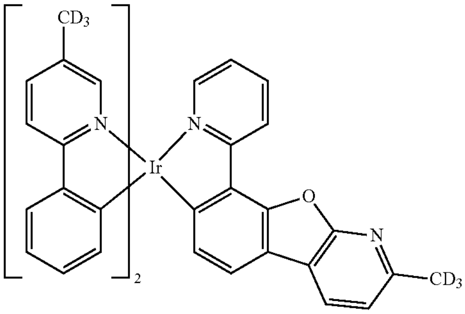
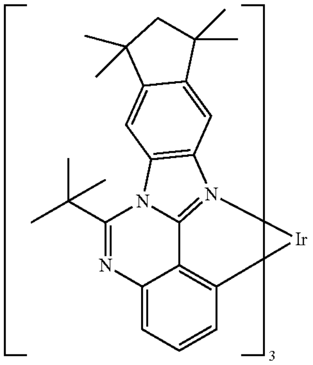
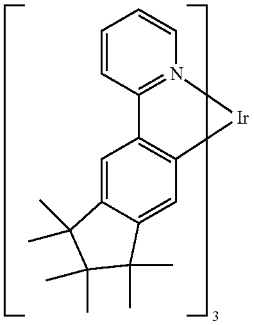
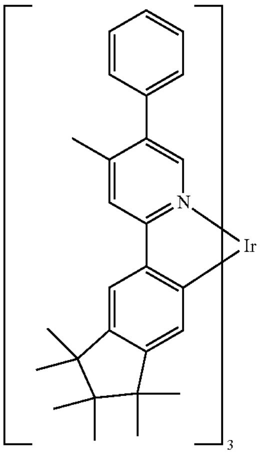

-continued
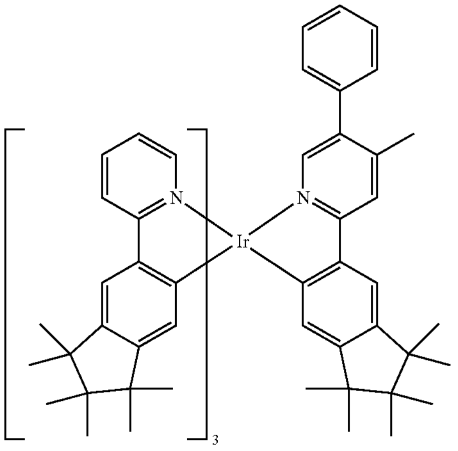
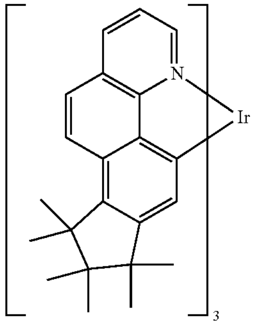
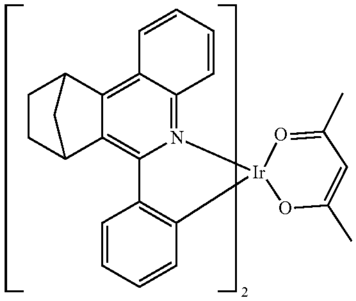
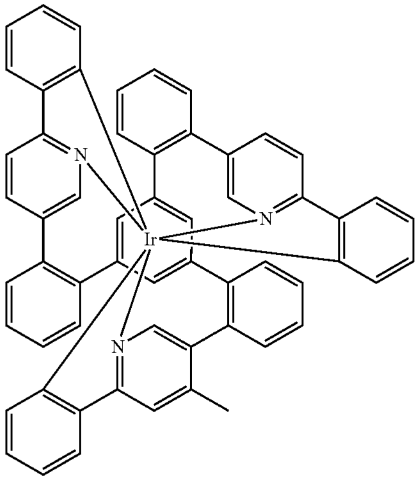
-continued
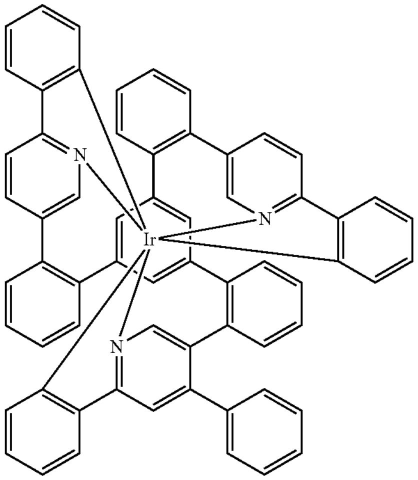
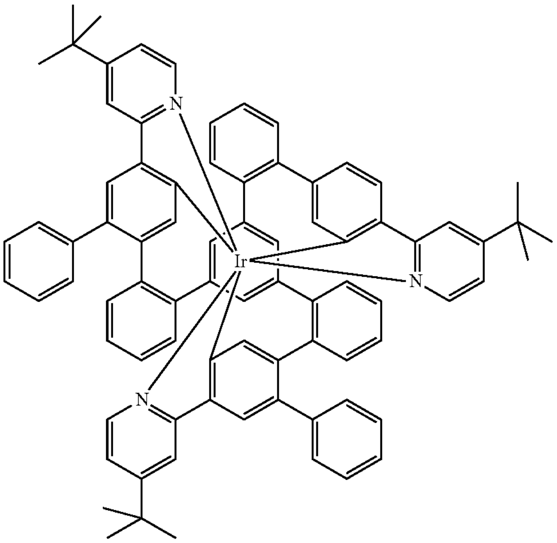
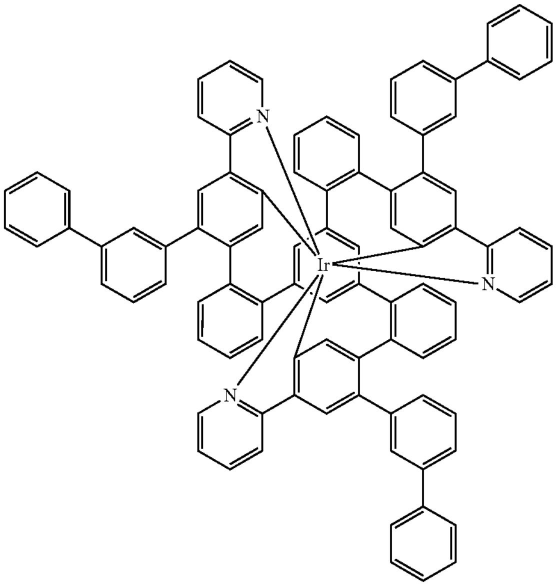

-continued

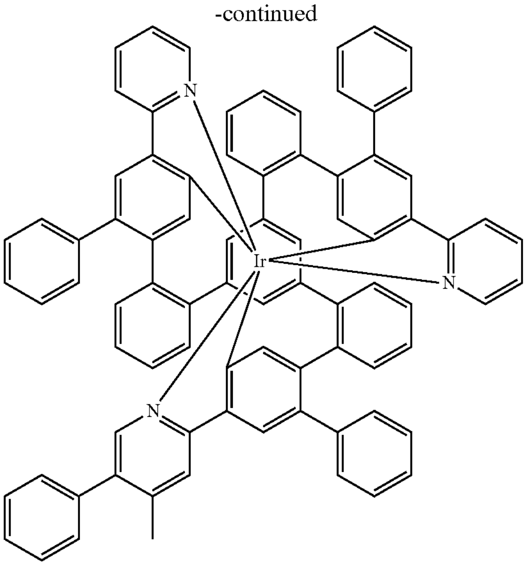

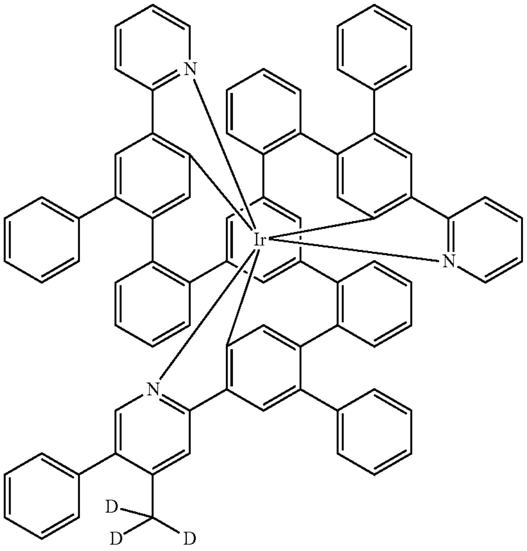

The compounds of the invention are especially also suitable as matrix materials for phosphorescent emitters in organic electroluminescent devices, as described, for example, in WO 98/24271, US 2011/0248247 and US 2012/0223633. In these multicolor display components, an additional blue emission layer is applied by vapor deposition over the full area to all pixels, including those having a color other than blue.

A compound of the invention may preferably be used in combination with a TADF emitter, as set out above.

The process referred to as thermally activated delayed fluorescence (TADF) is described, for example, by B. H. Uoyama et al., Nature 2012, Vol. 492, 234. In order to enable this process, a comparatively small singlet-triplet separation $\Delta E(S_1\text{-}T_1)$ of less than about 2000 $cm^{-1}$, for example, is needed in the emitter. In order to open up the $T_1 \rightarrow S_1$ transition which is spin-forbidden in principle, as well as the emitter, it is possible to provide a further compound in the matrix that has strong spin-orbit coupling, such that intersystem crossing is enabled via the spatial proximity and the interaction which is thus possible between the molecules, or the spin-orbit coupling is generated by means of a metal atom present in the emitter.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In the further layers of the organic electroluminescent device of the invention, it is possible to use any materials as typically used according to the prior art. The person skilled in the art will therefore be able, without exercising inventive skill, to use any materials known for organic electroluminescent devices in combination with the inventive compounds of formula (I) or the above-recited preferred embodiments.

Additionally preferred is an organic electroluminescent device, characterized in that one or more layers are coated by a sublimation process. In this case, the materials are applied by vapour deposition in vacuum sublimation systems at an initial pressure of less than $10^{-5}$ mbar, preferably less than $10^{-6}$ mbar. However, it is also possible that the initial pressure is even lower, for example less than $10^{-7}$ mbar.

Preference is likewise given to an organic electroluminescent device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vaporjet printing) method, in which the materials are applied directly by a nozzle and thus structured.

Preference is additionally given to an organic electroluminescent device, characterized in that one or more layers are produced from solution, for example by spin-coating, or by any printing method, for example screen printing, flexographic printing, offset printing, LITI (light-induced thermal imaging, thermal transfer printing), inkjet printing or nozzle printing. For this purpose, soluble compounds are needed, which are obtained, for example, through suitable substitution.

Formulations for applying a compound of formula (I) or the preferred embodiments thereof detailed above are novel. The present invention therefore further provides formulations containing at least one solvent and a compound according to formula (I) or the preferred embodiments thereof detailed above.

In addition, hybrid methods are possible, in which, for example, one or more layers are applied from solution and one or more further layers are applied by vapour deposition.

Those skilled in the art are generally aware of these methods and are able to apply them without exercising inventive skill to organic electroluminescent devices comprising the compounds of the invention.

The compounds of the invention and the organic electroluminescent devices of the invention have the particular feature of an improved lifetime over the prior art. At the same time, the further electronic properties of the electroluminescent devices, such as efficiency or operating voltage, remain at least equally good. In a further variant, the compounds of the invention and the organic electroluminescent devices of the invention especially feature improved efficiency and/or operating voltage and higher lifetime compared to the prior art.

The electronic devices of the invention, especially organic electroluminescent devices, are notable for one or more of the following surprising advantages over the prior art:

1. Electronic devices, especially organic electroluminescent devices, comprising compounds, oligomers, polymers or dendrimers or the preferred embodiments recited above and hereinafter, especially as electron-conducting materials, as hole transport materials or as matrix materials, more preferably as hole transport materials or as matrix materials, have a very good lifetime.
2. Electronic devices, especially organic electroluminescent devices, comprising inventive compounds, oligomers, polymers or dendrimers or the preferred embodiments recited above and hereinafter, especially as electron transport materials, hole transport materials and/or as host materials, more preferably as hole transport materials and/or as matrix materials, have excellent efficiency. More particularly, efficiency is much higher compared to analogous compounds containing no structure of the invention. In this context, the compounds, oligomers, polymers or dendrimers of the invention or the preferred embodiments recited above and hereinafter bring about a low operating voltage when used in electronic devices. In this context, these compounds especially bring about low roll-off, i.e. a small drop in power efficiency of the device at high luminances.
3. The inventive compounds of formula (I) or the preferred embodiments recited above and hereinafter exhibit very high stability and lifetime.
4. Electronic devices, especially organic electroluminescent devices, comprising compounds, oligomers, polymers or dendrimers or the preferred embodiments recited above and hereinafter as electron transport materials, hole transport materials and/or as host materials, especially preferably as hole transport materials and/or as matrix materials, have excellent color purity.
6. Compounds comprising structures of formula (I), preferably compounds of the formula (I) or the preferred embodiments recited above and hereinafter, have excellent glass film formation.
7. Compounds comprising structures of formula (I), preferably compounds of the formula (I) or the preferred embodiments recited above and hereinafter, form very good films from solutions and show excellent solubility.
8. The compounds comprising structures of formula (I), preferably compounds of the formula (I) or the preferred embodiments recited above and hereinafter, have a high triplet level $T_1$.

These abovementioned advantages are not accompanied by an inordinately high deterioration in the further electronic properties.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Thus, any feature disclosed in the present invention, unless stated otherwise, should be considered as an example of a generic series or as an equivalent or similar feature.

All features of the present invention may be combined with one another in any manner, unless particular features and/or steps are mutually exclusive. This is especially true of preferred features of the present invention. Equally, features of non-essential combinations may be used separately (and not in combination).

It should also be pointed out that many of the features, and especially those of the preferred embodiments of the present invention, should themselves be regarded as inventive and not merely as some of the embodiments of the present invention. For these features, independent protection may be sought in addition to or as an alternative to any currently claimed invention.

The technical teaching disclosed with the present invention may be abstracted and combined with other examples.

The invention is illustrated in more detail by the examples which follow, without any intention of restricting it thereby. The person skilled in the art will be able to use the information given to execute the invention over the entire scope disclosed and to prepare further compounds of the invention without exercising inventive skill and to use them in electronic devices or to employ the process of the invention.

EXAMPLES

The syntheses which follow, unless stated otherwise, are conducted under a protective gas atmosphere in dried solvents. The metal complexes are additionally handled with exclusion of light or under yellow light. The solvents and reagents can be purchased, for example, from Sigma-ALDRICH or ABCR. The respective figures in square brackets or the numbers quoted for individual compounds relate to the CAS numbers of the compounds known from the literature. In the case of compounds that can have multiple enantiomeric, diastereomeric or tautomeric forms, one form is shown in a representative manner.

Synthesis of Synthons S:

Example S1

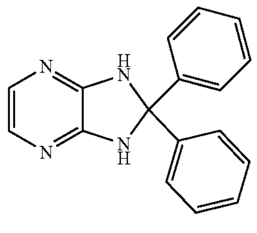 [SMILES: c1ccc(C2(c3ccccc3)Nc3nccnc3N2)cc1]

Procedure analogous to P.-Y. Gu et al., Dyes and Pigments, 2016, 131, 224.

A mixture of 15.0 g [100 mmol] of 2,3-dichloropyrazine [4858-85-9] and 54.3 g [300 mmol] of benzophenone imine [1013-88-3] in 500 ml DMSO is stirred at 160° C. for 24 h. The mixture is allowed to cool to 80° C., 20 ml of 10.2 molar aqueous HCl is added, and the mixture is heated again to 160° C. for 40 h. After cooling, the mixture is poured onto 2000 ml of degassed ice-water and stirred briefly, and the solids are filtered off with suction, washed three times with 100 ml each time of water and twice with 50 ml each time of methanol, and dried under reduced pressure. The crude product is subjected to flash chromatography, n-heptane/

DCM (dichloromethane), Torrent automated column system from A. Semrau. Yield: 15.4 g (56 mmol) 56%; purity about 95% by $^{1}H$ NMR.
The following compounds can be prepared analogously:
| Ex. | Reactants | Product | Yield |
|---|---|---|---|
| S2 | 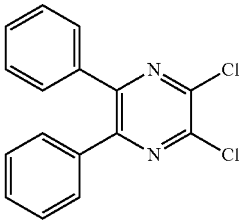 57038-62-7 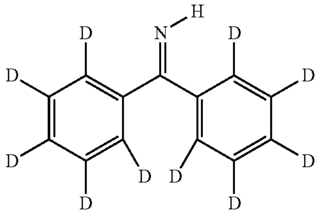 1170155-68-6 | 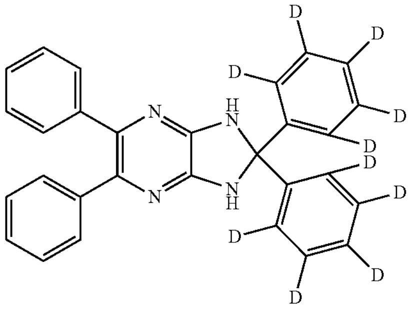 [SMILES: [2H]c1c([2H])c([2H])c(C2(c3c([2H])c([2H])c([2H])c([2H])c3[2H])Nc3nc(-c4ccccc4)c(-c4ccccc4)nc3N2)c([2H])c1[2H]] | 50% |
| S3 | 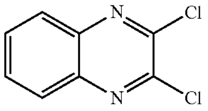 2213-63-0 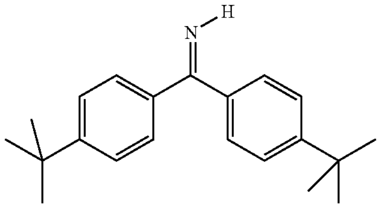 1455305-60-8 | 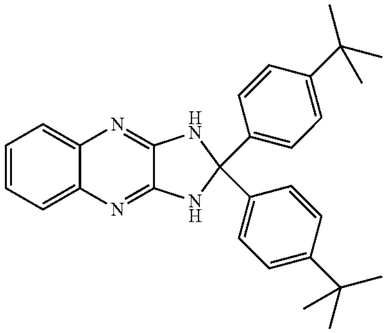 [SMILES: CC(C)(C)c1ccc(C2(c3ccc(C(C)(C)C)cc3)Nc3nc4ccccc4nc3N2)cc1] | 55% |
| S4 | 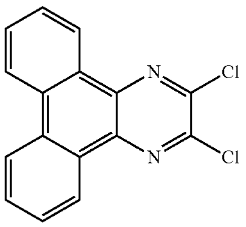 1874244-46-8 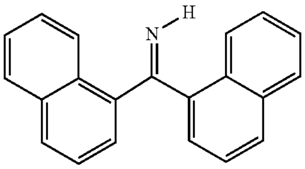 51167-88-5 | 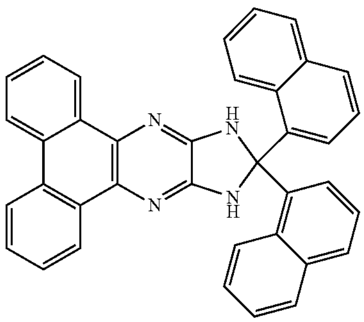 [SMILES: c1ccc2c(C3(c4cccc5ccccc45)Nc4nc5c6ccccc6c6ccccc6c5nc4N3)cccc2c1] | 44% |

-continued
| Ex. | Reactants | Product | Yield |
|---|---|---|---|
| S5 | 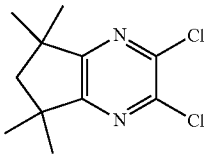<br>1311465-45-8<br>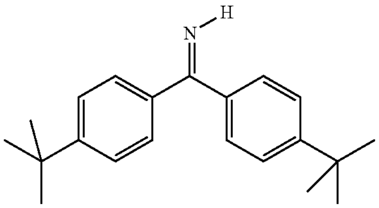<br>1455305-60-8 | 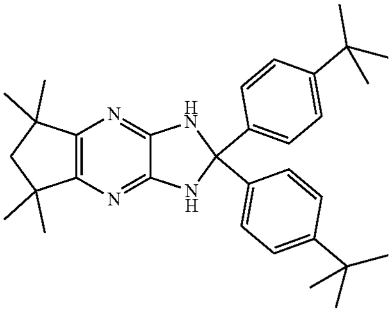 [SMILES: CC(C)(C)c1ccc(C2(c3ccc(C(C)(C)C)cc3)Nc3nc4c(nc3N2)C(C)(C)CC4(C)C)cc1] | 60% |
| S6 | 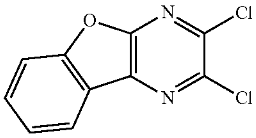<br>2144490-414<br>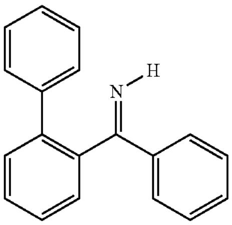 [SMILES: [H]/N=C(\c1ccccc1)c1ccccc1-c1ccccc1] | 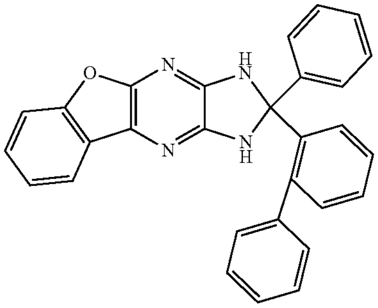 [SMILES: c1ccc(-c2ccccc2C2(c3ccccc3)Nc3nc4oc5ccccc5c4nc3N2)cc1] | 41% |
| S7 | 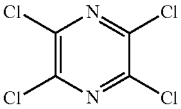<br>13484-50-9<br>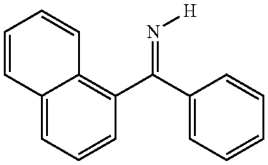<br>41839-61-6 | 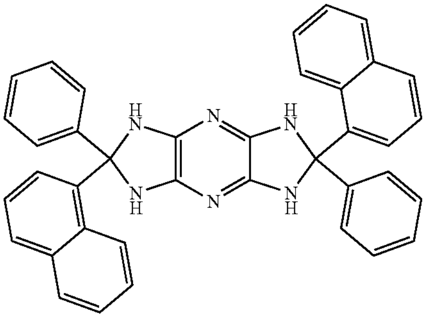 [SMILES: c1ccc(C2(c3cccc4ccccc34)Nc3nc4c(nc3N2)NC(c2ccccc2)(c2cccc3ccccc23)N4)cc1] | 49% |

-continued

| Ex. | Reactants | Product | Yield |
|---|---|---|---|
| S8 | 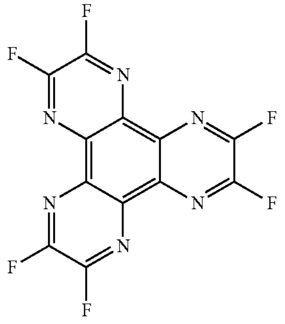<br>1192354-34-9<br>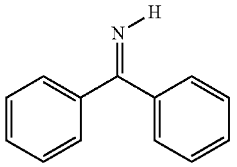<br>1013-88-3 | 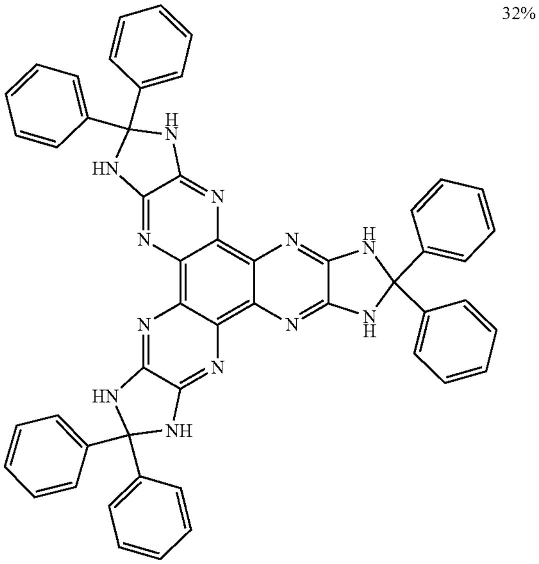 | 32% |

Example S50

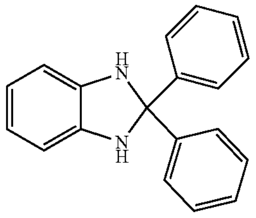 [SMILES: c1ccc(C2(c3ccccc3)Nc3ccccc3N2)cc1]

A well-stirred mixture of 23.6 g [100 mmol] of o-dibromobenzene [583-53-9], 54.3 g [300 mmol] of benzophenone imine [1013-88-3], 38.4 g [400 mmol] of sodium tert-butoxide [865-48-5], 2.5 g [4 mmol] of BINAP [98327-87-8], 898 mg [4 mmol] of palladium(II) acetate and 500 ml of toluene is heated under reflux for 1 h. After cooling, 500 ml is added, the mixture is stirred for 5 min., and the organic phase is removed, washed three times with 300 ml of water and once with saturated sodium chloride solution, and dried over magnesium sulfate. The desiccant is filtered off using a Celite bed in the form of a toluene slurry, and the filtrate is concentrated to dryness under reduced pressure. The residue is taken up in 500 ml of DMSO, 20 ml of 10.2 molar aqueous HCl is added, and the mixture is heated to 160° C. for 40 h. After cooling, the mixture is poured onto 2000 ml of degassed ice-water and stirred briefly, and the solids are filtered off with suction, washed three times with 100 ml each time of water and twice with 50 ml each time of methanol, and dried under reduced pressure. The crude product is subjected to flash chromatography, n-heptane/DCM (dichloromethane), Torrent automated column system from A. Semrau. Yield: 15.5 g (57 mmol) 57%; purity about 95% by $^{1}$H NMR.

The following compounds can be prepared analogously:

| Ex. | Reactants | Product | Yield |
|---|---|---|---|
| S51 | 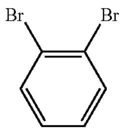<br>583-53-9<br>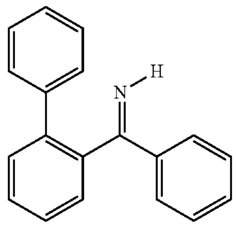<br>791001-66-6 | 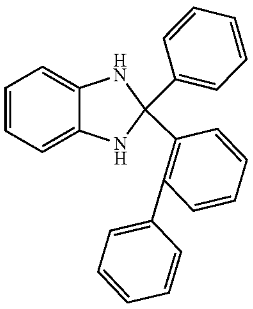 [SMILES: c1ccc(-c2ccccc2C2(c3ccccc3)Nc3ccccc3N2)cc1] | 48% |

-continued
| Ex. | Reactants | Product | Yield |
|---|---|---|---|
| S52 | 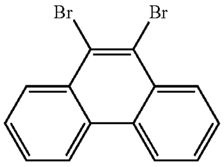<br>15810-15-8<br>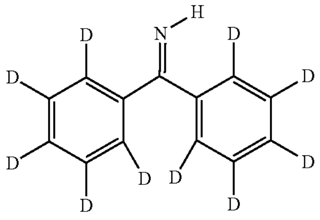<br>1170155-68-6 | 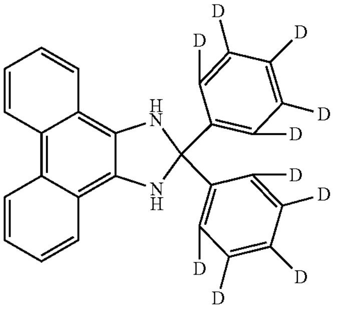 [SMILES: [2H]c1c([2H])c([2H])c(C2(c3c([2H])c([2H])c([2H])c([2H])c3[2H])Nc3c(c4ccccc4c4ccccc34)N2)c([2H])c1[2H]] | 60% |
| S53 | 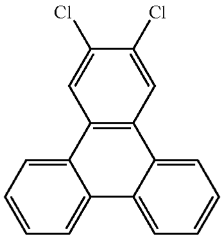<br>2271383-24-3<br>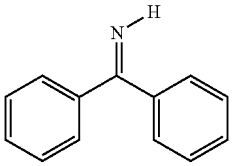<br>1013-88-3 | 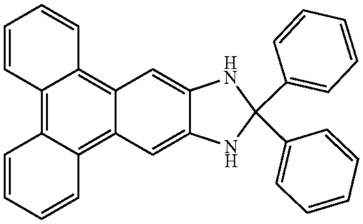 [SMILES: c1ccc(C2(c3ccccc3)Nc3cc4c5ccccc5c5ccccc5c4cc3N2)cc1] | 53% |
| S54 | 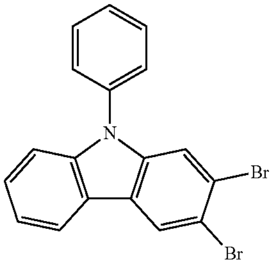<br>2375560-82-8<br>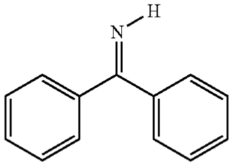<br>1013-88-3 | 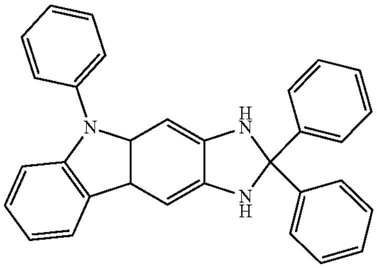 [SMILES: C1=C2NC(c3ccccc3)(c3ccccc3)NC2=CC2C1c1ccccc1N2c1ccccc1] | 49% |

-continued
| Ex. | Reactants | Product | Yield |
| --- | --- | --- | --- |
| S55 | 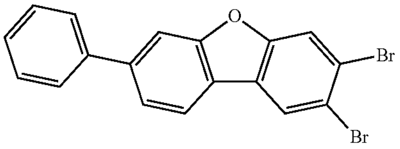 2222443-20-9 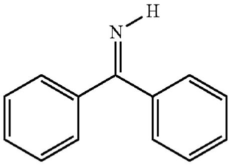 1013-88-3 | 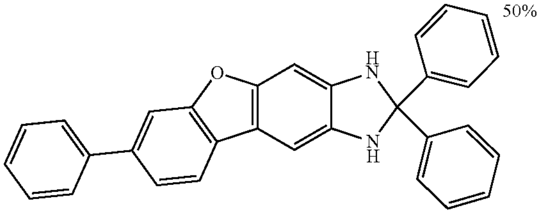 | 50% |
| S56 | 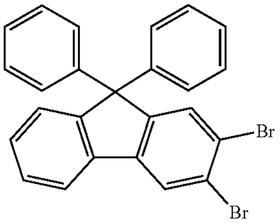 2174966-41-5 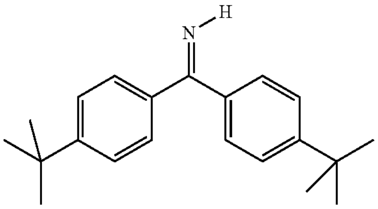 1455305-60-8 | 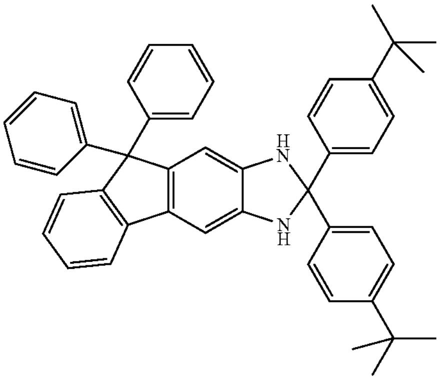 [SMILES: CC(C)(C)c1ccc(C2(c3ccc(C(C)(C)C)cc3)Nc3cc4c(cc3N2)C(c2ccccc2)(c2ccccc2)c2ccccc2-4)cc1] | 55% |
| S57 | 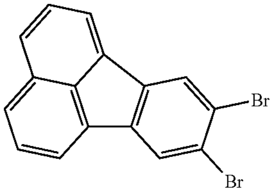 30253-16-8 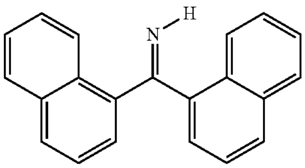 51167-88-5 | 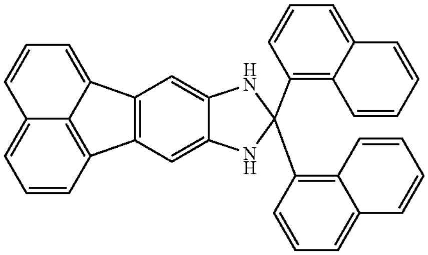 [SMILES: c1ccc2c(C3(c4cccc5ccccc45)Nc4cc5c(cc4N3)-c3cccc4cccc-5c34)cccc2c1] | 44% |

-continued
| Ex. | Reactants | Product | Yield |
| --- | --- | --- | --- |
| S58 | 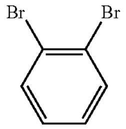<br>583-53-9<br>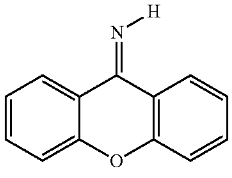<br>5291-42-9 | 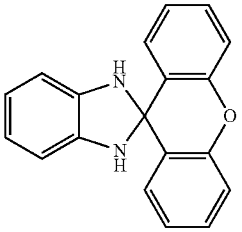 [SMILES: c1ccc2c(c1)NC1(N2)c2ccccc2Oc2ccccc21] | 56% |
| S59 | 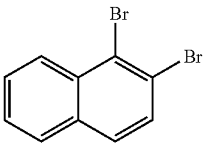<br>5438-13-1<br>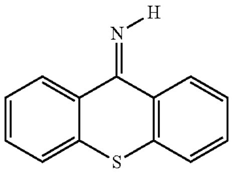<br>5291-43-0 | 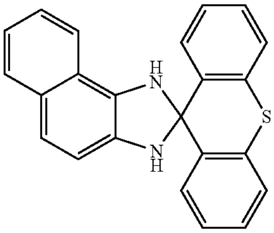 [SMILES: c1ccc2c(c1)Sc1ccccc1C21Nc2ccc3ccccc3c2N1] | 54% |
| S60 | 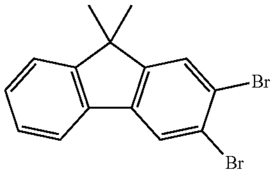<br>2117679-79-3<br>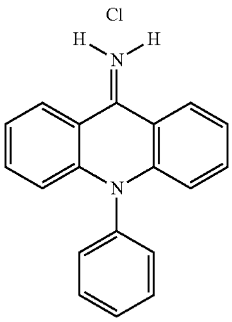<br>108139-69-1 | 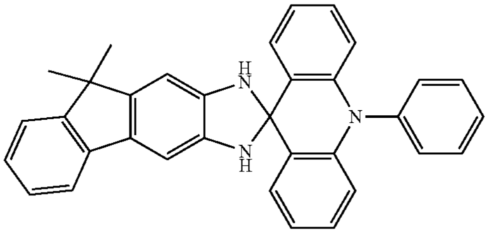 [SMILES: CC1(C)c2ccccc2-c2cc3c(cc21)NC1(N3)c2ccccc2N(c2ccccc2)c2ccccc21] | 31% |

-continued

| Ex. | Reactants | Product | Yield |
|---|---|---|---|
| S61 | 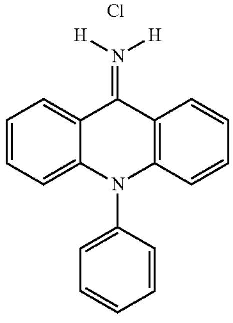 108139-69-1 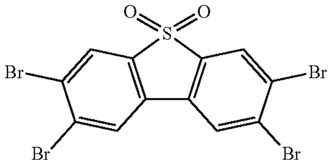 2068014-01-5 | 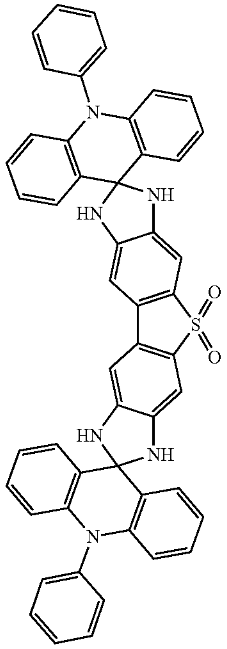 [SMILES: O=S1(=O)c2cc3c(cc2-c2cc4c(cc21)NC1(N4)c2ccccc2N(c2ccccc2)c2ccccc21)NC1(N3)c2ccccc2N(c2ccccc2)c2ccccc21] | 20% |

Example S100

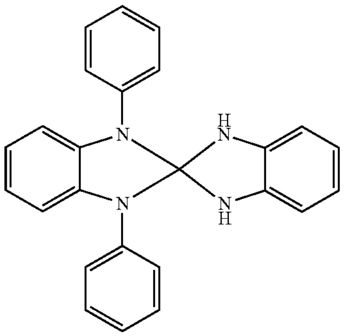 [SMILES: c1ccc(N2c3ccccc3N(c3ccccc3)C23Nc2ccccc2N3)cc1]

A mixture of 26.6 g [100 mmol] of 1,3-dihydro-1,3-diphenyl-2H-benzimidazol-2-one [28386-83-5] and 100 ml of phosphorus oxytrichloride [10025-87-3] is heated under reflux for 16 h. Then the excess phosphorus oxytrichloride is distilled off, the oily residue is taken up in 250 ml of ice-cold methanol, and 200 ml of a saturated aqueous potassium hexafluorophosphate solution is added while stirring. The mixture is stirred for 15 min, 200 ml of ice-water is added dropwise to the suspension with good stirring, and the solids are filtered off with suction, washed three times with 100 ml each time of water, suction-dried and then dried under reduced pressure at 60° C. The 2-chlorobenzimidazolium hexafluorophosphate thus obtained is suspended in 150 ml of acetonitrile, and then 14.1 g [130 mmol] of o-phenylenediamine [95-54-5] and 50 ml of triethylamine are added, and the mixture is stirred at 50° C. for 8 h. The reaction mixture is poured into 500 ml of ice-water with good stirring, and the precipitated solids are filtered off with suction, washed three times with 100 ml of water and twice with 50 ml each time of methanol, and dried under reduced pressure. The crude product is subjected to flash chromatography, n-heptane/EA (ethyl acetate), Torrent automated column system from A. Semrau. Yield: 12.5 g (33 mmol) 33%; purity about 95% by $^{1}H$ NMR.

The following compounds can be prepared analogously:
| Ex. | Reactants | Product | Yield |
|---|---|---|---|
| S101 | 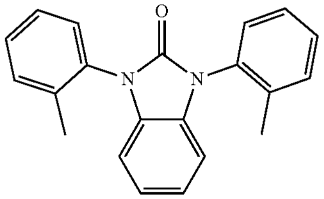 2170819-74-4 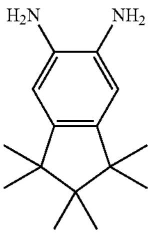 1541101-91-0 | 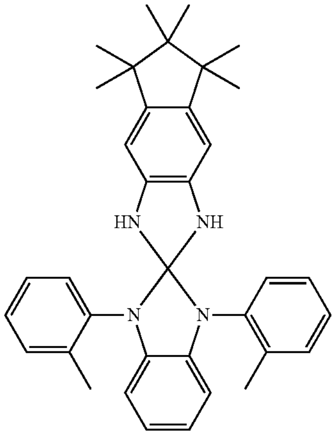 [SMILES: Cc1ccccc1N1c2ccccc2N(c2ccccc2C)C12Nc1cc3c(cc1N2)C(C)(C)C(C)(C)C3(C)C] | 40% |
| S102 | 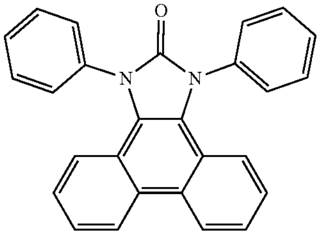 33065-32-6 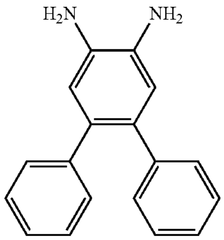 117878-22-5 | 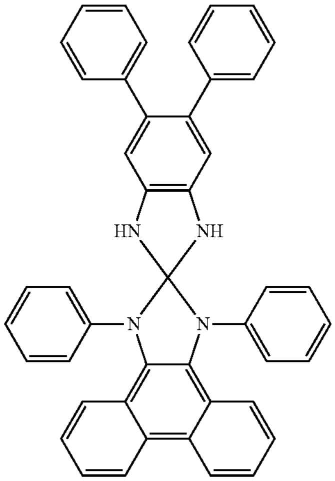 [SMILES: c1ccc(-c2cc3c(cc2-c2ccccc2)NC2(N3)N(c3ccccc3)c3c(c4ccccc4c4ccccc34)N2c2ccccc2)cc1] | 43% |
| S103 | 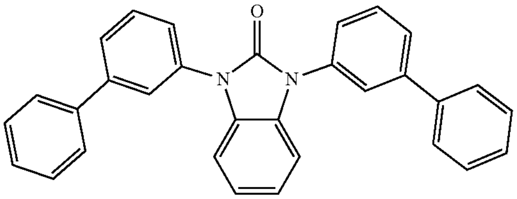 938569-98-8 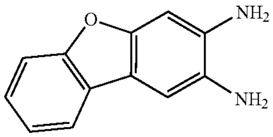 24258-73-9 | 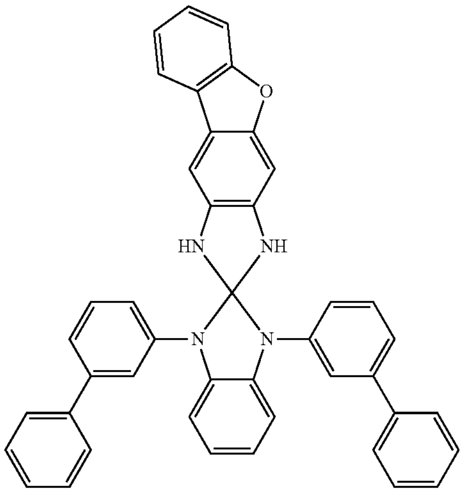 [SMILES: c1ccc(-c2cccc(N3c4ccccc4N(c4cccc(-c5ccccc5)c4)C34Nc3cc5oc6ccccc6c5cc3N4)c2)cc1] | 36% |

-continued
| Ex. | Reactants | Product | Yield |
| --- | --- | --- | --- |
| S104 | 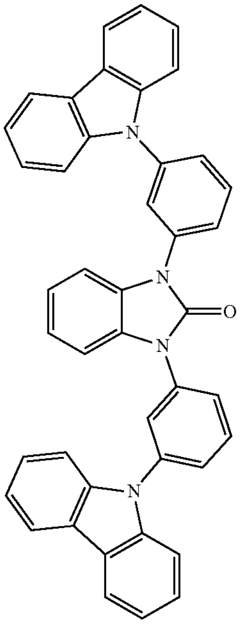 938469-96-6 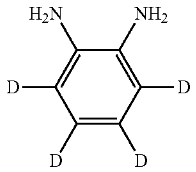 291765-93-0 | 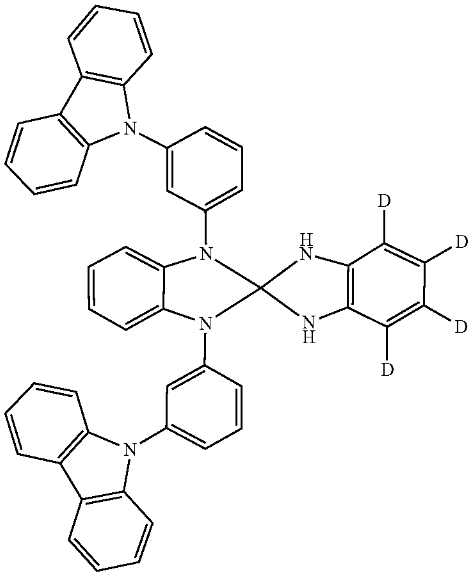 [SMILES: [2H]c1c([2H])c([2H])c2c(c1[2H])NC1(N2)N(c2cccc(-n3c4ccccc4c4ccccc43)c2)c2ccccc2N1c1cccc(-n2c3ccccc3c3ccccc32)c1] | 30% |
| S105 | 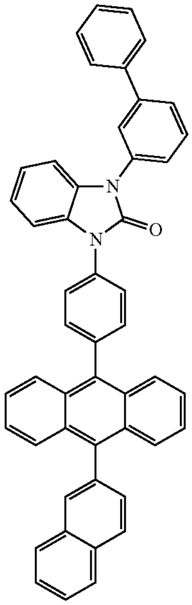 1392427-88-1 | 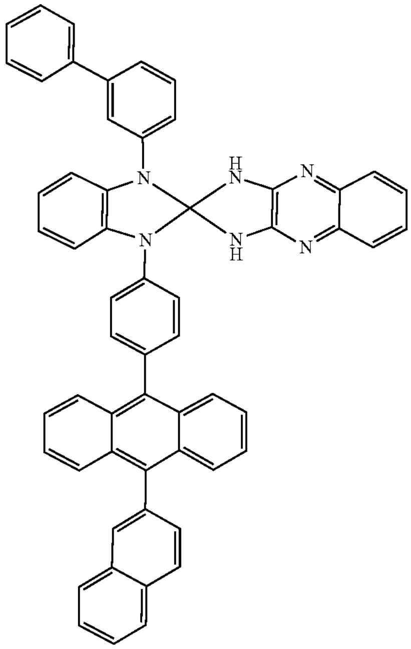 [SMILES: c1ccc(-c2cccc(N3c4ccccc4N(c4ccc(-c5c6ccccc6c(-c6ccc7ccccc7c6)c6ccccc56)cc4)C34Nc3nc5ccccc5nc3N4)c2)cc1] | 35% |

-continued

| Ex. | Reactants | Product | Yield |
|---|---|---|---|
| | 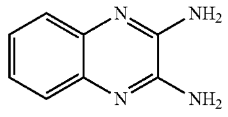<br>6640-47-7 | | |
| S106 | 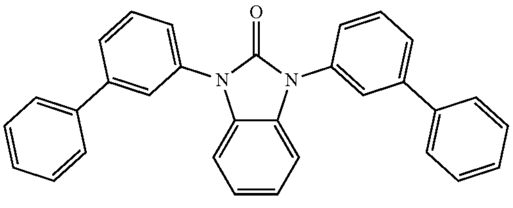<br>938569-98-8<br>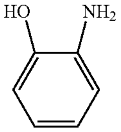<br>95-55-6 | 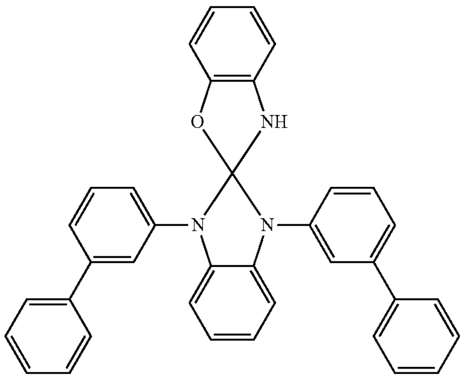 [SMILES: c1ccc(-c2cccc(N3c4ccccc4N(c4cccc(-c5ccccc5)c4)C34Nc3ccccc3O4)c2)cc1] | 45% |
| S107 | 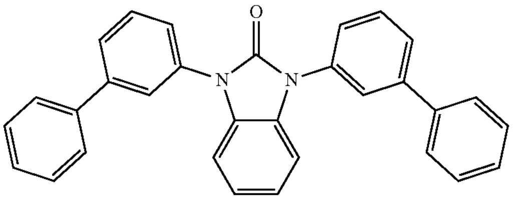<br>938569-98-8<br>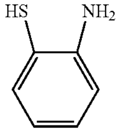<br>137-07-5 | 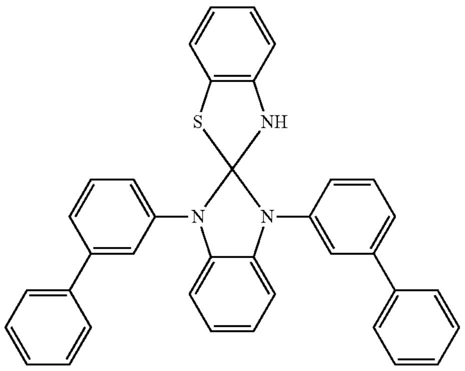 [SMILES: c1ccc(-c2cccc(N3c4ccccc4N(c4cccc(-c5ccccc5)c4)C34Nc3ccccc3S4)c2)cc1] | 38% |
| A108 | 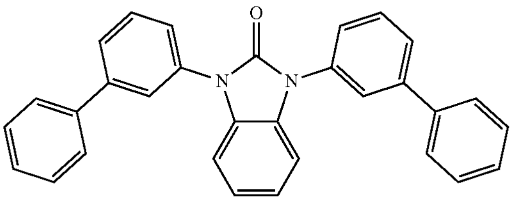<br>938569-98-8<br>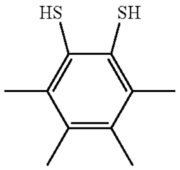<br>137-07-5 | 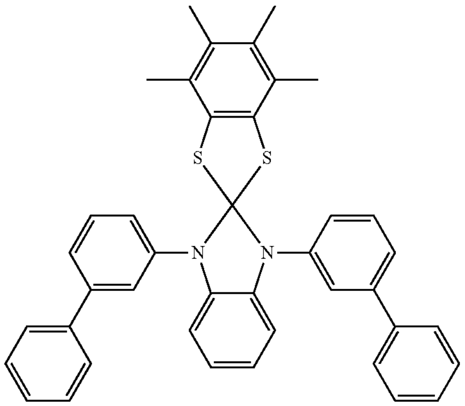 [SMILES: Cc1c(C)c(C)c2c(c1C)SC1(S2)N(c2cccc(-c3ccccc3)c2)c2ccccc2N1c1cccc(-c2ccccc2)c1] | 50% |

By way of clarification, it should be emphasized that the compounds S100 to S107 are encompassed by the scope of protection of the present invention. These compounds are valuable intermediates for production of stable hole conductors, electron conductors and host materials, as set out in detail above. However, compounds having N—H bonds show relatively low stability when used directly in a device. Compound A108 obtained via the above-detailed synthesis route does not have any N—H bond and can thus be used directly for the production of a device.

Synthesis of the Inventive Compounds A

Example A1

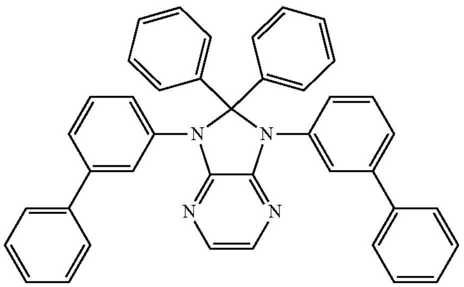 [SMILES: c1ccc(-c2cccc(N3c4nccnc4N(c4cccc(-c5ccccc5)c4)C3(c3ccccc3)c3ccccc3)c2)cc1]

A mixture of 27.4 g [100 mmol] of S1, 53.6 g [230 mmol] of 3-bromobiphenyl [2113-57-7], 25.0 g [260 mmol] of sodium tert-butoxide [865-48-5], 607 mg [3 mmol] of tri-tert-butylphosphine [13716-12-6], 584 mg [2.6 mmol] of palladium(II) acetate and 700 ml of toluene is heated under reflux for 16 h. After cooling, the salts are filtered off with suction using a Celite bed in the form of a toluene slurry. The filtrate is washed three times with 300 ml each time of water and once with 300 ml of saturated sodium chloride solution, and dried over magnesium sulfate. The desiccant is filtered off and concentrated, and the crude product is chromatographed, silica gel, n-heptane/EA, Torrent automated column system from A. Semrau. Further purification is effected by recrystallization or continuous hot extraction crystallization (cellulose thimbles from Whatman, initial amount about 300 ml), typically twice from DCM/iso-propanol (1:2, vv) and then three to five times from DCM/acetonitrile (1:2, vv). Finally, the product is sublimed under high vacuum, preferably by zone sublimation, or freed of the solvent and volatile constituents by heat treatment. Yield: 34.2 g (59 mmol), 59%; purity: about 99.9% by HPLC.

The following compounds can be prepared analogously:

| Ex. | Reactants | Product | Yield |
|---|---|---|---|
| A2 | 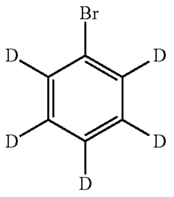 4165-57-5 S2 | 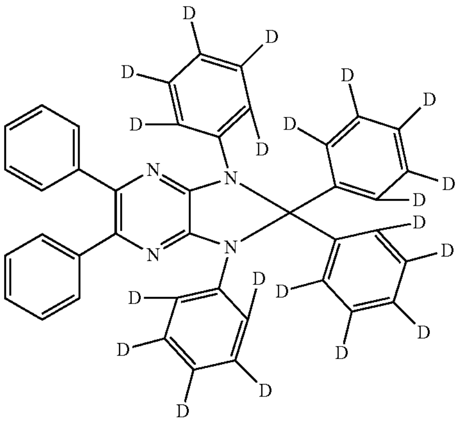 [SMILES: [2H]c1c([2H])c([2H])c(N(c2nc(-c3ccccc3)c(-c3ccccc3)nc2N(c2c([2H])c([2H])c([2H])c([2H])c2[2H])c2c([2H])c([2H])c([2H])c([2H])c2[2H])c2c([2H])c([2H])c([2H])c([2H])c2[2H])c([2H])c1[2H]] | 55% |
| A3 | 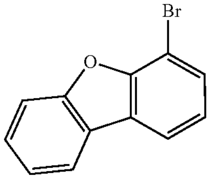 89827-45-2 S3 | 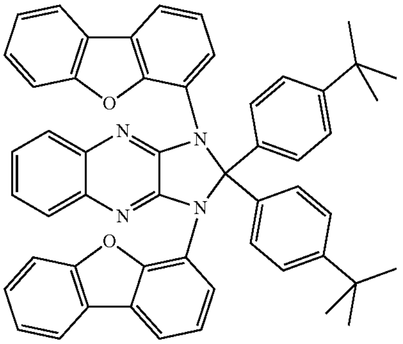 [SMILES: CC(C)(C)c1ccc(C2(c3ccc(C(C)(C)C)cc3)N(c3cccc4c3oc3ccccc34)c3nc4ccccc4nc3N2c2cccc3c2oc2ccccc23)cc1] | 43% |

-continued
| Ex. | Reactants | Product | Yield |
|---|---|---|---|
| A4 | 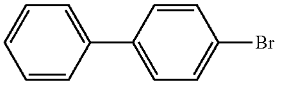<br>92-66-0<br>S4 | 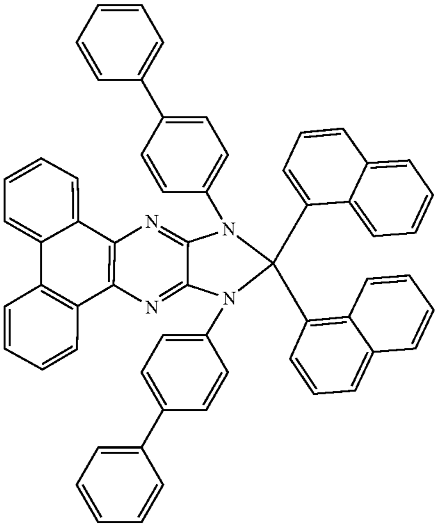 [SMILES: c1ccc(-c2ccc(N3c4nc5c6ccccc6c6ccccc6c5nc4N(c4ccc(-c5ccccc5)cc4)C3(c3cccc4ccccc34)c3cccc4ccccc34)cc2)cc1] | 60% |
| A5 | 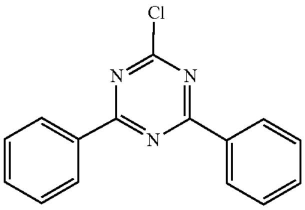<br>3842-55-5<br>S-5 | 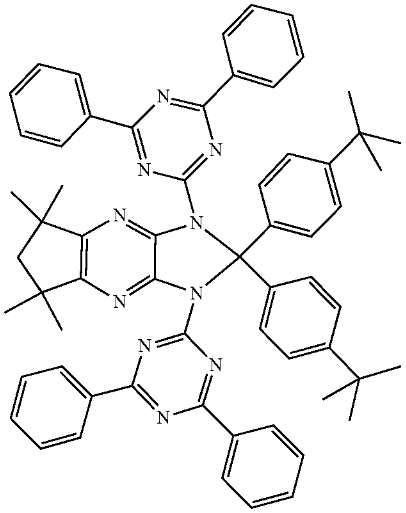 [SMILES: CC(C)(C)c1ccc(C2(c3ccc(C(C)(C)C)cc3)N(c3nc(-c4ccccc4)nc(-c4ccccc4)n3)c3nc4c(nc3N2c2nc(-c3ccccc3)nc(-c3ccccc3)n2)C(C)(C)CC4(C)C)cc1] | 72% |
| A6 | 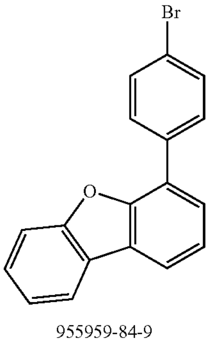<br>955959-84-9<br>S6 | 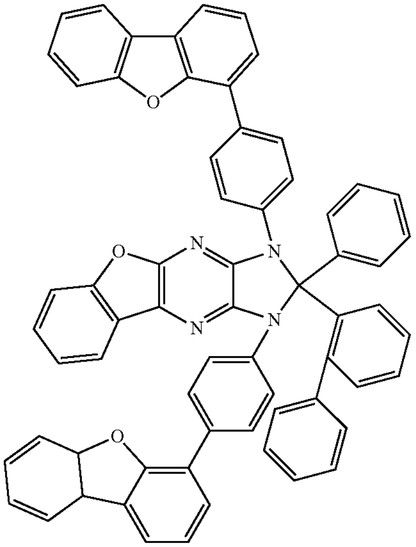 [SMILES: C1=CC2Oc3c(-c4ccc(N5c6nc7c(nc6N(c6ccc(-c8cccc9c8oc8ccccc89)cc6)C5(c5ccccc5)c5ccccc5-c5ccccc5)oc5ccccc57)cc4)cccc3C2C=C1] | 59% |

-continued
| Ex. | Reactants | Product | Yield |
|---|---|---|---|
| A7 | 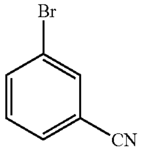 6952-59-6 S7 | 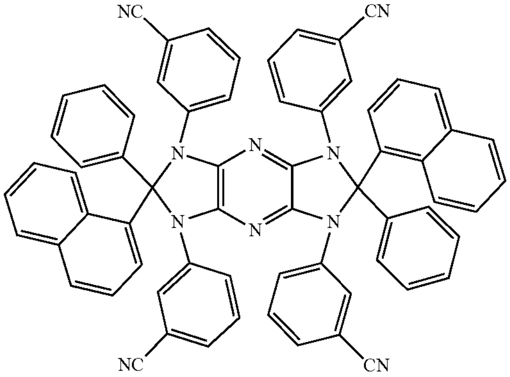 [SMILES: N#Cc1cccc(N2c3nc4c(nc3N(c3cccc(C#N)c3)C2(c2ccccc2)c2cccc3ccccc23)N(c2cccc(C#N)c2)C(c2ccccc2)(c2cccc3ccccc23)N4c2cccc(C#N)c2)c1] | 51% |
| A8 | 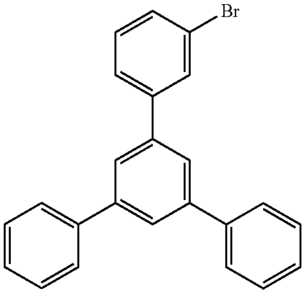 1233200-57-1 S8 | 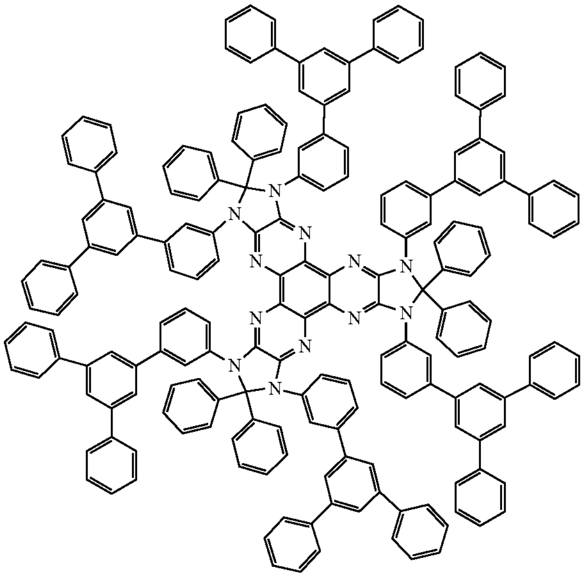 [SMILES: c1ccc(-c2cc(-c3ccccc3)cc(-c3cccc(N4c5nc6c7nc8c(nc7c7nc9c(nc7c6nc5N(c5cccc(-c6cc(-c7ccccc7)cc(-c7ccccc7)c6)c5)C4(c4ccccc4)c4ccccc4)N(c4cccc(-c5cc(-c6ccccc6)cc(-c6ccccc6)c5)c4)C(c4ccccc4)(c4ccccc4)N9c4cccc(-c5cc(-c6ccccc6)cc(-c6ccccc6)c5)c4)N(c4cccc(-c5cc(-c6ccccc6)cc(-c6ccccc6)c5)c4)C(c4ccccc4)(c4ccccc4)N8c4cccc(-c5cc(-c6ccccc6)cc(-c6ccccc6)c5)c4)c3)c2)cc1] | 17% |
| A50a | 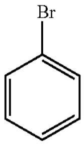 108-86-1 S50 | 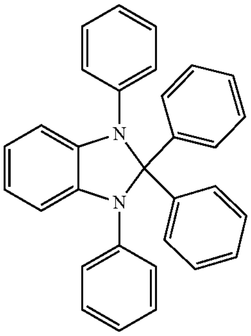 [SMILES: c1ccc(N2c3ccccc3N(c3ccccc3)C2(c2ccccc2)c2ccccc2)cc1] | 63% |

-continued
| Ex. | Reactants | Product | Yield |
| --- | --- | --- | --- |
| A50b | 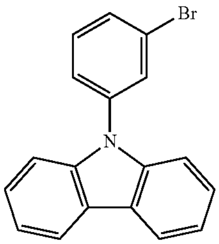 185112-61-2 S50 | 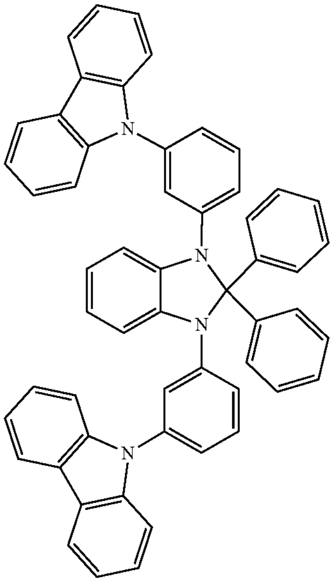 [SMILES: c1ccc(C2(c3ccccc3)N(c3cccc(-n4c5ccccc5c5ccccc54)c3)c3ccccc3N2c2cccc(-n3c4ccccc4c4ccccc43)c2)cc1] | 61% |
| A51 | 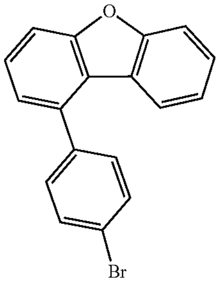 1786416-89-4 S51 | 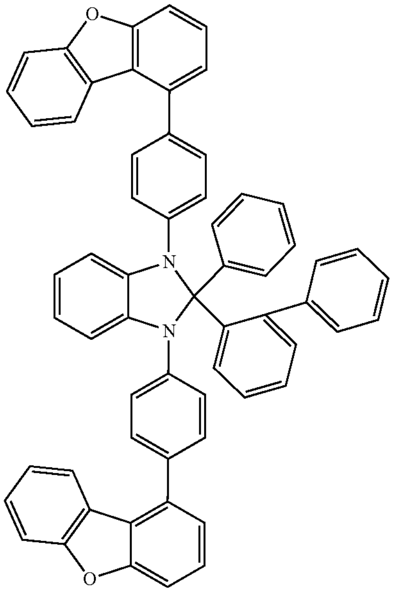 [SMILES: c1ccc(-c2ccccc2C2(c3ccccc3)N(c3ccc(-c4cccc5oc6ccccc6c45)cc3)c3ccccc3N2c2ccc(-c3cccc4oc5ccccc5c34)cc2)cc1] | 57% |

-continued
| Ex. | Reactants | Product | Yield |
|---|---|---|---|
| A52 | 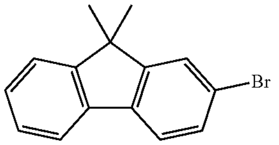 26608-06-0 S53 | 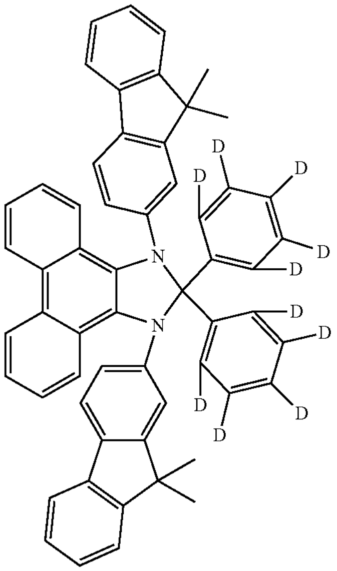 [SMILES: [2H]c1c([2H])c([2H])c(C2(c3c([2H])c([2H])c([2H])c([2H])c3[2H])N(c3ccc4c(c3)C(C)(C)c3ccccc3-4)c3c(c4ccccc4c4ccccc34)N2c2ccc3c(c2)C(C)(C)c2ccccc2-3)c([2H])c1[2H]] | 55% |
| A53 | 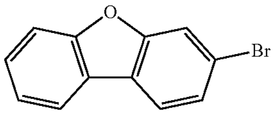 26608-06-0 S53 | 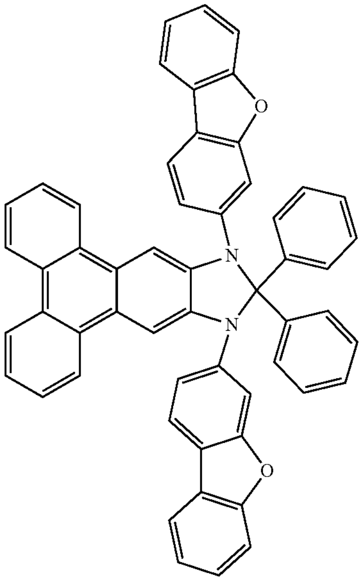 [SMILES: c1ccc(C2(c3ccccc3)N(c3ccc4c(c3)oc3ccccc34)c3cc4c5ccccc5c5ccccc5c4cc3N2c2ccc3c(c2)oc2ccccc23)cc1] | 60% |

-continued
| Ex. | Reactants | Product | Yield |
|---|---|---|---|
| A54 | 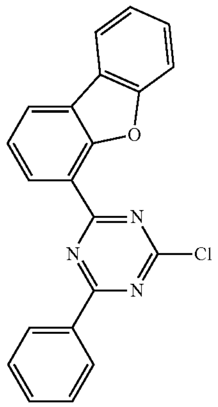 1472729-25-1 S54 | 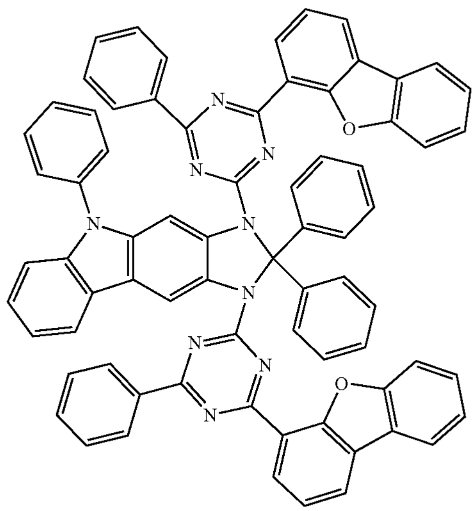 [SMILES: c1ccc(-c2nc(-c3cccc4c3oc3ccccc34)nc(N3c4cc5c6ccccc6n(-c6ccccc6)c5cc4N(c4nc(-c5ccccc5)nc(-c5cccc6c5oc5ccccc56)n4)C3(c3ccccc3)c3ccccc3)n2)cc1] | 62% |
| A55 | 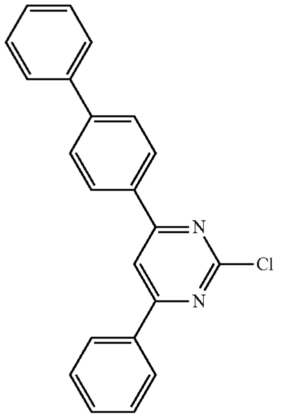 1624293-49-7 S55 | 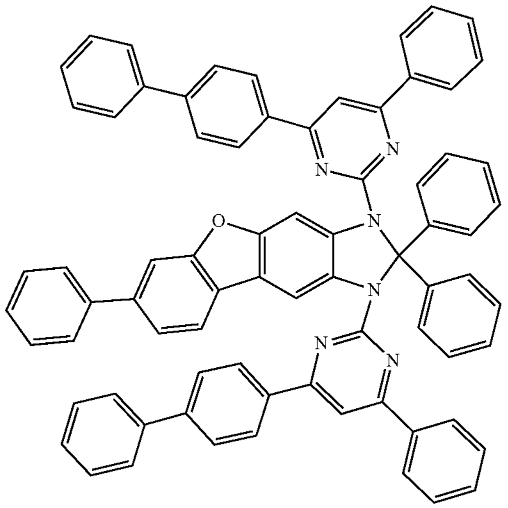 [SMILES: c1ccc(-c2ccc(-c3cc(-c4ccccc4)nc(N4c5cc6oc7cc(-c8ccccc8)ccc7c6cc5N(c5nc(-c6ccccc6)cc(-c6ccc(-c7ccccc7)cc6)n5)C4(c4ccccc4)c4ccccc4)n3)cc2)cc1] | 67% |

-continued
| Ex. | Reactants | Product | Yield |
| --- | --- | --- | --- |
| A56 | 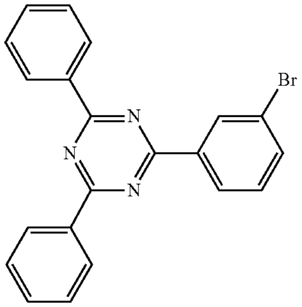 864377-31-1 S56 | 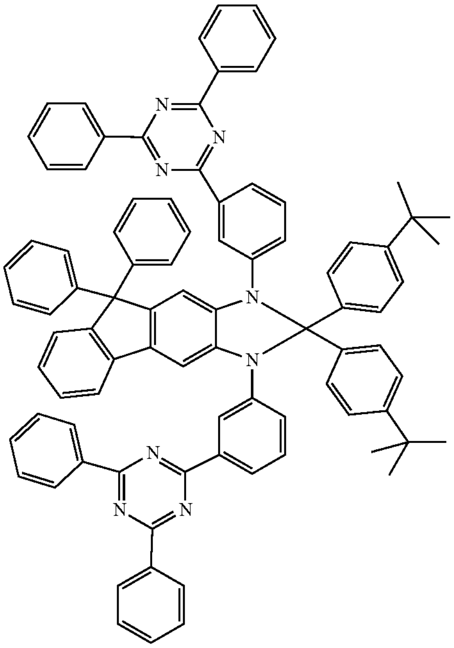 [SMILES: CC(C)(C)c1ccc(N(c2cccc(-c3nc(-c4ccccc4)nc(-c4ccccc4)n3)c2)c2cc3c(cc2N(c2ccc(C(C)(C)C)cc2)c2cccc(-c4nc(-c5ccccc5)nc(-c5ccccc5)n4)c2)C(c2ccccc2)(c2ccccc2)c2ccccc2-3)cc1] | 56% |
| A57 | 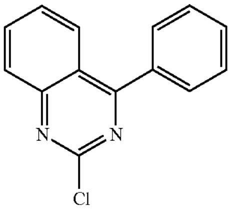 29874-83-7 S57 | 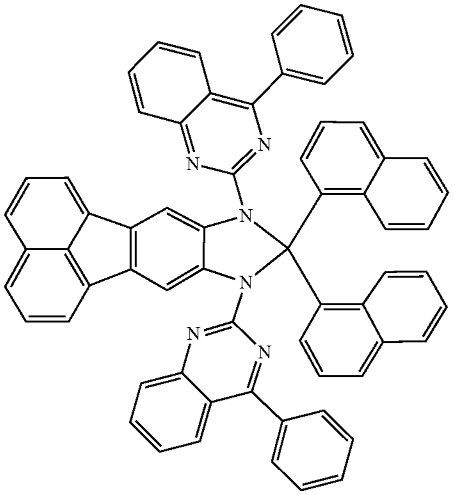 [SMILES: c1ccc(-c2nc(N3c4cc5c(cc4N(c4nc(-c6ccccc6)c6ccccc6n4)C3(c3cccc4ccccc34)c3cccc4ccccc34)-c3cccc4cccc-5c34)nc3ccccc23)cc1] | 64% |
| A58 | 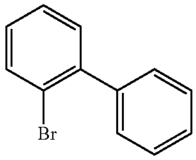 2052-07-5 S58 | 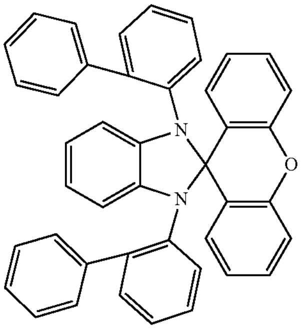 [SMILES: c1ccc(-c2ccccc2N2c3ccccc3N(c3ccccc3-c3ccccc3)C23c2ccccc2Oc2ccccc23)cc1] | 45% |

-continued
| Ex. | Reactants | Product | Yield |
|---|---|---|---|
| A59 | 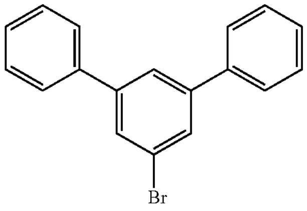 103068-20-8 S59 | 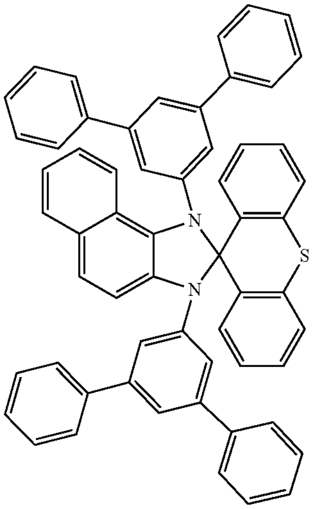 [SMILES: c1ccc(-c2cc(-c3ccccc3)cc(N3c4ccc5ccccc5c4N(c4cc(-c5ccccc5)cc(-c5ccccc5)c4)C34c3ccccc3Sc3ccccc34)c2)cc1] | 61% |
| A60 | 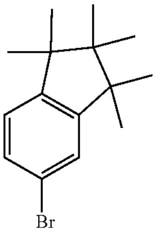 1562418-80-7 S60 | 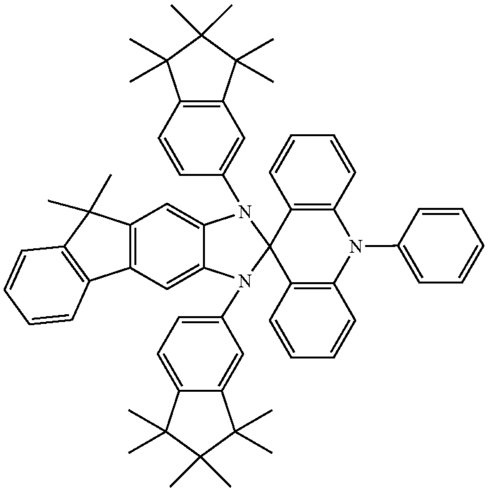 [SMILES: CC1(C)c2ccccc2-c2cc3c(cc21)N(c1ccc2c(c1)C(C)(C)C(C)(C)C2(C)C)C1(c2ccccc2N(c2ccccc2)c2ccccc21)N3c1ccc2c(c1)C(C)(C)C(C)(C)C2(C)C] | 59% |

-continued
| Ex. | Reactants | Product | Yield |
|---|---|---|---|
| A61 | 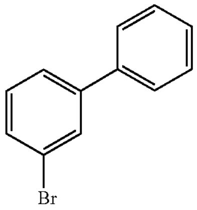<br>2113-57-7<br>S61 | 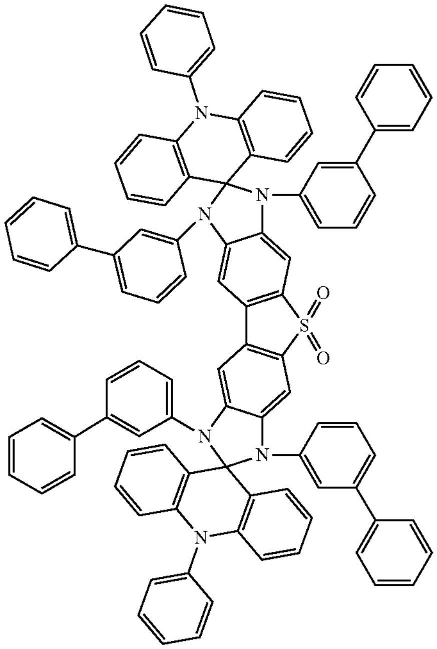 [SMILES: O=S1(=O)c2cc3c(cc2-c2cc4c(cc21)N(c1cccc(-c2ccccc2)c1)C1(c2ccccc2N(c2ccccc2)c2ccccc21)N4c1cccc(-c2ccccc2)c1)N(c1cccc(-c2ccccc2)c1)C1(c2ccccc2N(c2ccccc2)c2ccccc21)N3c1cccc(-c2ccccc2)c1] | 26% |
| A100 | 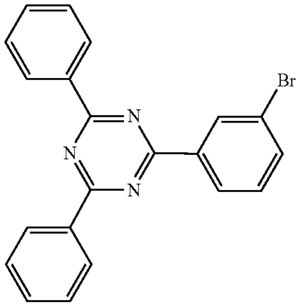<br>864377-31-1<br>S100 | 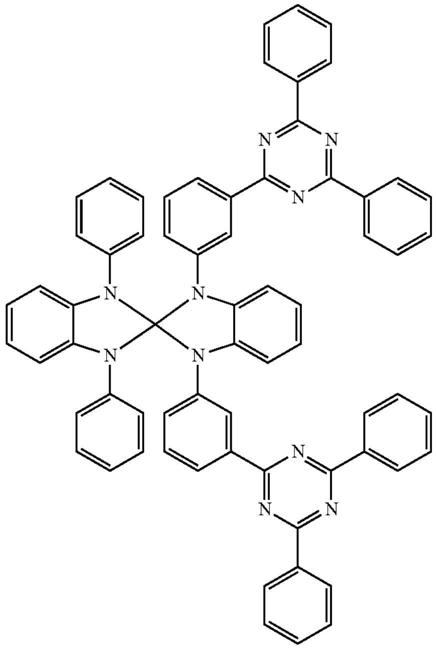 [SMILES: c1ccc(-c2nc(-c3ccccc3)nc(-c3cccc(N4c5ccccc5N(c5cccc(-c6nc(-c7ccccc7)nc(-c7ccccc7)n6)c5)C45N(c4ccccc4)c4ccccc4N5c4ccccc4)c3)n2)cc1] | 63% |

-continued
| Ex. | Reactants | Product | Yield |
|---|---|---|---|
| A101 | 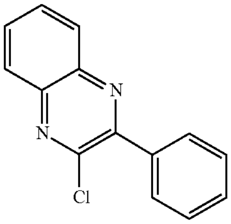<br>108-86-1<br>S102 | 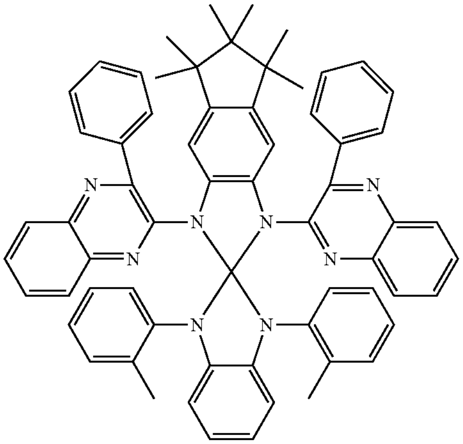 [SMILES: Cc1ccccc1N1c2ccccc2N(c2ccccc2C)C12N(c1nc3ccccc3nc1-c1ccccc1)c1cc3c(cc1N2c1nc2ccccc2nc1-c1ccccc1)C(C)(C)C(C)(C)C3(C)C] | 66% |
| A102 | 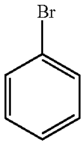<br>108-86-1<br>S102 | 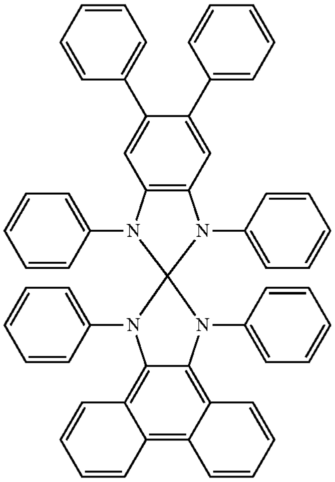 [SMILES: c1ccc(-c2cc3c(cc2-c2ccccc2)N(c2ccccc2)C2(N3c3ccccc3)N(c3ccccc3)c3c(c4ccccc4c4ccccc34)N2c2ccccc2)cc1] | 60% |
| A103 | 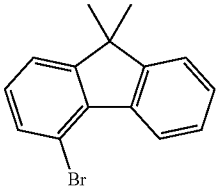<br>942615-32-9<br>S103 | 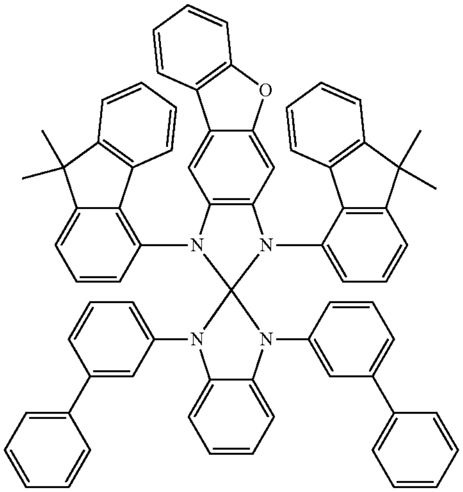 [SMILES: CC1(C)c2ccccc2-c2c(N3c4cc5oc6ccccc6c5cc4N(c4cccc5c4-c4ccccc4C5(C)C)C34N(c3cccc(-c5ccccc5)c3)c3ccccc3N4c3cccc(-c4ccccc4)c3)cccc21] | 48% |

-continued
| Ex. | Reactants | Product | Yield |
| --- | --- | --- | --- |
| A104 | 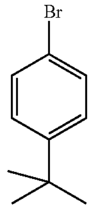 3972-65-4 S104 | 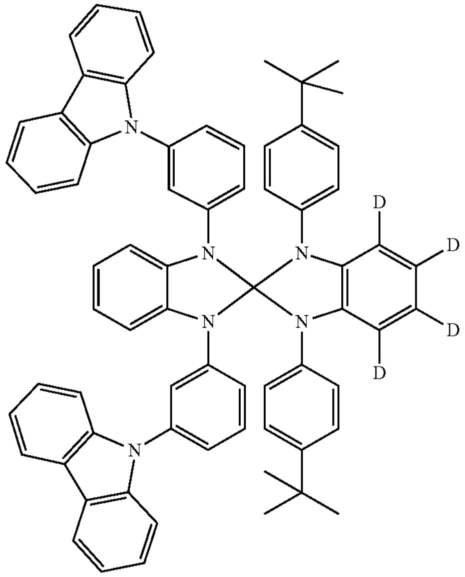 [SMILES: [2H]c1c([2H])c([2H])c2c(c1[2H])N(c1ccc(C(C)(C)C)cc1)C1(N(c3cccc(-n4c5ccccc5c5ccccc54)c3)c3ccccc3N1c1cccc(-n3c4ccccc4c4ccccc43)c1)N2c1ccc(C(C)(C)C)cc1] | 57% |
| A105 | 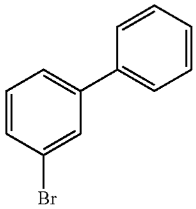 2113-57-7 S105 | 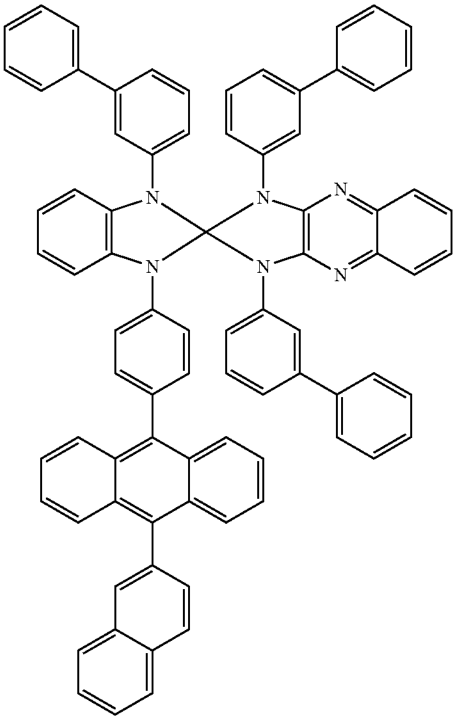 [SMILES: c1ccc(-c2cccc(N3c4ccccc4N(c4ccc(-c5c6ccccc6c(-c6ccc7ccccc7c6)c6ccccc56)cc4)C34N(c3cccc(-c5ccccc5)c3)c3nc5ccccc5nc3N4c3cccc(-c4ccccc4)c3)c2)cc1] | 59% |

-continued
| Ex. | Reactants | Product | Yield |
|---|---|---|---|
| A106a | 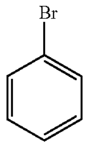 108-86-1 S106 | 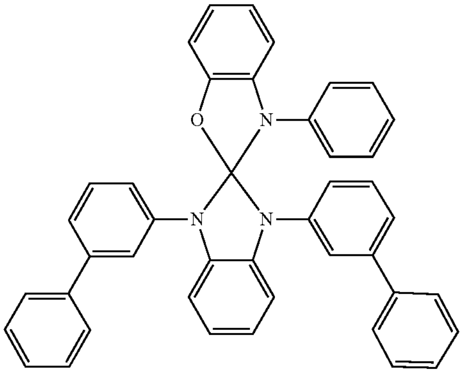 [SMILES: c1ccc(-c2cccc(N3c4ccccc4N(c4cccc(-c5ccccc5)c4)C34Oc3ccccc3N4c3ccccc3)c2)cc1] | |
| A106b | 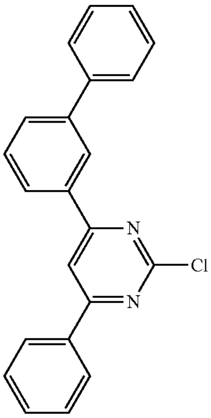 1624289-88-8 S106 | 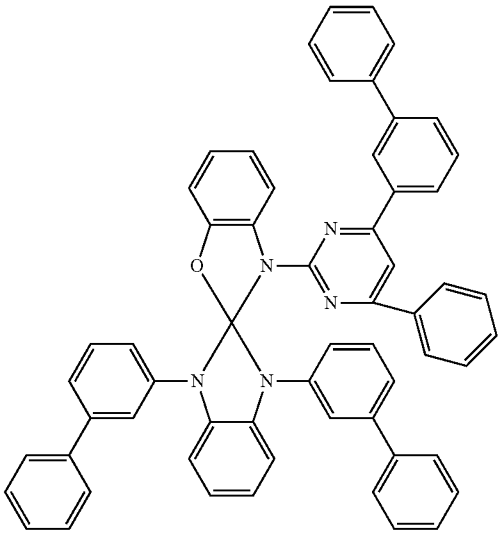 [SMILES: c1ccc(-c2cccc(-c3cc(-c4ccccc4)nc(N4c5ccccc5OC45N(c4cccc(-c6ccccc6)c4)c4ccccc4N5c4cccc(-c5ccccc5)c4)n3)c2)cc1] | 72% |
| A107 | 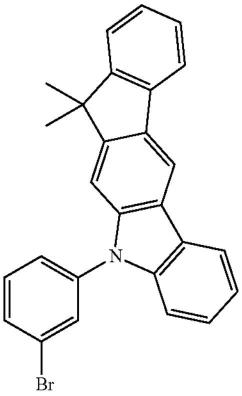 1369587-63-2 S107 | 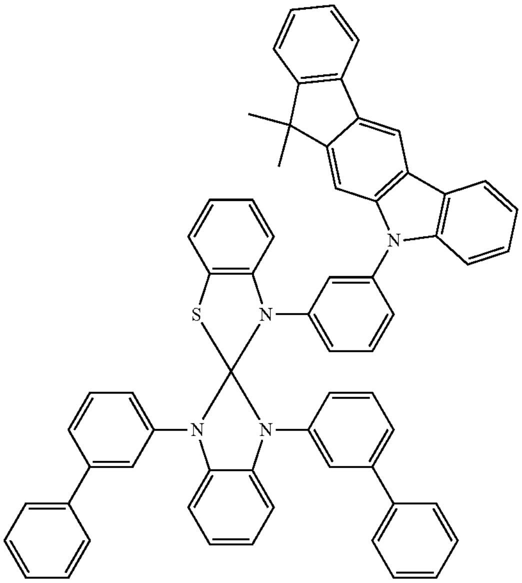 [SMILES: CC1(C)c2ccccc2-c2cc3c4ccccc4n(-c4cccc(N5c6ccccc6SC56N(c5cccc(-c7ccccc7)c5)c5ccccc5N6c5cccc(-c6ccccc6)c5)c4)c3cc21] | 67% |

Example: Production of the OLEDs

A) Vacuum-Processed Devices:

OLEDs of the invention and OLEDs according to the prior art are produced by a general method according to WO 2004/058911, which is adapted to the circumstances described here (variation in layer thickness, materials used).

In the examples which follow, the results for various OLEDs are presented. Cleaned glass plates (cleaning in Miele laboratory glass washer, Merck Extran detergent) coated with structured ITO (indium tin oxide) of thickness 50 nm are pretreated with UV ozone for 25 minutes (PR-100 UV ozone generator from UVP) and, within 30 min, for improved processing, coated with 20 nm of PEDOT:PSS (poly(3,4-ethylenedioxythiophene) poly(styrenesulfonate), purchased as CLEVIOS™ P VP AI 4083 from Heraeus Precious Metals GmbH Deutschland, spun on from aqueous solution) and then baked at 180° C. for 10 min. These coated glass plates form the substrates to which the OLEDs are applied.

The OLEDs basically have the following layer structure: substrate/hole injection layer 1 (HIL1) consisting of HTM1 doped with 5% NDP-9 (commercially available from Novaled), 20 nm/hole transport layer 1 (HTL1) consisting of HTM1, 170 nm for blue devices, 215 nm for green/yellow devices, 110 nm for red devices/hole transport layer 2 (HTL2)/emission layer (EML)/hole blocker layer (HBL)/electron transport layer (ETL)/optional electron injection layer (EIL from ETM2) and finally a cathode. The cathode is formed by an aluminum layer of thickness 100 nm.

First of all, vacuum-processed OLEDs are described. For this purpose, all the materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as M1:M2:Ir(L1) (55%:35%:10%) mean here that the material M1 is present in the layer in a proportion by volume of 55%, M2 in a proportion by volume of 35% and Ir(L1) in a proportion by volume of 10%. Analogously, the electron transport layer may also consist of a mixture of two materials. The exact structure of the OLEDs can be found in table 1. The materials used for production of the OLEDs are shown in table 4.

The OLEDs are characterized in a standard manner. For this purpose, the electroluminescence spectra, the current efficiency (measured in cd/A), the power efficiency (measured in lm/W) and the external quantum efficiency (EQE, measured in percent) as a function of luminance, calculated from current-voltage-luminance characteristics (IUL characteristics) assuming Lambertian emission characteristics, and also the lifetime are determined. Electroluminescence spectra are determined at a luminance of 1000 cd/m$^2$, and these are used to calculate the CIE 1931 x and y color coordinates.

Use of Compounds of the Invention as Emitter Materials in Phosphorescent OLEDs

Among other uses, the compounds of the invention can be used as hole transport material in the HTL, as hole-conducting host material hTMM or electron-conducting host material eTMM in the emission layer EML of a phosphorescent OLED, and as electron transport material in the ETL. The results for the OLEDs are collated in table 2.

TABLE 1

Structure of the OLEDs

| Ex. | HTL2 thickness | EML thickness | HBL thickness | ETL thickness |
|---|---|---|---|---|
| **Blue OLEDs** | | | | |
| DB1-Ref | HTM3 20 nm | M3:M4:IrB1 (30%:60%:10%) 30 nm | ETM1 10 nm | ETM1:ETM2 (50%:50%) 30 nm |
| DB1 | A50a 20 nm | M3:M4:IrB1 (30%:60%:10%) 30 nm | ETM1 10 nm | ETM1:ETM2 (50%:50%) 30 nm |
| DB2 | A58 20 nm | M3:M4:IrB1 (30%:60%:10%) 30 nm | ETM1 10 nm | ETM1:ETM2 (50%:50%) 30 nm |
| **Green and yellow OLEDs** | | | | |
| DG1-Ref | P1-1 10 nm | M1:M2:IrG1 (40%:50%:10%) 30 nm | ETM1 10 nm | ETM1:ETM2 (50%:50%) 30 nm |
| DG1 | A50a 10 nm | M1:M2:IrG1 (40%:50%:10%) 30 nm | ETM1 10 nm | ETM1:ETM2 (50%:50%) 30 nm |
| DG2-Ref | HTM2 10 nm | M1:P1-1:IrG1 (60%:25%:15%) 30 nm | ETM1 10 nm | ETM1:ETM2 (50%:50%) 30 nm |
| DG3-Ref | HTM2 10 nm | M1:P1-29:IrG1 (60%:25%:15%) 30 nm | ETM1 10 nm | ETM1:ETM2 (50%:50%) 30 nm |
| DG2 | HTM2 10 nm | M1:A50a:IrG1 (60%:25%:15%) 30 nm | ETM1 10 nm | ETM1:ETM2 (50%:50%) 30 nm |
| DG3 | HTM2 10 nm | M1:A50b:IrG1 (60%:25%:15%) 30 nm | ETM1 10 nm | ETM1:ETM2 (50%:50%) 30 nm |
| DG4 | HTM2 10 nm | M1:A51:IrG1 (60%:25%:15%) 30 nm | ETM1 10 nm | ETM1:ETM2 (50%:50%) 30 nm |
| DG5 | HTM2 10 nm | M1:A52:IrG1 (60%:25%:15%) 30 nm | ETM1 10 nm | ETM1:ETM2 (50%:50%) 30 nm |
| DG6 | HTM2 10 nm | M1:A53:IrG2 (50%:40%:10%) 30 nm | ETM1 10 nm | ETM1:ETM2 (50%:50%) 30 nm |
| DG7 | A58 10 nm | M1:A58:IrG2 (50%:40%:10%) 30 nm | ETM1 10 nm | ETM1:ETM2 (50%:50%) 30 nm |
| DG8 | A60 10 nm | M1:A60:IrG2 (50%:40%:10%) 30 nm | ETM1 10 nm | ETM1:ETM2 (50%:50%) 30 nm |
| DG9 | A58 10 nm | M1:A108:IrG2 (55%:30%:15%) 30 nm | ETM1 10 nm | ETM1:ETM2 (50%:50%) 30 nm |
| DG10 | A102 10 nm | M1:M2:IrG3 (40%:45%:15%) 30 nm | ETM1 10 nm | ETM1:ETM2 (50%:50%) 30 nm |
| DG11 | HTM2 10 nm | M1:A1:IrG3 (44%:44%:12%) 30 nm | ETM1 10 nm | ETM1:ETM2 (50%:50%) 30 nm |
| DG12 | HTM2 10 nm | M1:A2:IrG3 (44%:44%:12%) 30 nm | ETM1 10 nm | ETM1:ETM2 (50%:50%) 30 nm |
| DG13 | HTM2 10 nm | M1:A3:IrG3 (44%:44%:12%) 30 nm | ETM1 10 nm | ETM1:ETM2 (50%:50%) 30 nm |
| DG14 | HTM2 10 nm | M1:M2:IrG3 (44%:44%:12%) 30 nm | A5 10 nm | ETM1:ETM2 (50%:50%) 30 nm |
| DG15 | HTM2 10 nm | A55:M2:IrG3 (50%:40%:10%) 30 nm | ETM1 10 nm | ETM1:ETM2 (50%:50%) 30 nm |
| **Red OLEDs** | | | | |
| DR1-Ref | HTM2 10 nm | M5:IrR1 (94%:6%) 30 nm | ETM1 10 nm | ETM1:ETM2 (50%:50%) 30 nm |
| DR1 | HTM2 10 nm | A57:IrR1 (94%:6%) 30 nm | ETM1 10 nm | ETM1:ETM2 (50%:50%) 30 nm |

TABLE 1-continued

| Structure of the OLEDs | | | | |
|---|---|---|---|---|
| Ex. | HTL2 thickness | EML thickness | HBL thickness | ETL thickness |
| DR2 | HTM2<br>10 nm | A101:IrR1<br>(94%:6%)<br>30 nm | ETM1<br>10 nm | ETM1:ETM2<br>(50%:50%)<br>30 nm |

TABLE 2

| Results for the vacuum-processed OLEDs | | | |
|---|---|---|---|
| Ex. | EQE (%) 1000 $cd/m^2$ | Voltage (V) 1000 $cd/m^2$ | CIE x/y 1000 $cd/m^2$ |
| Blue OLEDs | | | |
| DB1-Ref | 21.3 | 3.8 | 0.16/0.36 |
| DB1 | 22.2 | 3.6 | 0.16/0.35 |
| DB2 | 22.6 | 3.5 | 0.16/0.35 |
| Green and yellow OLEDs | | | |
| DG1-Ref | 20.6 | 3.4 | 0.34/0.61 |
| DG1 | 22.1 | 3.1 | 0.34/0.61 |
| DG2-Ref | 20.3 | 3.5 | 0.35/0.61 |
| DG3-Ref | 20.1 | 3.4 | 0.35/0.61 |
| DG2 | 21.9 | 3.3 | 0.35/0.61 |
| DG3 | 22.3 | 3.1 | 0.35/0.61 |
| DG4 | 22.1 | 3.2 | 0.35/0.61 |
| DG5 | 22.0 | 3.3 | 0.35/0.61 |
| DG6 | 22.2 | 3.2 | 0.34/0.64 |
| DG7 | 22.4 | 3.0 | 0.33/0.63 |
| DG8 | 22.1 | 3.1 | 0.33/0.63 |
| DG9 | 21.8 | 3.1 | 0.34/0.63 |
| DG10 | 28.1 | 3.1 | 0.49/0.51 |
| DG11 | 27.7 | 3.1 | 0.49/0.51 |
| DG12 | 27.5 | 3.1 | 0.49/0.51 |
| DG13 | 28.0 | 3.0 | 0.49/0.51 |
| DG14 | 27.3 | 3.1 | 0.48/0.51 |
| DG15 | 27.5 | 3.0 | 0.48/0.51 |
| Red OLEDs | | | |
| DR1-Ref | 18.8 | 3.3 | 0.70/0.30 |
| DR1 | 18.6 | 3.1 | 0.70/0.30 |
| DR2 | 19.4 | 3.1 | 0.70/0.30 |

B) Solution-Processed Devices:

From Soluble Functional Materials of Low Molecular Weight

The compounds of the invention may also be processed from solution and lead therein to OLEDs which are much simpler in terms of process technology compared to the vacuum-processed OLEDs, but nevertheless have good properties. The production of such components is based on the production of polymeric light-emitting diodes (PLEDs), which has already been described many times in the literature (for example in WO 2004/037887). The structure is composed of substrate/ITO/hole injection layer (60 nm)/interlayer (20 nm)/emission layer (60 nm)/hole blocker layer (10 nm)/electron transport layer (40 nm)/cathode. For this purpose, substrates from Technoprint (soda-lime glass) are used, to which the ITO structure (indium tin oxide, a transparent conductive anode) is applied. The substrates are cleaned in a cleanroom with DI water and a detergent (Deconex 15 PF) and then activated by a UV/ozone plasma treatment. Thereafter, likewise in a cleanroom, a 20 nm hole injection layer (PEDOT:PSS from Clevios™) is applied by spin-coating. The required spin rate depends on the degree of dilution and the specific spin-coater geometry. In order to remove residual water from the layer, the substrates are baked on a hotplate at 200° C. for 30 minutes. The interlayer used serves for hole transport, with use of HL-X from Merck in this case. The interlayer may alternatively also be replaced by one or more layers which merely have to fulfill the condition of not being leached off again by the subsequent processing step of EML deposition from solution. For production of the emission layer, the triplet emitters of the invention are dissolved together with the matrix materials in toluene or chlorobenzene. The typical solids content of such solutions is between 16 and 25 g/l when, as here, the layer thickness of 60 nm which is typical of a device is to be achieved by means of spin-coating. The solution-processed devices contain an emission layer Ma:Mb:Ir (w %:x %:z %) or Ma:Mb:Mc:Ir (w %:x %:y %:z %); see table 3. The emission layer is spun on in an inert gas atmosphere, argon in the present case, and baked at 160° C. for 10 min. Vapor-deposited above the latter are the hole blocker layer (10 nm ETM1) and the electron transport layer (40 nm ETM1 (50%)/ETM2 (50%)) (vapor deposition systems from Lesker or the like, typical vapor deposition pressure $5\times10^{-6}$ mbar). Finally, a cathode of aluminum (100 nm) (high-purity metal from Aldrich) is applied by vapor deposition. In order to protect the device from air and air humidity, the device is finally encapsulated and then characterized. The OLED examples cited have not yet been optimized. Table 3 summarizes the data obtained.

TABLE 3

| Results with materials processed from solution | | | | |
|---|---|---|---|---|
| Ex. | Emission layer | EQE (%) 1000 $cd/m^2$ | Voltage (V) 1000 $cd/m^2$ | CIE x/y 1000 $cd/m^2$ |
| Sol-Ref | M6:M7:IrG-Sol1 (20%:55%:25%) | 22.7 | 4.5 | 0.34/0.62 |
| Sol-D1 | M6:M7:A6:IrG-Sol1 (20%:40%:15%:25%) | 22.8 | 4.3 | 0.34/0.62 |
| Sol-D2 | M6:M7:A7:IrG-Sol1 (20%:45%:10%:25%) | 22.7 | 4.3 | 0.34/0.62 |
| Sol-D3 | M6:M7:A8:IrG-Sol1 (20%:50%:5%:25%) | 22.9 | 4.2 | 0.34/0.62 |
| Sol-D4 | M6:M7:A61:IrG-Sol1 (20%:50%:5%:25%) | 22.9 | 4.3 | 0.34/0.62 |
| Sol-D5 | M6:M7:A103:IrG-Sol1 (25%:50%:5%:20%) | 22.7 | 4.2 | 0.35/0.61 |
| S0l-D6 | M6:M7:A104:IrG-Sol1 (25%:50%:5%:20%) | 23.0 | 4.2 | 0.35/0.62 |
| Sol-D7 | M6:M7:A107:IrG-Sol1 (25%:50%:5%:20%) | 23.1 | 4.2 | 0.35/0.62 |
| Sol-D8 | A54:M7:IrG-Sol1 (15%:60%:25%) | 22.9 | 4.2 | 0.34/0.62 |
| Sol-D9 | A56:M7:IrG-Sol1 (15%:60%:25%) | 23.1 | 4.3 | 0.34/0.62 |
| Sol-D10 | A106b:M7:IrG-Sol1 (40%:35%:25%) | 22.9 | 4.3 | 0.34/0.62 |

TABLE 4
| Structural formulae of the materials used |
|---|
| 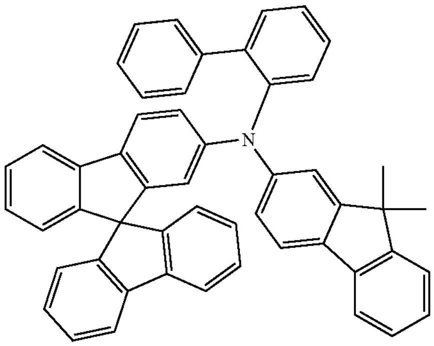 |
| HTM1 |
| [136463-07-5] |
| 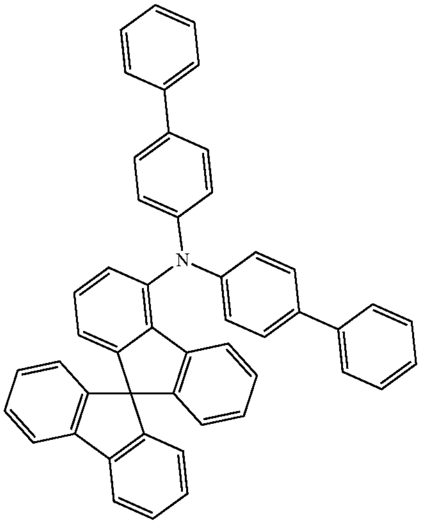 |
| HMT2 |
| [1450933-43-3] |
| 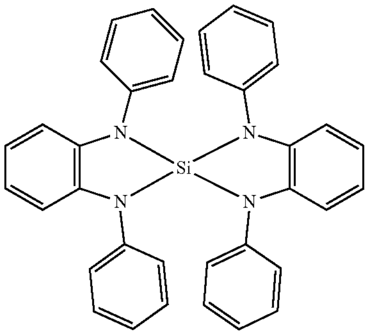 |
| HTM3 |
| [1206465-62-4] |
| WO2010045729 |
TABLE 4-continued
| Structural formulae of the materials used |
|---|
| 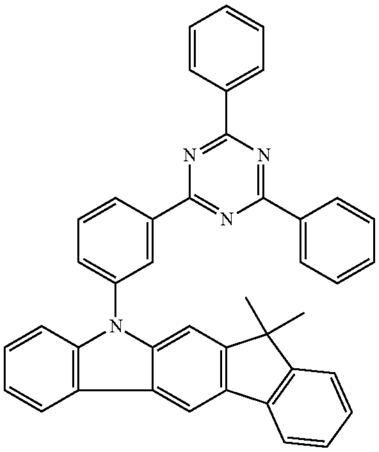 |
| M1 |
| [1257248-13-7] |
| 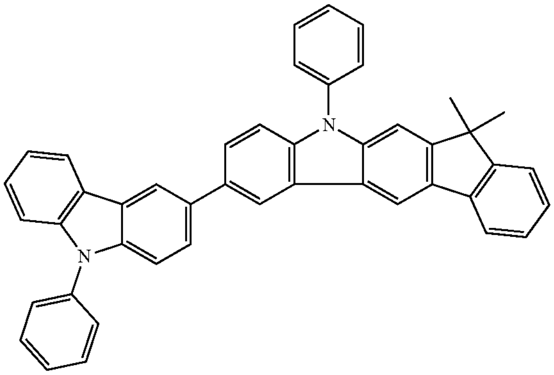 |
| M2 |
| [1357150-54-9] |
| 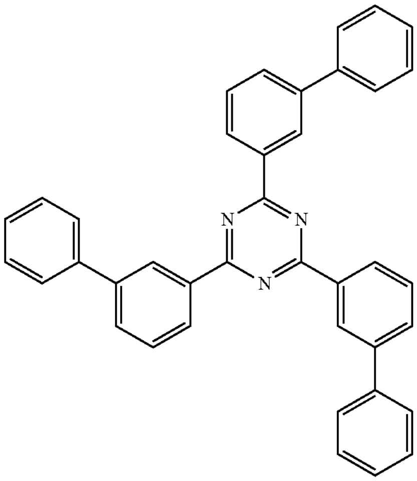 |
| M3 |
| [1201800-83-0] |

TABLE 4-continued
| Structural formulae of the materials used |
|---|
| 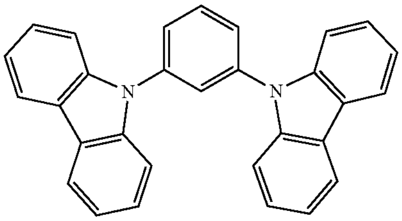 |
| M4<br>[550378-78-4] |
| 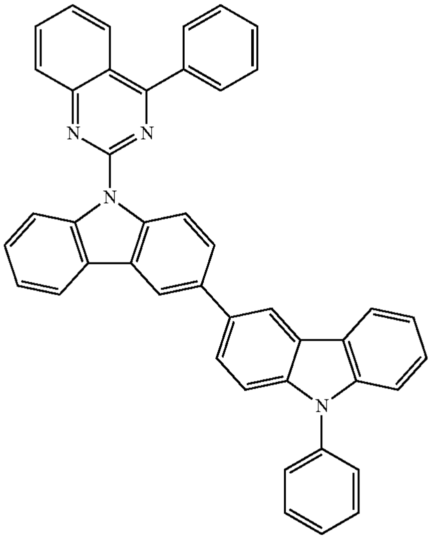 |
| M5<br>[1398398-92-0] |
| 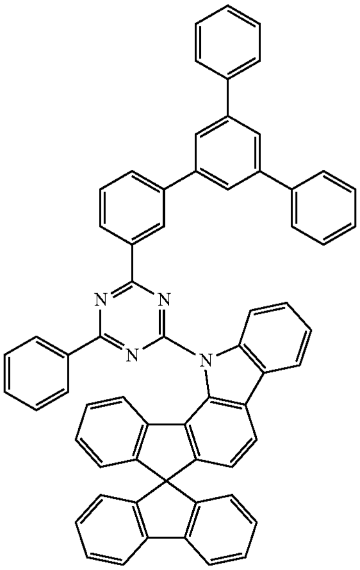 |
| M6<br>[1616231-60-7 |
TABLE 4-continued
| Structural formulae of the materials used |
|---|
| 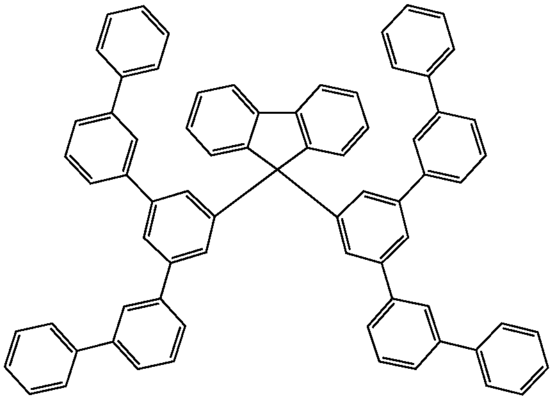 |
| M7<br>[1246496-85-4] |
| 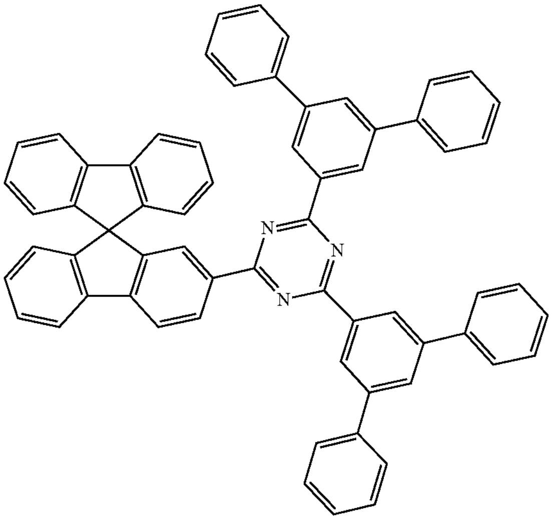 |
| ETM1 = M10<br>[1233200-52-6] |
| 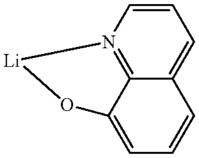 |
| ETM2<br>[25387-93-3] |

TABLE 4-continued
| Structural formulae of the materials used |
| --- |
| 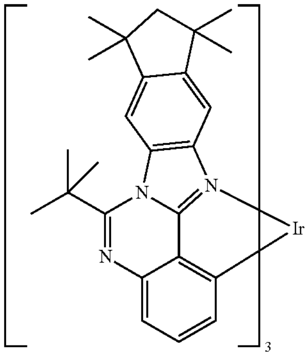 |
| IrB1 |
| 1541114-98-0 |
| 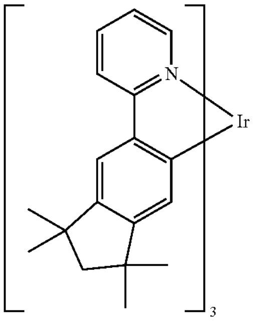 |
| IrG1 |
| 1562420-772 |
| 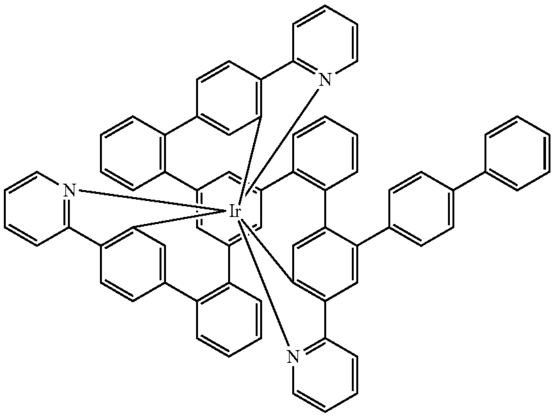 |
| IrG2 |
| 2245866-06-0 |
TABLE 4-continued
| Structural formulae of the materials used |
| --- |
| 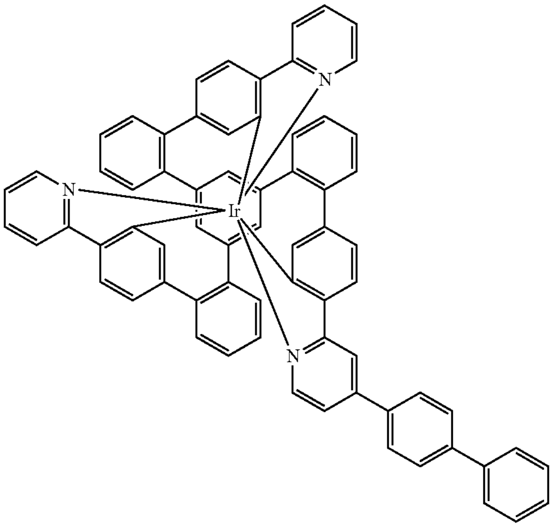 |
| IrG3 |
| 2245945-28-0 |
| 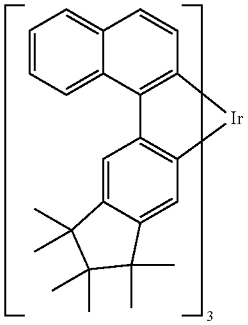 |
| IrR1 |
| 1562420-79-4 |

TABLE 4-continued

| Structural formulae of the materials used |
| --- |
| 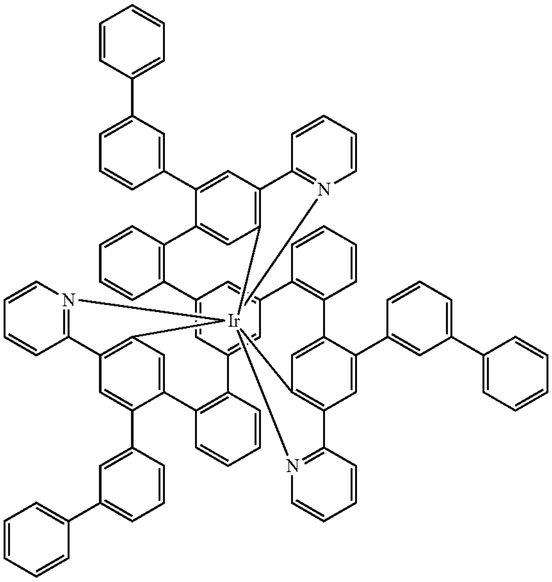<br>IrG-Sol1<br>1989601-89-9 |
| 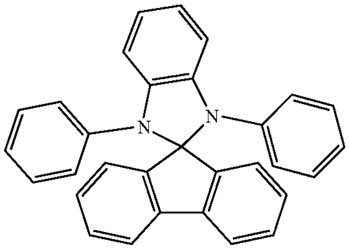<br>P 1-1<br>KR20190001967<br>2271415-09-7 |
| 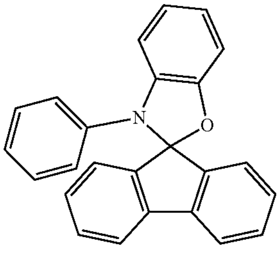<br>P 1-29<br>KR20190001967 |

The materials of the invention, when used as HTL2=EBL (Electron Blocking Layer), in the emission layer EML and in the hole blocker layer HBL (Hole Blocking Layer), lead to improved EQE (External Quantum Efficacy) in conjunction with reduced voltage and hence improved power efficiency overall.

The example data demonstrate that the materials claimed lead to an unexpected improvement over the prior art. With regard to the compounds of the invention, it is found that compounds of the formula (IIa) and (IIc) in many cases have slightly better properties than compounds of the formula (IId).

Moreover, the examples show that the properties resulting from the use of carbazole structures in many cases lead to improvements. Similarly, compounds having triazine and/or pyrimidine groups show improvements. Moreover, compounds having fused cyclic groups as described above as structures (RB) and/or (RA-1) to (RA-12) have very good properties.

Furthermore, compounds of the formula (IIIe) have advantages over compounds of the formula (IVd), as shown by the comparison of examples DG11 and DG12 with example DG5. Surprisingly, the use of compounds of the formula (IIIe) as hole blocker material leads to excellent device properties, as shown by example DG14.

The invention claimed is:

1. A compound selected from structure of the Formula (IIa), (IIb), (IIc) and (IId):

Formula (IIa)

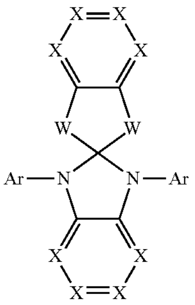

Formula (IIb)

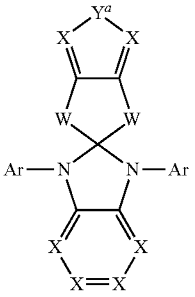

Formula (IIc)

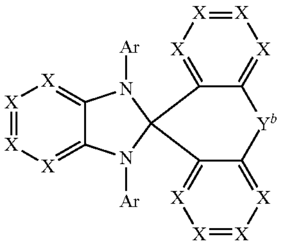

Formula (IId)

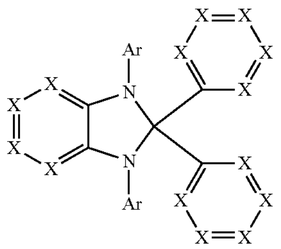

wherein:

$Y^a$ is O, S, S=O, $SO_2$, NR or NAr';

$Y^b$ is BR, $C(R)_2$, $Si(R)_2$, $Ge(R)_2$, C=O, C=NR, C=NAr', $C{=}C(R)_2$, O, S, S—O, $SO_2$, NR, N(Ar'), P(R) or P(=O)R;

W is the same or different at each instance and is NAr, NR, BAr, BR, O, S, P(=O)Ar, P(=O)R, S(=O), $S(=O)_2$;

Ar is the same or different at each instance and is an aromatic or heteroaromatic ring system which has 5 to 60 aromatic ring atoms and may be substituted by one or more R radicals; the Ar group here may form a ring system with at least one further group;

X is N, CR or C if the Ar group forms a ring system to that X via a bond, with the proviso that not more than two of the X groups in any cycle are N;

R is the same or different at each instance and is H, D, OH, F, Cl, Br, I, CN, $NO_2$, $N(Ar')_2$, $N(R^1)_2$, $C(=O)\,N(Ar')_2$, $C(=O)\,N(R^1)_2$, $C(Ar')_3$, $C(R^1)_3$, $Si(Ar')_3$, $Si(R^1)_3$, $B(Ar')_2$, $B(R^1)_2$, C(=O)Ar', $C(=O)R^1$, $P(=O)(Ar')_2$, $P(=O)(R^1)_2$, $P(Ar')_2$, $P(R^1)_2$, S(=O)Ar', $S(=O)R^1$, $S(=O)_2Ar'$, $S(=O)_2R^1$, $OSO_2Ar'$, $OSO_2R^1$, a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may in each case be substituted by one or more $R^1$ radicals, where one or more nonadjacent $CH_2$ groups may be replaced by $R^1C{=}CR^1$, C≡C, $Si(R^1)_2$, C=O, C=S, C=Se, $C{=}NR^1$, —C(=O)O—, $—C(=O)NR^1—$, $NR^1$, $P(=O)(R^1)$, —O—, —S—, SO or $SO_2$ or an aromatic or heteroaromatic ring system which has 5 to 60 aromatic ring atoms and may be substituted in each case by one or more $R^1$ radicals, or an aryloxy or heteroaryloxy group which has 5 to 60 aromatic ring atoms and may be substituted by one or more $R^1$ radicals; at the same time, two R radicals may also together or with a further group form a ring system;

Ar' is the same or different at each instance and is an aromatic or heteroaromatic ring system which has 5 to 60 aromatic ring atoms and may be substituted by one or more $R^1$ radicals; at the same time, it is possible for two Ar' radicals bonded to the same carbon atom, silicon atom, nitrogen atom, phosphorus atom or boron atom also to be joined together via a bridge by a single bond or a bridge selected from $B(R^1)$, $C(R^1)_2$, $Si(R^1)_2$, C=O, $C{=}NR^1$, $C{=}C(R^1)_2$, O, S, S=O, $SO_2$, $N(R^1)$, $P(R^1)$ and $P(=O)R^1$;

$R^1$ is the same or different at each instance and is H, D, F, Cl, Br, I, CN, $NO_2$, $N(Ar'')_2$, $N(R^2)_2$, C(=O) Ar'', $C(=O)R^2$, $P(=O)(Ar'')_2$, $P(Ar'')_2$, $B(Ar'')_2$, $B(R^2)_2$, $C(Ar'')_3$, $C(R^2)_3$, $Si(Ar'')_3$, $Si(R^2)_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl group having 2 to 40 carbon atoms, each of which may be substituted by one or more $R^2$ radicals, where one or more nonadjacent $CH_2$ groups may be replaced by $—R^2C{=}CR^2—$, —C≡C—, $Si(R^2)_2$, C=O, C=S, C=Se, $C{=}NR^2$, —C(=O)O—, $—C(=O)\,NR^2—$, $NR^2$, $P(=O)\,(R^2)$, —O—, —S—, SO or $SO_2$ and where one or more hydrogen atoms may be replaced by D, F, Cl, Br, I, CN or $NO_2$, or an aromatic or heteroaromatic ring system which has 5 to 60 aromatic ring atoms, each of which may be substituted by one or more $R^2$ radicals, or an aryloxy or heteroaryloxy group which has 5 to 60 aromatic ring atoms and may be substituted by one or more $R^2$ radicals, or an aralkyl or heteroaralkyl group which has 5 to 60 aromatic ring atoms and may be substituted by one or more $R^2$ radicals, or a combination of these systems; at the same time, two or more, optionally adjacent $R^1$ radicals together may form a ring system; at the same time, one or more $R^1$ radicals may form a ring system with a further part of the compound;

Ar'' is the same or different at each instance and is an aromatic or heteroaromatic ring system which has 5 to 30 aromatic ring atoms and may be substituted by one or more $R^2$ radicals; at the same time, it is possible for two Ar'' radicals bonded to the same carbon atom, silicon atom, nitrogen atom, phosphorus atom or boron atom also to be joined together via a bridge by a single bond or a bridge selected from $B(R^2)$, $C(R^2)_2$, $Si(R^2)_2$, C=O, $C{=}NR^2$, $C{=}C(R^2)_2$, O, S, S=O, $SO_2$, $N(R^2)$, $P(R^2)$ and $P(=O)R^2$;

$R^2$ is the same or different at each instance and is selected from the group consisting of H, D, F, CN, an aliphatic hydrocarbyl radical having 1 to 20 carbon atoms or an aromatic or heteroaromatic ring system which has 5 to 30 aromatic ring atoms and in which one or more hydrogen atoms may be replaced by D, F, Cl, Br, I or CN and which may be substituted by one or more alkyl groups each having 1 to 4 carbon atoms; at the same time, two or more, adjacent substituents $R^2$ together may form a ring system; and wherein compounds of formula A are excluded:

Formula (A)

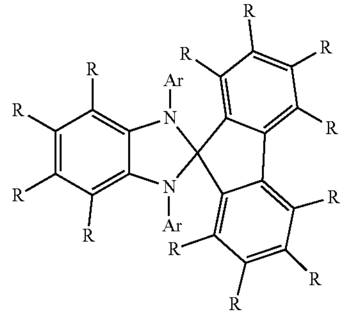

where the symbols Ar and R have the definition above.

2. A compound as claimed in claim 1, selected from structure of the Formulae (IIIa), (IIIb), (IIIc), (IIId) and (IIIe):

Formula (IIIa)

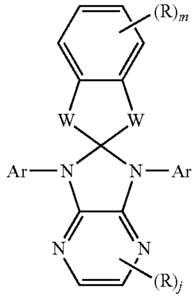

-continued

Formula (IIIb)

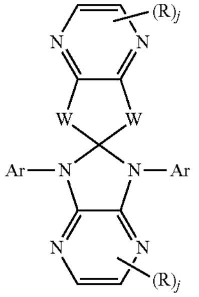

Formula (IIIc)

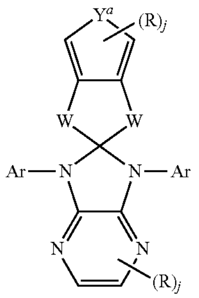

Formula (IIId)

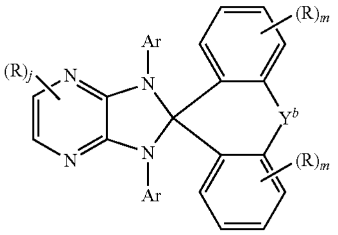

Formula (IIIe)

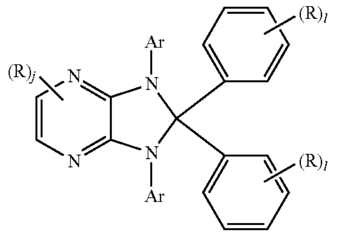

where W, $Y^a$, $Y^b$, R and Ar have the definitions given in claim 1, the index l is 0, 1, 2, 3, 4 or 5, the index m is 0, 1, 2, 3 or 4, and the index j is 0, 1 or 2.

3. A compound as claimed in claim 1, selected from structure of the Formulae (IVa), (IVb), (IVc) and (IVd):

Formula (IVa)

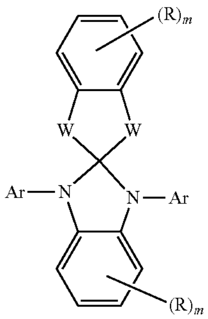

-continued

Formula (IVb)

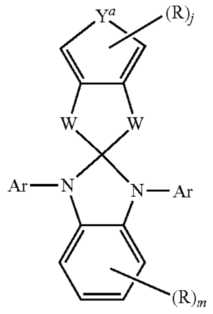

Formula (IVc)

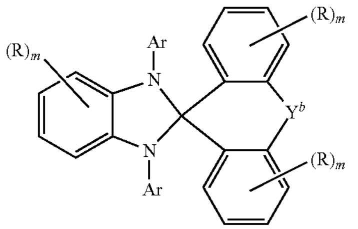

Formula (IVd)

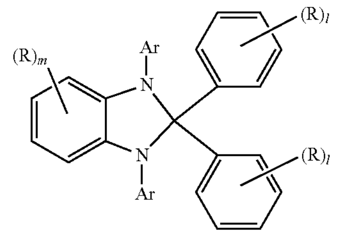

where W, $Y^a$, $Y^b$, R and Ar have the definitions given in claim 1, the index l is 0, 1, 2, 3, 4 or 5, the index m is 0, 1, 2, 3 or 4, and the index j is 0, 1 or 2.

4. A compound as claimed in claim 1, wherein at least one of the W radicals represents NR or NAr.

5. A compound as claimed in claim 1, wherein at least one of the W radicals represents BR or BAr.

6. A compound as claimed in claim 1, wherein at least one of the W radicals represents O, S, S(=O), $S(=O)_2$.

7. A compound as claimed in claim 1, at least one of the W radicals represents NR or NAr, and at least one of the W radicals is BAr, BR, O or S.

8. A compound as claimed in claim 1, selected from structure of the Formulae (Va) to (Ve):

Formula (Va)

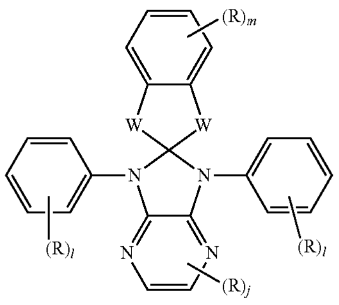

-continued

Formula (Vb)

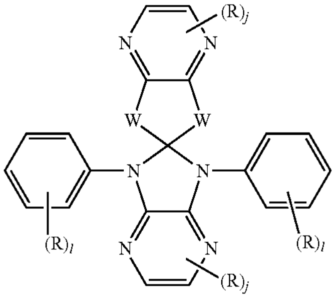

Formula (Vc)

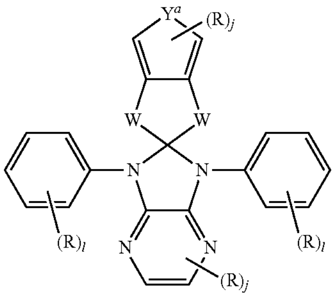

Formula (Vd)

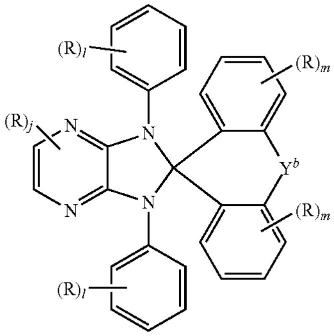

Formula (Ve)

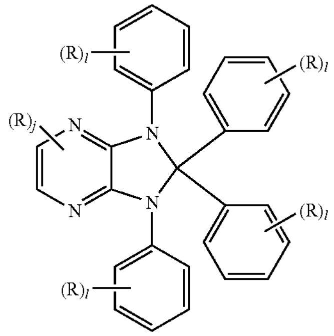

where W, $Y^a$, $Y^b$ and R have the definitions given in claim 1, the index l is 0, 1, 2, 3, 4 or 5, the index m is 0, 1, 2, 3 or 4, and the index j is 0, 1 or 2.

9. A compound as claimed in claim 1, selected from structure of the Formulae (VIa) to (VId):

Formula (VIa)

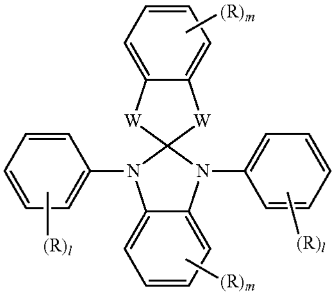

Formula (VIb)

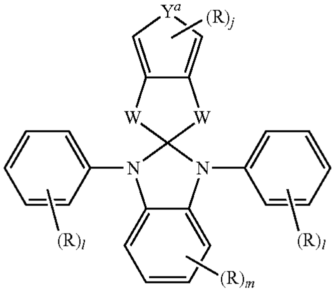

Formula (VIc)

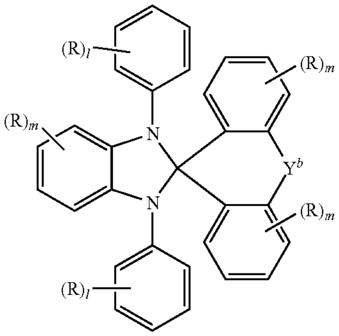

Formula (VId)

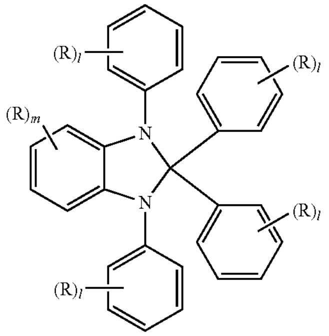

where W, $Y^a$, $Y^b$ and R have the definitions given in claim 1, the index l is 0, 1, 2, 3, 4 or 5, the index m is 0, 1, 2, 3 or 4, and the index j is 0, 1 or 2.

10. A compound as claimed in claim 1, selected from structure of the Formulae (VIa-1) to (VIb-13):
Formula (VIa-1)
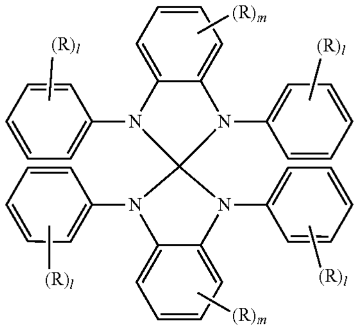
Formula (VIb-1)
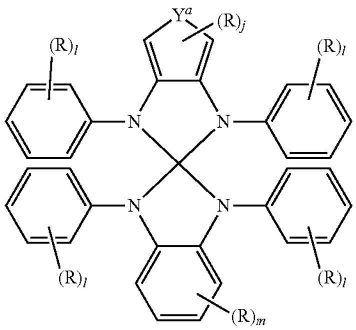
Formula (VIa-2)
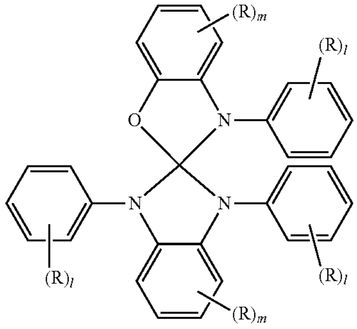
Formula (VIb-2)
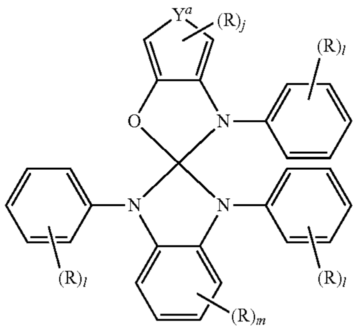
-continued
Formula (VIa-3)
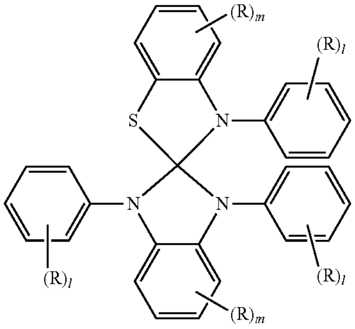
Formula (VIb-3)
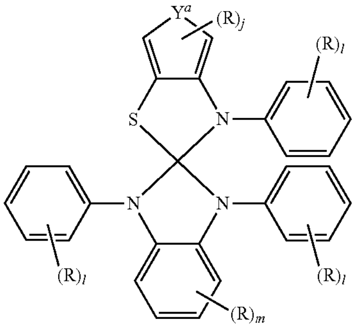
Formula (VIa-4)
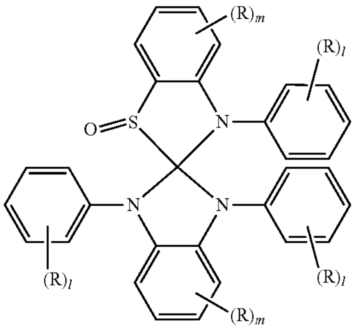
Formula (VIb-4)
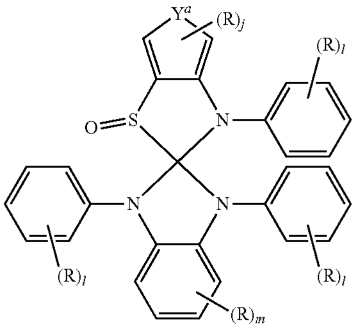

-continued
Formula (VIa-5)
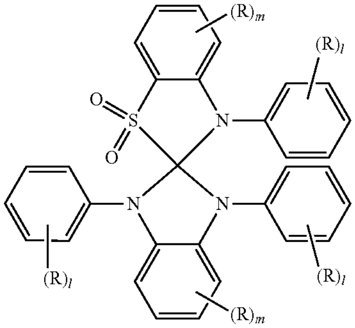
Formula (VIb-5)
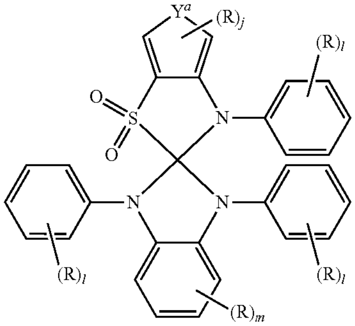
Formula (VIa-6)
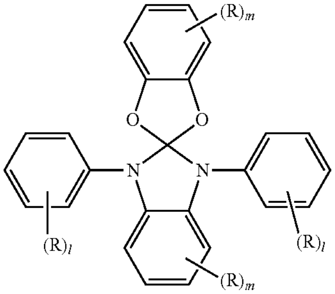
Formula (VIb-6)
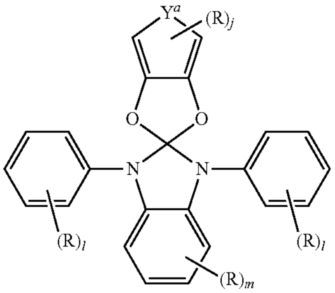
Formula (VIa-7)
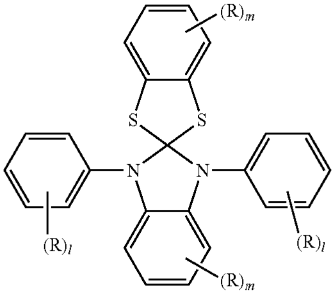
-continued
Formula (VIb-7)
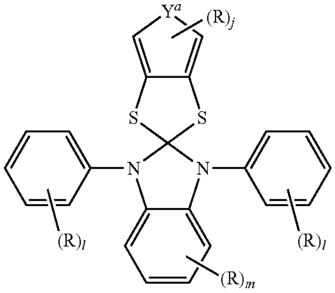
Formula (VIa-8)
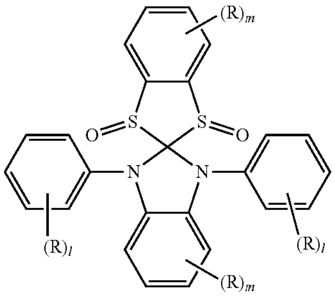
Formula (VIb-8)
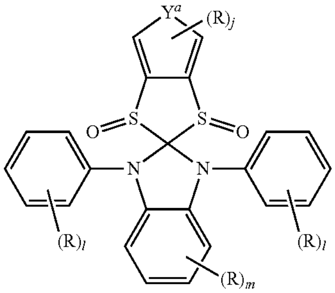
Formula (VIa-9)
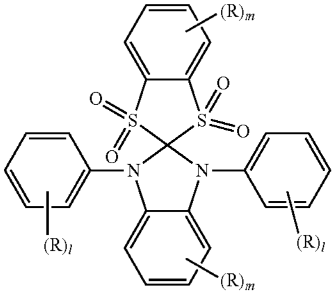
Formula (VIb-9)
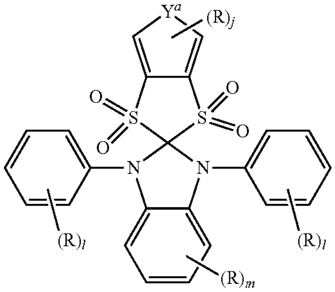

-continued

Formula (VIa-10)

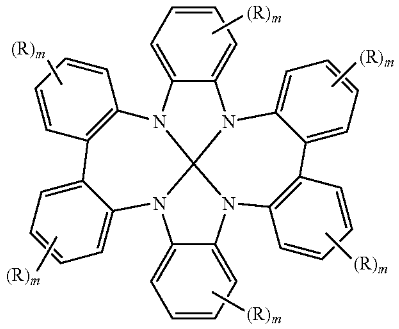

Formula (VIb-10)

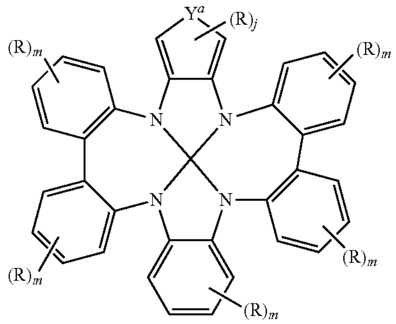

Formula (VIa-11)

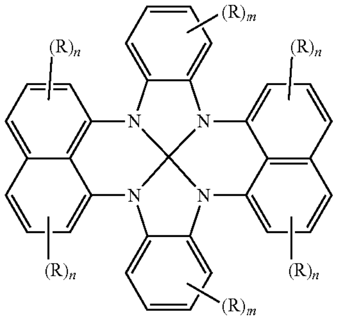

Formula (VIb-11)

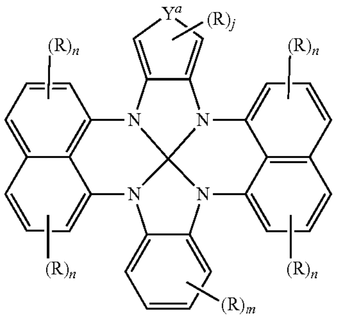

Formula (VIa-12)

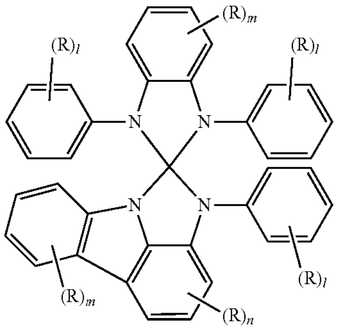

-continued

Formula (VIb-12)

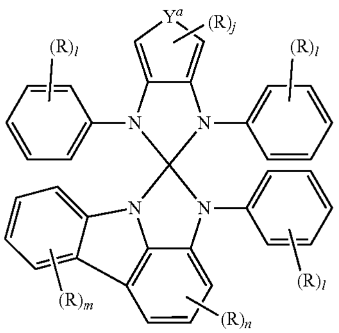

Formula (VIa-13)

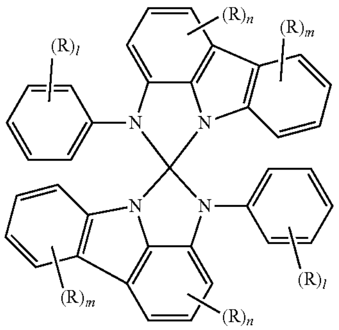

Formula (VIb-13)

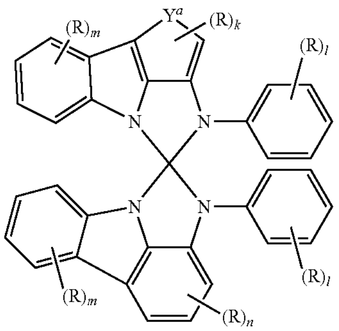

where $Y^a$ and R have the definitions given in claim 1, the index l is 0, 1, 2, 3, 4 or 5, the index m is 0, 1, 2, 3 or 4, the index m is 0, 1, 2 or 3, the index j is 0, 1 or 2 and the index k is 0 or 1.

11. A compound as claimed in claim 1, wherein at least two R radicals form a fused ring together with the further groups to which the two R radicals bind, where the two R radicals form at least one structure of the Formulae (RA-1) to (RA-12):

Formula RA-1

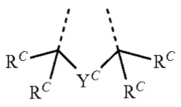

Formula RA-2

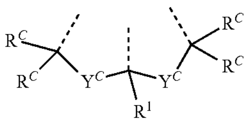

-continued

Formula RA-3

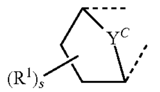

Formula RA-4

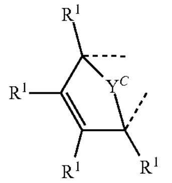

Formula RA-5

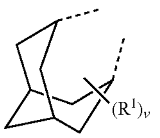

Formula RA-6

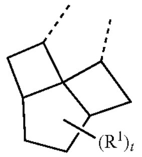

Formula RA-7

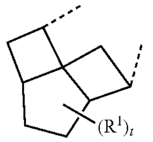

Formula RA-8

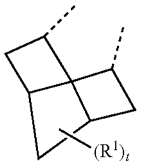

Formula RA-9

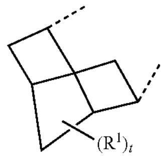

Formula RA-10

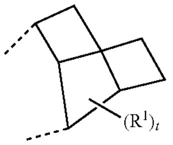

Formula RA-11

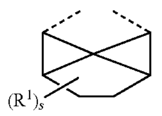

Formula RA-12

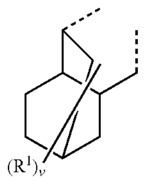

where $R^1$ has the definition set out above, the dotted bonds represent the sites of attachment to the atoms of the groups to which the two R radicals bind, and the further symbols have the following definition:

$Y^c$ is the same or different at each instance and is $C(R^1)_2$, $(R^1)_2C{=}C(R^1)_2$, $(R^1)C{=}C(R^1)$, $NR^1$, NAr', O or S;

$R^c$ is the same or different at each instance and is F, a straight-chain alkyl, alkoxy or thioalkoxy group having 1 to 40 carbon atoms or an alkyl or alkenyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may be substituted in each case by one or more $R^2$ radicals, where one or more adjacent $CH_2$ groups may be replaced by $R^2C{=}CR^2$, C≡C, $Si(R^2)_2$, C=O, C=S, C=Se, $C{=}NR^2$, —C(=O)O—, $—C(=O)NR^2—$, $NR^2$, $P(=O)(R^2)$, —O—, —S—, SO or $SO_2$, or an aromatic or heteroaromatic ring system which has 5 to 60 aromatic ring atoms and may be substituted in each case by one or more $R^2$ radicals, or an aryloxy or heteroaryloxy group which has 5 to 60 aromatic ring atoms and may be substituted by one or more $R^2$ radicals, where $R^2$ has the definition detailed above; at the same time, it is also possible for two $R^c$ radicals together to form a ring system;

s is 0, 1, 2, 3, 4, 5 or 6;

t is 0, 1, 2, 3, 4, 5, 6, 7 or 8;

v is 0, 1, 2, 3, 4, 5, 6, 7, 8 or 9.

12. A compound as claimed in claim 1, that at least two R radicals form a fused ring together with the further groups to which the two R radicals bind, where the two R radicals form of the structures of the Formula (RB):

Formula RB

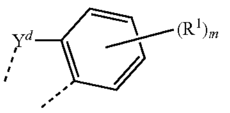

where $R^1$ has the definition set out in claim 1, the index m is 0, 1, 2, 3 or 4, and $Y^d$ is $C(R^1)_2$, $NR^1$, NAr', $BR^1$, BAr', O or S.

13. An oligomer, polymer or dendrimer containing one or more compounds as claimed in claim 1, wherein, rather than a hydrogen atom or a substituent, there are one or more bonds of the compounds to the polymer, oligomer or dendrimer.

14. A formulation comprising at least one compound as claimed in claim 1 and at least one further compound, where the further compound is selected from one or more solvents.

15. A composition comprising at least one compound as claimed in claim 1 and at least one further compound selected from the group consisting of fluorescent emitters, phosphorescent emitters, emitters that exhibit TADF, host materials, electron transport materials, electron injection materials, hole conductor materials, hole injection materials, electron blocker materials and hole blocker materials.

16. A process for preparing a compound as claimed in claim 1, wherein a base skeleton having two aromatic amino groups is synthesized and this is then converted to a compound selected from structure of the Formula (IIa), (IIb), (IIc) and (IId) by means of a nucleophilic aromatic substitution reaction, a nucleophilic addition reaction or a coupling reaction.

17. An electronic device comprising at least one compound as claimed in claim 1, wherein the electronic device is an organic electroluminescent device.

* * * * *